(12) United States Patent
Zelder et al.

(10) Patent No.: US 8,148,117 B2
(45) Date of Patent: Apr. 3, 2012

(54) MICROORGANISM AND PROCESS FOR THE PREPARATION OF L-METHIONINE

(75) Inventors: Oskar Zelder, Speyer (DE); Andrea Herold, Ludwigshafen (DE); Corinna Klopprogge, Mannheim (DE); Hartwig Schröder, Nussloch (DE); Stefan Haefner, Speyer (DE); Elmar Heinzle, Saarbruecken (DE); Christoph Wittmann, Saarbruecken (DE); Jens Kroemer, Riegelsberg (DE); Janice G. Pero, Lexington, MA (US); R. Rogers Yocum, Lexington, MA (US); Thomas A. Patterson, North Attleboro, MA (US); Mark Williams, Revere, MA (US); Theron Herman, Kinnelon, NJ (US)

(73) Assignee: Evonik Degussa GmbH, Essen (DE)

( * ) Notice: Subject to any disclaimer, the term of this patent is extended or adjusted under 35 U.S.C. 154(b) by 375 days.

(21) Appl. No.: 12/091,948

(22) PCT Filed: Oct. 23, 2006

(86) PCT No.: PCT/EP2006/067680
§ 371 (c)(1),
(2), (4) Date: Nov. 21, 2008

(87) PCT Pub. No.: WO2007/051725
PCT Pub. Date: May 10, 2007

(65) Prior Publication Data
US 2009/0298137 A1 Dec. 3, 2009

(30) Foreign Application Priority Data
Oct. 31, 2005 (EP) .................... 05110210

(51) Int. Cl.
C12P 13/12 (2006.01)
C12N 9/00 (2006.01)
C12N 15/00 (2006.01)
C12N 1/21 (2006.01)

(52) U.S. Cl. .................. 435/113; 435/252.32; 435/440; 435/183

(58) Field of Classification Search ............... 435/252.3, 435/113, 440, 183, 252.33, 252.34, 252.32, 435/252.31
See application file for complete search history.

(56) References Cited

FOREIGN PATENT DOCUMENTS
WO   WO-02/097096 A2   12/2002
WO   WO-2006/008152 A1   1/2006

OTHER PUBLICATIONS

Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Zhou et al., Cell Mol Life Sci 63(19-20):2260-2290, 2006.*
Kozak, M., Gene 234:187-208, 1999.*
Sousa et al., Microbiology 148(Pt5):1291-1303, 2002.*
Trötschel, C., et al., "Characterization of Methionine Export in *Corynebacterium gultamicum*", Journal of Bacteriology, vol. 187, No. 11, (2005), pp. 3786-3794.
Krömer, J.O at al., "Accumulation of Homolanthionine and Activation of a Novel Pathway for Isoleucine Biosynthesis in *Corynebacterium glutamicum* McbR Deletion Strains", Journal of Bacteriology, vol. 188, No. 2, (2006), pp. 609-618.
Mampel, J., et al., "Single-gene Knockout of a Novel Regulatory Element Confers Ethionine Resistance and Elevates Methionine Production in *Corynebacterium glutamicum*", Applied Microbiology and Biotechnology, vol. 68, No. 2, (2005), pp. 228-236.
Rückert, C., et al., "Genome-wide Analysis of the L-Methionine Biosynthetic Pathway in *Corynebacterium glutamicum* by Targeted Gene Deletion and Homologous Complementation", Journal of Biotechnology, vol. 104, No. 1-3, (2003), pp. 213-228.

* cited by examiner

*Primary Examiner* — Delia Ramirez
(74) *Attorney, Agent, or Firm* — Smith, Gambrell & Russell, LLP

(57) ABSTRACT

The present invention relates to microorganisms and processes for the efficient preparation of L-amino acids such as L-methionine. In particular, the present invention relates to microorganisms and processes in which the formation and/or accumulation of homolanthionine in the methionine pathway is reduced and/or prevented.

9 Claims, 7 Drawing Sheets a) pH430 delta mcbR b) pH238 delta hom/hsdh hsk c) pSL315

MICROORGANISM AND PROCESS FOR THE PREPARATION OF L-METHIONINE

RELATED APPLICATIONS

This application is a national stage application (under 35 U.S.C. 371) of PCT/EP2006/067680 filed Oct. 23, 2006, which claims benefit of European application 05110210.1 filed Oct. 31, 2005.

SEQUENCE LISTING SUBMISSION

The Sequence Listing associated with this application is filed in electronic format via EFS-Web and hereby incorporated by reference into the specification in its entirety. The name of the text file containing the Sequence Listing is SequenceListing_13477_00011. The size of the text file is 23 KB, and the text file was created on Apr. 29, 2008.

FIELD OF THE INVENTION

The present invention relates to microorganisms and processes for the efficient preparation of L-methionine. In particular, the present invention relates to micro-organisms and processes in which the formation and/or accumulation of homolanthionine in the methionine pathway is reduced and/or prevented.

TECHNOLOGICAL BACKGROUND

Currently, worldwide annual production of methionine is about 500,000 tons. Methionine is the first limiting amino acid in livestock of poultry feed and due to this, mainly applied as feed supplement. In contrast to other industrial amino acids, methionine is almost exclusively applied as a racemate produced by chemical synthesis. Since animals can metabolise both stereo isomers of methionine, direct feed of the chemically produced racemic mixture is possible (D'Mello and Lewis, Effect of Nutrition Deficiencies in Animals: Amino Acids, Rechgigl (Ed.), CRC Handbook Series in Nutrition and Food, 441-490, 1978).

However, there is still a great interest in replacing the existing chemical production by a biotechnological process. This is due to the fact that at lower levels of supplementation L-methionine is a better source of sulfur amino acids than D-methionine (Katz and Baker, (1975) Poult. Sci., 545, 1667-74). Moreover, the chemical process uses rather hazardous chemicals and produces substantial waste streams. All these disadvantages of chemical production could be avoided by an efficient biotechnological process.

For other amino acids such as glutamate, it has been known to produce them using fermentation methods. For these purposes, certain microorganisms such as *Escherichia coli* (*E. coli*) and *Corynebacterium glutamicum* (*C. glutamicum*) have proven to be particularly suited. The production of amino acids by fermentation also has the particular advantage that only L-amino acids are produced. Further, environmentally problematic chemicals such as solvents, etc. which are used in chemical synthesis are avoided. However, fermentative production of methionine by microorganisms will only be an alternative to chemical synthesis if it allows for the production of methionine on a commercial scale at a price comparable to that of chemical production.

Hence, the production of L-methionine through large-scale culture of bacteria developed to produce and secrete large quantities of this molecule is a desirable goal. Improvements to the process can relate to fermentation measures, such as stirring and supply of oxygen, or the composition of the nutrient media, such as the sugar concentration during fermentation, or the working up of the product by, for instance, ion exchange chromatography, or the intrinsic output properties of the microorganism itself.

Methods of mutagenesis, selection and mutant selection are also used to improve the output properties of these microorganisms. High production strains which are resistant to antimetabolites or which are auxotrophic for metabolites of regulatory importance are obtained in this manner.

Recombinant DNA technology has also been employed for some years for improving microorganism strains which produce L-amino acids by amplifying individual amino acid biosynthesis genes and investigating the effect on the amino acid production.

Rückert et al., Journal of Biotechnology 2003, 104, 213-228 provide an analysis of the L-methionine biosynthetic pathway in *Corynebacterium glutamicum*. Known functions of MetZ (also known as MetY) and MetB could be confirmed and MetC (also known as AecD) was proven to be a cystathionine-β-lyase. Further, MetE and MetH, which catalyse the conversion of L-homocysteine to L-methionine, were identified in this study.

WO 02/097096 uses nucleotide sequences from coryneform bacteria which code for the McbR repressor gene (also known as MetD) and processes for the preparation of amino acids using bacteria in which this McbR repressor gene is attenuated. According to WO 02/097096, the attenuation of the transcriptional regulator McbR improves the production of L-methionine in coryneform bacteria. It is further described in WO 02/097096 that, in addition to the attenuation of the McbR repressor gene, enhancing or overexpressing the MetB gene which codes for cystathionine-γ-synthase is preferred for the preparation of L-methionine.

Selection of strains improved for the production of a particular molecule is a time-consuming and difficult process. Therefore, there is still a great need for microorganisms which efficiently produce L-methionine and/or have significantly increased contents of L-methionine which can be utilized for obtaining the methionine compounds.

SUMMARY OF THE INVENTION

It is an object of the present invention to provide methods for the efficient production of L-methionine in microorganisms.

It is a further object of the present invention to provide microorganisms which efficiently produce L-methionine.

These and further objects of the invention, as will become apparent from the description, are attained by the subject-matter of the independent claims.

Further embodiments of the invention are defined by the dependent claims.

According to one embodiment of the present invention, a microorganism for the preparation of L-methionine is provided, wherein the formation and/or accumulation of homolanthionine, in particular in the methionine pathway is reduced and/or prevented. Such a reduction and/or prevention of the formation and/or accumulation of homolanthionine in the pathway for the biosynthesis of L-methionine may make it possible for a microorganism to produce and secrete large quantities of the desired molecule, i.e. L-methionine.

In a further embodiment of the present invention, a microorganism is provided, wherein the content and/or the biological activity of the transcriptional regulator protein McbR is reduced compared to the wild type microorganism and wherein the formation and/or accumulation of homolanthionine, in particular in the methionine pathway, is reduced and/or prevented.

According to a further embodiment of the present invention, a microorganism is provided, wherein the formation and/or accumulation of homolanthionine in the methionine pathway is reduced and/or prevented by reducing the content and/or the biological activity of cystathionine-γ-synthase (MetB, EC 2.5.1.48) compared to the wild type microorganism.

In another embodiment of the present invention, the content and/or the biological activity of MetB is reduced by attenuating or disrupting and/or eliminating the gene which codes for MetB.

According to a further embodiment of the process according to the present invention, the disrupted MetB gene prevents the expression of a functional MetB protein in the cultivated microorganisms.

In one embodiment of the microorganisms according to the present invention, a gene which codes for McbR is attenuated, preferably disrupted and more preferably eliminated. In particular, the disrupted McbR gene may prevent the expression of a functional McbR protein in a microorganism according to the present invention.

According to a further embodiment, a microorganism is provided in which a gene of either homologous or heterologous origin coding for methionine synthase which is capable of efficiently converting homocysteine into methionine, i.e. metE (EC 2.1.1.13) and/or metH (EC 2.1.1.14) is introduced and/or overproduced.

According to a further aspect of the present invention, a process for the preparation of L-methionine is provided which comprises the following steps:
  cultivating and/or fermenting a microorganism which produces the L-methionine and in which the formation and/or accumulation of homolanthionine in the methionine pathway is reduced and/or prevented; and
  isolating L-methionine.

According to a further embodiment of the process according to the present invention, organisms are cultivated in which the content and/or the biological activity of the transcriptional regulator protein McbR is reduced compared to the wild type micro-organism.

According to a further embodiment of the process of the present invention, microorganisms are cultivated in which a gene which codes for McbR is attenuated and/or disrupted and/or eliminated.

According to a further embodiment of the process of the present invention, the disrupted McbR gene prevents the expression of a functional McbR protein.

According to a further embodiment of the process of the present invention, microorganisms are cultivated in which a heterologous gene coding for cystathionine-β-lyase (MetC) mutant is introduced which is capable of efficiently converting homolanthionine into homocysteine.

According to a further embodiment of the process of the present invention, microorganisms are cultivated in which a heterologous gene coding for a cystathionine-γ-synthase (MetB) is introduced which is capable of efficiently converting O-acetyl-homoserine and cysteine into cystathione and which is not capable of converting O-acetyl-homoserine and homocysteine into homolanthionine.

According to a further embodiment of the process of the present invention, microorganisms are cultivated in which the content and/or the biological activity of a protein selected from the group consisting of O-acetyl-homoserine sulfhydrolase (MetZ), cob(I)alamin dependent methionine synthase I (MetH) and cob(I)alamin independent methionine synthase II (MetE) is increased compared to the wild type microorganism.

According to a further embodiment of the process of the present invention, micro-organisms are cultivated in which at least one gene coding for a protein selected from the group consisting of O-acetyl-homoserine sulfhydrolase (MetZ), cob(I)alamin dependent methionine synthase I (MetH) and cob(I)alamin independent methionine synthase II (MetE) is enhanced and/or over-expressed compared to the wild type microorganism.

According to a further embodiment of the process of the present invention, the microorganism is selected from the group consisting of coryneform bacteria, mycobacteria, streptomycetaceae, *salmonella, Escherichia coli, Shigella, Bacillus, Serratia* and *Pseudomonas*.

According to a further preferred embodiment of the process of the present invention, the organism is *Corynebacterium glutamicum, Escherichia coli, Saccharomyces cerevisiae* or *Bacillus subtilis*.

According to a further embodiment of the process of the present invention, the desired L-amino acid is concentrated in the medium or in the cells of the microorganism.

In a further aspect of the present invention, a process for the preparation of an L-methionine containing animal feedstuff additive from fermentation broths is provided which comprises the following steps:
  cultivating and/or fermenting a microorganism which produces L-methionine and in which the formation and/or accumulation of homolanthionine in the methionine pathway is reduced and/or prevented in a fermentation medium;
  removing water from the L-methionine-containing fermentation broth;
  removing an amount of 0 to 100 wt.-%, such as 10 to 90 wt.-% or 20 to 80 wt.-% or 30 to 70 wt.-% or 40 to 60 wt.-% or about 50% wt.-% of the biomass formed during fermentation, and
  drying the fermentation broth to obtain the animal feedstuff additive in powder or granule form.

Further, another aspect of the present invention relates to the use of a microorganism, in particular *Corynebacterium glutamicum*, in which the formation and/or accumulation of homolanthionine in the methionine pathway is reduced and/or prevented, for the production of L-methionine.

m/z=678 and m/z=692 equals the m-signal of cystathionine and homolanthionine, respectively. Characteristic m-15, m-57 and m-302 can also be observed with a mass shift of 14. m/z=170, m/z=244 and m/z=272 are characteristic fragments of the homocysteine residue in both molecules.

Figure 4:
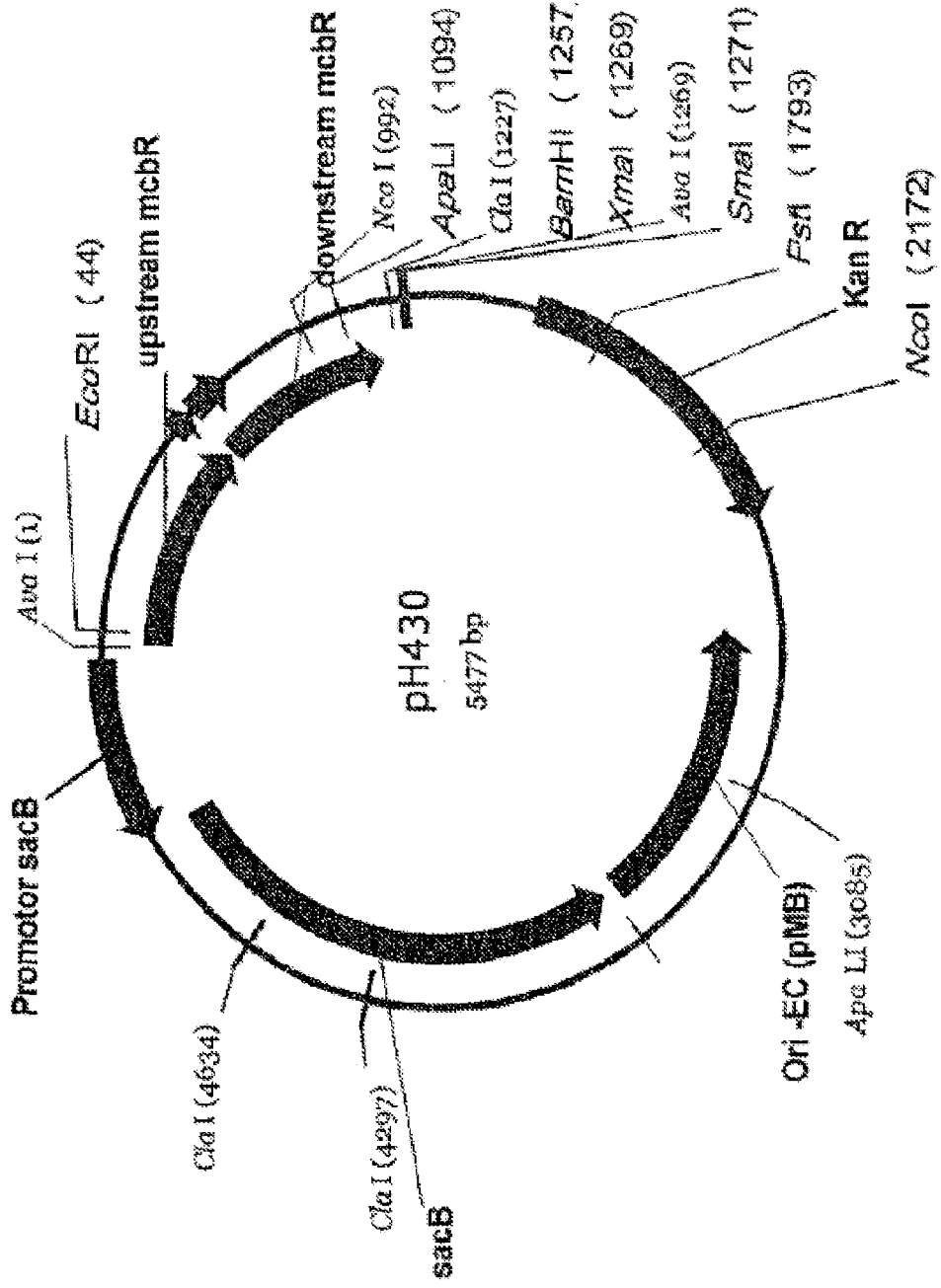
Figure 4:
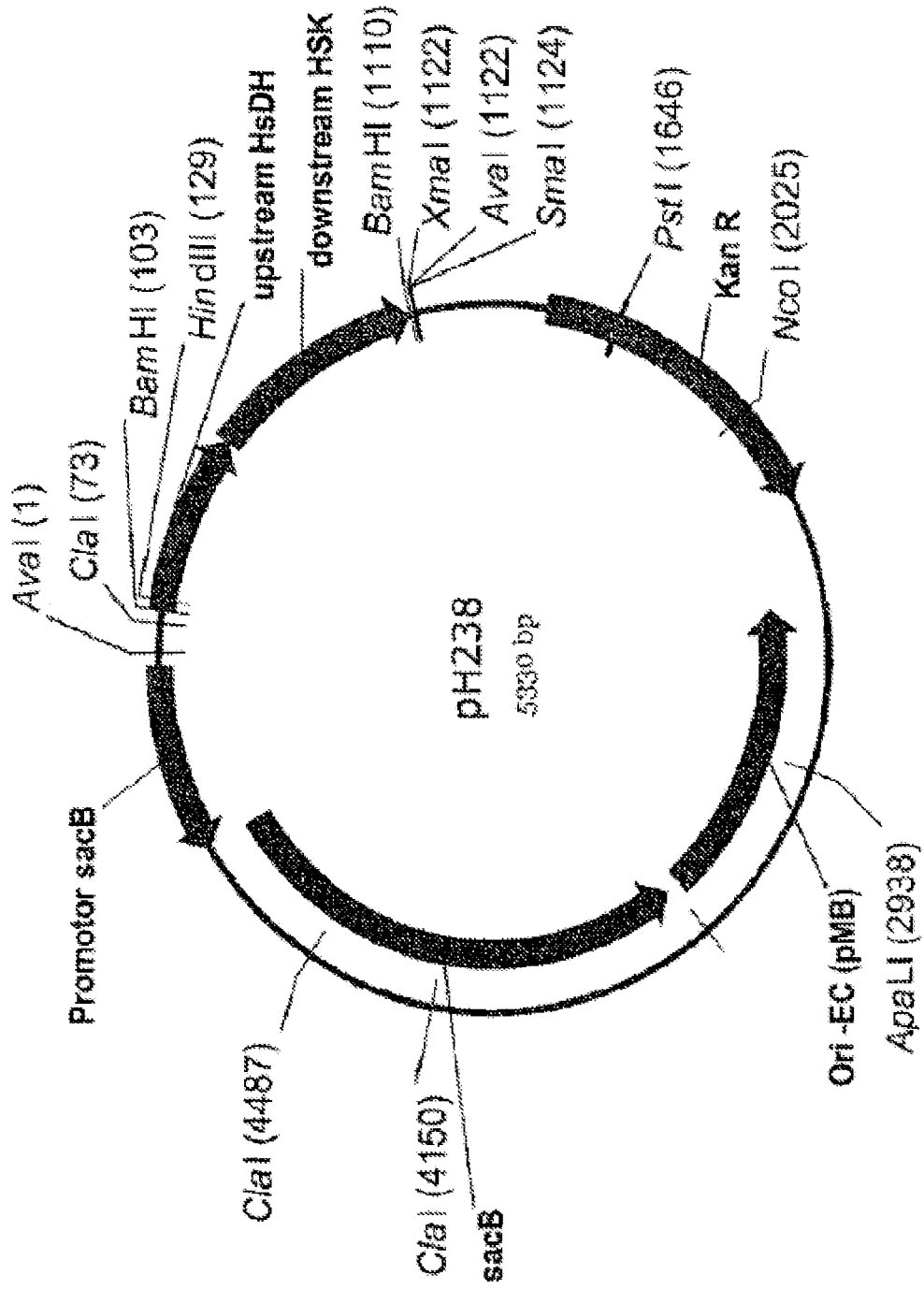
Figure 4:
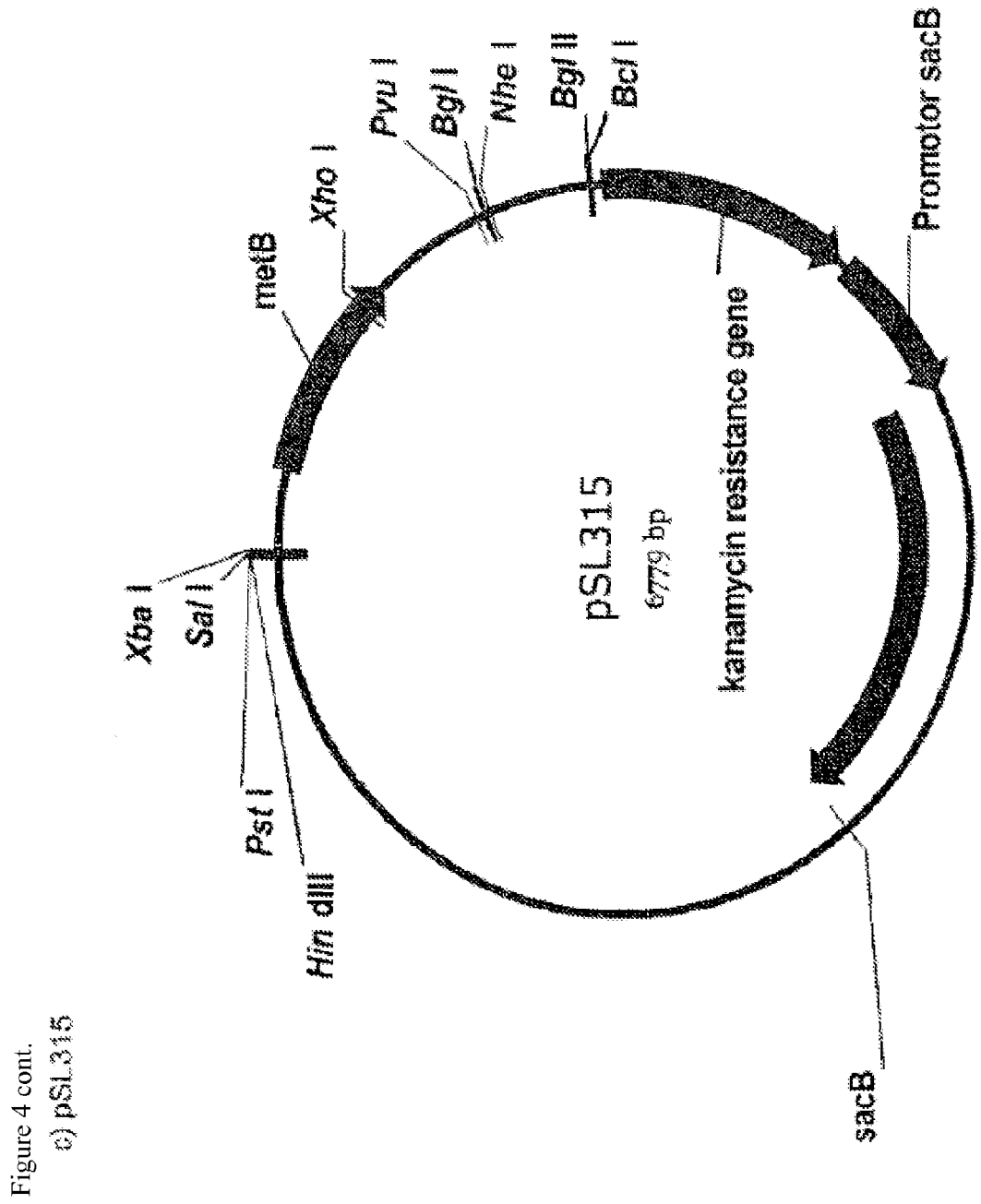

FIG. 4 shows plasmids pH430 ΔMcbR (a), pH238 delta Δhom/Δhsdh-hsk (b) and pSL315 (c).

DETAILED DESCRIPTION OF EXEMPLARY EMBODIMENTS

Before describing in detail exemplary embodiments of the present invention, the following definitions are given.

The term "efficiency of methionine synthesis" describes the carbon yield of methionine. This efficiency is calculated as a percentage of the energy input which entered the system in the form of a carbon substrate. Throughout the invention this value is given in percent values ((mol methionine) (mol carbon substrate)$^{-1}$×100) unless indicated otherwise.

The term "efficiency of homolanthionine synthesis" describes the carbon yield of homolanthionine. This efficiency is calculated as a percentage of the energy input which entered the system in the form of a carbon substrate. Throughout the invention this value is given in percent values ((mol homolanthionine) (mol carbon substrate)$^{-1}$×100) unless indicated otherwise.

Preferred carbon sources according to the present invention are sugars, such as mono-, di-, or polysaccharides. For example, sugars selected from the group consisting of glucose, fructose, mannose, galactose, ribose, sorbose, ribose, lactose, maltose, sucrose, raffinose, starch or cellulose may serve as particularly preferred carbon sources.

The term "increased efficiency of methionine synthesis" relates to a comparison between an organism that has been genetically modified and which has a higher efficiency of methionine synthesis compared to the initial wild type organism.

The term "yield of methionine" describes the yield of methionine which is calculated as the amount of methionine obtained per weight cell mass.

Figure 1A:
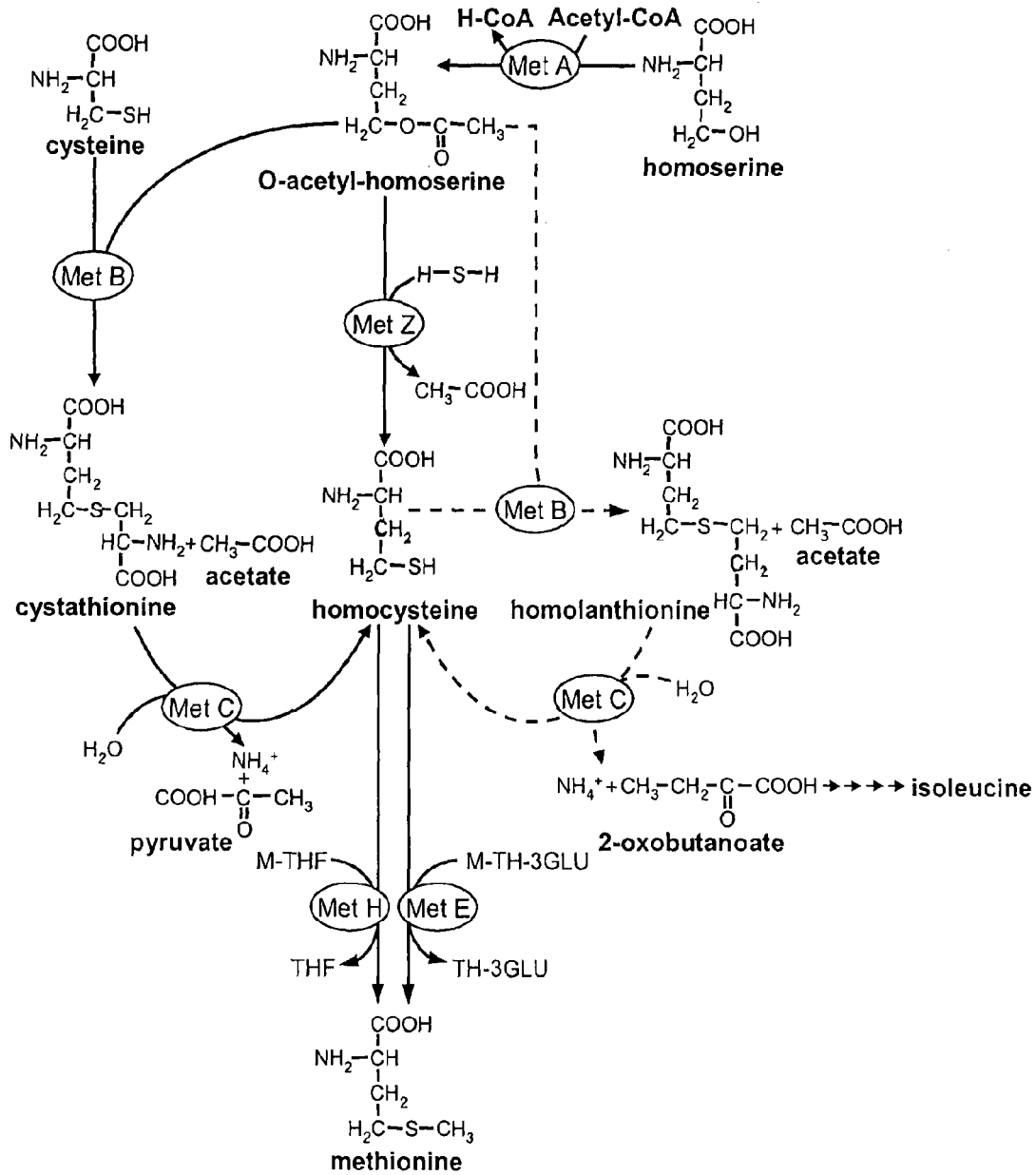
FIG. 1a is a model of the pathway for L-methionine biosynthesis in microorganisms such as *C. glutamicum*. Enzymes involved are MetA (homoserine transacetylase), MetB (cystathionine-γ-synthase), MetZ (O-acetylhomoserine sulfhydrolase), MetC (cystathionine-β-lyase), cob(I)alamin dependent methionine synthase I (MetH) and cob(I)alamin independent methionine synthase II (MetE).

The term "methionine pathway" is art-recognized and describes a series of reactions which take place in a wild type organism and lead to the biosynthesis of methionine. The pathway may vary from organism to organism. The details of an organism-specific pathway can be taken from textbooks and the scientific literature listed on the website hypertext transfer protocol://world wide web.genome.jp/kegg/metabolism.hypertext markup language, wherein "hypertext transfer protocol"=http, "world wide web"=www, and "hypertext markup language"=html. In particular, a methionine pathway within the meaning of the present invention is shown in FIG. 1.

The term "yield of homolanthionine" describes the yield of homolanthionine which is calculated as the amount of homolanthionine obtained per weight cell mass.

Reducing and/or preventing the formation and/or accumulation of homolanthionine in the methionine pathway means that homolanthionine is produced with an efficiency and/or yield and/or amount of preferably less than 90%, less than 70%, less than 50%, less than 30%, less than 25%, less than 20%, less than 15%, less than 10%, less than 5% or less than 2% compared to the efficiency and/or yield and/or amount in a methionine-producing microorganism in which the activity of enzymes of the methionine pathway such as MetB, MetC, MetZ, Met E and/or MetH is not altered in accordance with the present invention.

The definitions as given above with respect to methionine and homolanthionine apply correspondingly for other metabolites of the methionine pathway.

The term "organism" or "microorganism" for the purposes of the present invention refers to any organism that is commonly used of the production of amino acids such as methionine. In particular, the term "organism" relates to prokaryotes, lower eukaryotes and plants. A preferred group of the above-mentioned organisms comprises actino bacteria, cyano bacteria, proteo bacteria, *Chloroflexus aurantiacus*, *Pirelluta* sp, l, halo bacteria and/or methanococci, preferably coryneform bacteria, myco bacteria, *streptomyces*, *salmonella*, *Escherichia coli*, *Shigella* and/or *Pseudomonas*. Particularly preferred microorganisms are selected from *Corynebacterium glutamicum*, *Escherichia coli*, microorganisms of the genus *Bacillus*, particularly *Bacillus subtilis*, and microorganisms of the genus *Streptomyces*.

The organisms of the present invention may, however, also comprise yeasts such as *Schizosaccharomyces pombe* or cerevisiae and *Pichia pastoris*.

The term "L-methionine-overproducing microorganism" for the purposes of the present invention refers to a microorganism in which, compared to a wild-type microorganism, the efficiency and/or yield and/or amount of methionine production is increased by at least 100%, at least 200%, at least 300%, at least 400%, at least 500%, at least 600%, at least 700%, at least 800%, at least 900% or at least 1000% or more.

Plants are also considered by the present invention for the production of microorganisms. Such plants may be monocots or dicots such as monocotyledonous or dicotyledonous crop plants, food plants or forage plants. Examples for monocotyledonous plants are plants belonging to the genera of *avena* (oats), *triticum* (wheat), *secale* (rye), *hordeum* (barley), *oryza* (rice), *panicum, pennisetum, setaria, sorghum* (millet), *zea* (maize) and the like.

Dicotyledonous crop plants comprise inter alia cotton, leguminoses like pulse and in particular alfalfa, soy bean, rapeseed, tomato, sugar beet, potato, ornamental plants as well as trees. Further crop plants can comprise fruits (in particular apples, pears, cherries, grapes, citrus, pineapple and bananas), oil palms, tea bushes, cacao trees and coffee trees, tobacco, sisal as well as, concerning medicinal plants, rauwolfia and digitalis. Particularly preferred are the grains wheat, rye, oats, barley, rice, maize and millet, sugar beet, rapeseed, soy, tomato, potato and tobacco. Further crop plants can be taken from U.S. Pat. No. 6,137,030.

The term "wild type organism" or "wild type microorganism" relates to an organism that has not been genetically modified.

The term "metabolite" refers to chemical compounds that are used in the metabolic pathways of organisms as precursors, intermediates and/or end products. Such metabolites may not only serve as chemical building units, but may also exert a regulatory activity on enzymes and their catalytic activity. It is known from the literature that such metabolites may inhibit or stimulate the activity of enzymes (Stryer, Biochemistry, (1995) W.H. Freeman & Company, New York, N.Y.).

For the purposes of the present invention, the term "external metabolite" comprises substrates such as glucose, sulfate, thiosulfate, sulfite, sulfide, ammonia, oxygen etc. In certain embodiments (external) metabolites comprise so called C1-metabolites. The latter metabolites can function as e.g. methyl donors and comprise compounds such as formate, formaldehyde, methanol, methanethiol, dimethyl-disulfide etc.

The term "products" comprises methionine, biomass, $CO_2$, etc.

Amino acids comprise the basic structural units of all proteins, and as such are essential for normal cellular functioning in organisms. The term "amino acid" is well known in the art. The proteinogenic amino acids, of which there are 20 species, serve as structural units for proteins, in which they are linked by peptide bonds, while the non-proteinogenic amino acids are not normally found in proteins (see Ullmann's Encyclopaedia of Industrial Chemistry, Vol. A2, pages 57-97, VCH, Weinheim (1985)). Amino acids may be in the D- or L-optical configuration, although L-amino acids are generally the only type found in naturally-occurring proteins. Biosynthetic and degradative pathways of each of the 20 proteinogenic amino acids have been well characterized in both prokaryotic and eukaryotic cells (see, for example, Stryer, L. Biochemistry, 3rd edition, pages 578-590 (1988)). The essential amino acids, i.e. histidine, isoleucine, leucine, lysine, methionine, phenylalanine, threonine, tryptophan and valine, which are generally a nutritional requirement due to the complexity of their biosynthesis, are readily converted by simple biosynthetic pathways to the remaining 11 non-essential amino acids, i.e. alanine, arginine, asparagine, aspartate, cysteine, glutamate, glutamine, glycine, proline, serine and tyrosine. Higher animals do retain the ability to synthesize some of these amino acids, but the essential amino acids must be supplied from the diet in order for normal protein synthesis to occur. Apart from their function in protein bio-synthesis, these amino acids are interesting chemicals in their own right, and many have been found to have various applications in the food, feed, chemical, cosmetic, agricultural and pharmaceutical industries. Lysine is an important amino acid in the nutrition not only of humans, but also of monogastric animals, such as poultry and swine. Glutamate is most commonly used as a flavour additive, and is widely used throughout the food industry as are aspartate, phenylalanine, glycine and cysteine. Glycine, L-methionine and tryptophan are all utilized in the pharmaceutical industry.

Glutamine, valine, leucine, isoleucine, histidine, arginine, proline, serine and alanine are of use in both the pharmaceutical and cosmetic industries. Threonine, tryptophan and D/L-methionine are common feed additives (Leuchtenberger, W. (1996), Amino acids—technical production and use, p. 466-502 in Rehm et al. (editors) Biotechnology, Vol. 6, Chapter 14a, VCH: Weinheim). Additionally, these amino acids have been found to be useful as precursors for the synthetic of synthetic amino acids and proteins such as N-acetyl cysteine, S-carboxymethyl-L-cysteine, (S)-5-hydroxytryptophan and others described in Ullmann's Encyclopaedia of Industrial Chemistry, Vol. A2, p. 57-97, VCH: Weinheim, 1985.

The biosynthesis of these natural amino acids in organisms capable of producing them, such as bacteria, has been well characterized (for review of bacterial amino acid biosynthesis and regulation therefor (see Umbarger H. E. (1978), Ann. Rev. Biochem. 47:533-606). Glutamate is synthesized by the reductive amination of α-ketoglutarate, an intermediate in the citric acid cycle. Glutamine, proline and arginine are each subsequently produced from glutamate. The biosynthesis of serine is a three-step process beginning with 3-phosphoglycerate (an intermediate in glycolysis), and resulting in this amino acid after oxidation, transamination, and hydrolysis steps. Both cysteine and glycine are produced from serine; the former by the condensation of homocysteine with serine, and the latter by transferal of the side-chain β-carbon atom to tetrahydrofolate, in a reaction catalysed by serine transhydroxymethylase. Phenylalanine and tyrosine are synthesized from the glycolytic and pentose phosphate pathway precursors erythrose-4-phosphate and phosphoenolpyruvate in a nine-step biosynthetic pathway that differ only at the final two steps after the synthesis of prephenate. Tryptophan is also produced from these two initial molecules, but its synthesis is an eleven-step pathway. Tyrosine may also be synthesized from phenylalanine in a reaction catalysed by phenylalanine hydroxylase. Alanine, valine and leucine are all biosynthetic products of pyruvate, the final product of glycolysis. Aspartate is formed from oxaloacetate, an intermediate of the citric acid cycle. Asparagine, methionine, threonine and lysine are each produced by the conversion of aspartate. Isoleucine may be formed from threonine. A complex nine-step pathway results in the production of histidine from 5-phosphoribosyl-1-pyrophosphate, an activated sugar.

Amino acids in excess of the protein synthesis needs of the cell cannot be stored and are instead degraded to provide intermediates for the major metabolic pathways of the cell (for review see Stryer, L., Biochemistry, 3rd edition, Chapter 21 "Amino acid degradation and the urea cycle", p. 495-516 (1988)). Although the cell is able to convert unwanted amino acids into useful metabolic intermediates, amino acid production is costly in terms of energy, precursor molecules, and the enzymes necessary to synthesise them. Thus, it is not surprising that amino acid biosynthesis is regulated by feedback inhibition, in which the presence of a particular amino acid serves to slow or entirely stop its own production (for overview of feedback mechanisms in amino acid biosynthetic pathways, see Stryer, L., Biochemistry, 3rd edition, Chapter 24: "Biosynthesis of amino acids and heme", p. 575-600 (1988)). Thus, the output of any particular amino acid is limited by the amount of that amino acid present in the cell.

The Gram-positive soil bacterium Corynebacterium glutamicum is widely used for the industrial production of different amino acids. Whereas the biosynthesis of lysine and glutamate, the main industrial products, has been studied for many years knowledge about the regulation of the methionine biosynthetic pathway is limited. At least the key enzymes of the pathway are known (see FIG. 1). C. glutamicum activates homoserine by acetylation with homoserine-O-acetyltransferase (MetA) (EC 2.3.1.31). It was further shown that both transsulfuration and direct sulfhydrylation are used to produce homocysteine (Hwang, B. J., Yeom, H. J., Kim, Y., Lee, H. S., J. Bacteriol. 2002, 1845, 1277-86). Transsulfuration is catalyzed by cystathionine-γ-synthase (MetB) (EC 2.5.1.48) (Hwang, B. J., Kim, Y., Kim, H. B., Hwang, H. J., Kim, J. H., Lee, H. S., Mol Cells 1999, 93, 300-8). In this reaction, cysteine and O-acetyl-homoserine are combined to cystathionine, which is hydrolyzed by the cystathionine-β-lyase (MetC which is also known as AecD) (EC 4.4.1.8) (Kim, J. W., Kim, H. J., Kim, Y., Lee, M. S., Lee, H. S., Mol Cells 2001, 112, 220-5; Ruckert et al., 2003, vide supra) to homocysteine, pyruvate and ammonia. In the direct sulfhydrylation O-acetylhomoserine sulfhydrolase (MetZ which is also known as MetY) (EC 2.5.1.49) (Ruckert et al., 2003, vide supra) converts O-acetylhomoserine and sulfide into homocysteine and acetate. Finally, C. glutamicum has two different enzymes for the S-methylation of homocysteine yielding methionine (Lee, H. S., Hwang, B. J., Appl. Microbiol. Biotechnol. 2003, 625-6, 459-67; Ruckert et al., 2003, vide supra), i.e. a cob(I)alamin dependent methionine synthase I (MetH) (EC 2.1.1.13) and a cob(I)alamin independent methionine synthase II (MetE) (EC 2.1.1.14). The former utilizes 5-methyltetrahydrofolate and the latter 5-methyltetrahydropteroyltri-L-glutamate as the methyl donor.

Recently, a putative transcriptional regulator protein of the TetR-family was found (Rey et al., Journal of Biotechnology 2003, 103, 51-65). This regulator was shown to repress the transcription of several genes belonging to methionine and sulfur metabolism. The gene knockout of the regulator protein led to an increased expression of hom encoding homoserine dehydrogenase, metZ encoding O-acetylhomoserine sulfhydrolase, metK encoding S-adenosylmethionine (SAM) synthase (EC 2.5.1.6), cysK encoding cysteine synthase (EC 2.5.1.47), cysI encoding a putative NADPH dependant sulfite reductase, and finally ssuD encoding an putative alkanesulfonate monooxygenase. Rey et al. (Molecular Microbiology 2005, 56, 871-887) also found that the metB gene is significantly induced in a mcbR minus strain.

The present invention is based, at least in part, on the discovery that reducing and/or preventing the formation of homolanthionine, in particular reducing and/or preventing the formation and/or accumulation of homolanthionine in the methionine pathway, may increase the efficiency of synthesis and/or yield of desirable compounds such as L-methionine in the microorganism.

The formation and/or accumulation of homolanthionine in the methionine pathway may be reduced and/or prevented by reducing the efficiency and/or yield of or by suppressing the MetB-catalyzed conversion of O-acetyl-homoserine and homocysteine to homolanthionine. Reducing the efficiency or suppressing the MetB-catalyzed conversion of O-acetyl-homoserine and homocysteine to homolanthionine means that homolanthionine is produced with an efficiency and/or yield and/or amount of less than 90%, less than 70%, less than 50%, less than 30%, less than 25%, less than 20%, less than 15%, less than 10%, less than 5% or less than 2% compared to the efficiency and/or yield and/or amount in a methionine-producing microorganism in which the activity of MetB is not altered.

In addition or alternatively, the formation and/or accumulation of homolanthionine in the methionine pathway may be reduced and/or prevented by increasing the efficiency and/or yield of the MetC-catalyzed cleavage of homolanthionine with water to homocysteine, 2-oxobutanoate and $NH_4^+$. Increasing the efficiency of the MetC-catalyzed cleavage of homolanthionine with water to homocysteine, 2-oxobutanoate and $NH_4^+$ means that the efficiency and/or yield and/or amount of homocysteine production from homolanthionine is increased by at least 40%, at least 45%, at least 50%, at least 55%, at least 60%, at least 65%, at least 70%, at least 75%, at least 80%, at least 85%, at least 90%, at least 95% or at least 98% compared to the efficiency and/or yield and/or amount in a methionine-producing microorganism in which the activity of MetB and/or MetC is not altered.

The efficiency and/or yield of synthesis of L-methionine in the microorganism may be even further increased if the content and/or the biological activity of the transcriptional regulator protein McbR is reduced compared to the wild type micro-organism. Hence, it one aspect of the present invention, microorganisms are provided in which the content and/or the biological activity of the transcriptional regulator protein McbR is reduced compared to the wild type microorganism, and wherein the formation of homolanthionine in the methionine pathway is prevented.

The knockout of the transcriptional regulator McbR in microorganisms such as Corynebacterium glutamicum has severe consequences for cellular metabolism. For example, the knockout of the transcriptional repressor McbR in Corynebacterium glutamicum has strong impact on the cellular metabolism. The phenotype includes reduced growth, reduced biomass yield and intracellular accumulation of methionine precursors such as cysteine and homocysteine. Interestingly, no methionine accumulation could be observed. However, is has been found in the context of the present invention that the knockout of McbR also leads to the accumulation of homolanthionine and to a threonine independent isoleucine synthesis.

Homolanthionine accumulation by other organisms has been described in previous studies. A methionine auxotrophic strain of E. coli accumulates large amounts of homolanthionine (Huang, H. T., Biochemistry 1963, 2, 296-8). Also, methionine auxotrophic Aspergillus nidulans accumulates homolanthionine (Paszewski, A., Grabski, J., Acta Biochim. Pol. 1975, 223, 263-8). Common for both organisms investigated was a knockout of the methionine synthase. But also the human liver cystathionase can accumulate homolanthionine (Tallan, H. H. et al., Biochem Biophys Res Commun 1971, 432, 303-10). Additionally, cystathionase of Streptomyces phaeochromogenes was used for in vitro synthesis of homolanthionine (Kanzaki, H. et al., Agric Biol Chem 1986, 502, 391-397) and cystathionine-γ-synthase from Arabidopsis thaliana produced homolanthionine from homocysteine and O-acetyl-homoserine in vitro (Ravanel, S. et al., Biochem J 1998, 331 (Pt 2), 639-48).

Figure 3:
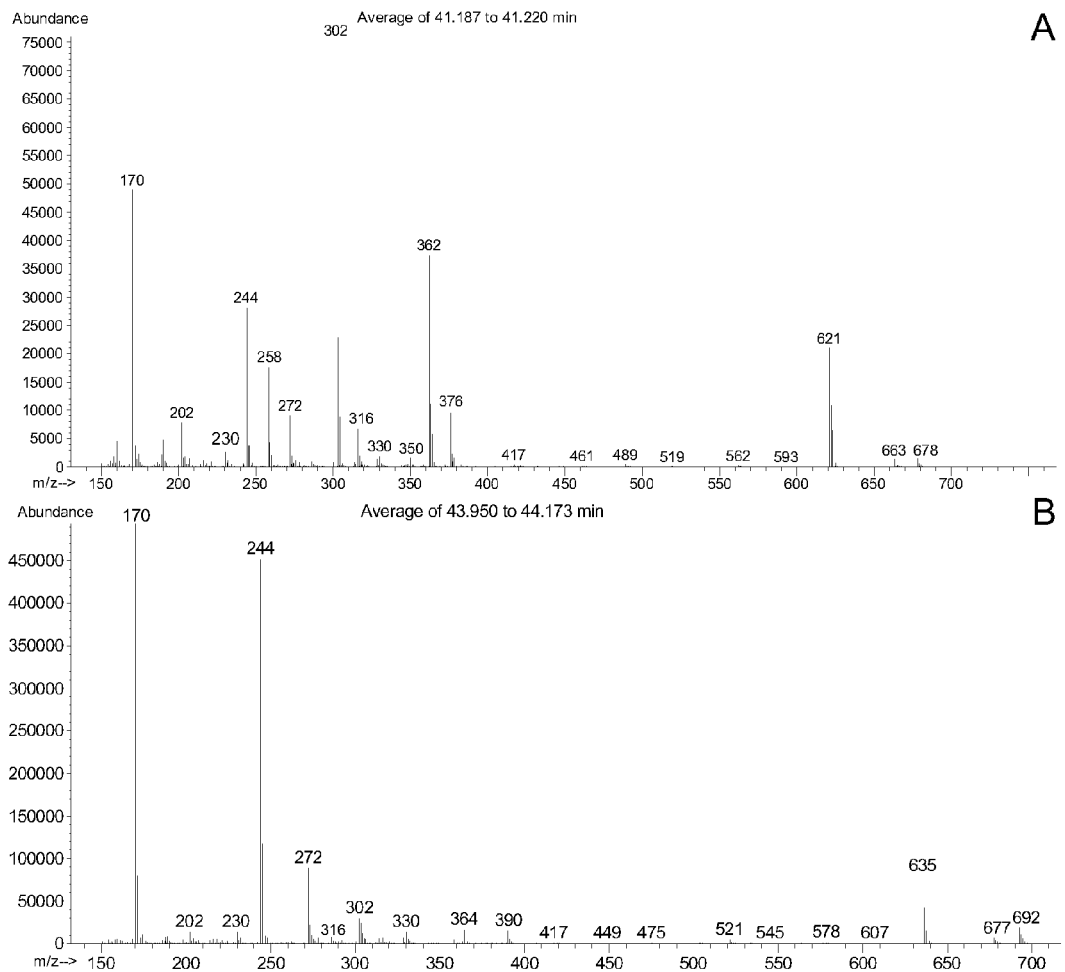
FIG. 3 depicts a GC/MS mass spectrum of MBDSTFA-derivatized cystathionine (A) and homolanthionine (B).

For an organism such as C. glutamicum it has now been found that the formation of homolanthionine (see FIG. 3) is a side reaction of MetB due to the high intracellular homocysteine levels. Due to low substrate specificity and elevated homocysteine titers, MetB accidentally uses homocysteine instead of cysteine as a substrate together with O-acetyl-homoserine. This reaction yields homolanthionine instead of cystathionine. The poor cleavage of homolanthionine by MetC leads to a tremendous accumulation of homolanthionine.

The elevated homocysteine level, especially in the McbR-knockout strains (which are also designated as C. glutamicum ΔMcbR strains), may be caused by overexpression of homoserine dehydrogenase (Hom), O-acetylhomoserine sulfhydrolase (MetZ) and S-adenosylmethionine synthase (MetK) (Rey et al., 2003, vide supra). Hom and MetZ probably lead to a direct increase of homocysteine titers, whereas MetK converts methionine to SAM which is then converted via S-adenosyl homocysteine back to homocysteine. Besides the elevated homocysteine level the homolanthionine formation is favored by an overexpression of MetB in McbR knockout strains. It has now been shown that crude extracts of McbR knockout strains may exhibit an almost 3fold MetB activity compared to the wild type.

To confirm that homolanthionine is formed in C. glutamicum by a side reaction of MetB was knocked out in C. glutamicum ΔMcbR. Supporting our findings, the knockout of MetB completely prevented the homolanthionine accumulation in C. glutamicum ΔMcbR. The slow cleavage of homolanthionine by MetC leads to an open metabolic cycle where homocysteine is recycled but O-acetyl-homoserine is converted to acetate, 2-oxobutanoate and ammonia. This cycle not only wastes acetyl-CoA but supplies an important isoleucine precursor. 2-oxobutanoate. This enables ΔMcbR strains to synthesize isoleucine via a threonine independent route.

Hence, according to another embodiment of the present invention the formation and/or accumulation of homolanthionine in the methionine pathway of a microorganism is reduced and/or prevented by reducing the content and/or the biological activity of cystathionine-γ-synthase (MetB) compared to the wild type microorganism. The content and/or the biological activity of cystathionine-γ-synthase (MetB) may be reduced compared to the wild type microorganism by attenuating and/or disrupting and/or eliminating a gene which codes for MetB. In particular, the disrupted MetB gene in the microorganism according to the present invention prevents the expression of a functional MetB protein. As is shown in the examples, the knockout of MetB completely prevents the homolanthionine accumulation in microorganisms such as *Corynebacterium glutamicum* and *C. glutamicum* ΔMcbR.

Further, the formation of homolanthionine in the methionine pathway may be reduced and/or prevented by introducing a heterologous gene coding for a cystathionine-β-lyase (MetC) mutant which is capable of efficiently converting homolanthionine into homocysteine.

A cystathionine-β-lyase (MetC) mutant which is capable of efficiently converting homolanthionine into homocysteine is characterized in that the efficiency and/or yield and/or amount of homocysteine production from homolanthionine is increased by at least 40%, at least 45%, at least 50%, at least 55%, at least 60%, at least 65%, at least 70%, at least 75%, at least 80%, at least 85%, at least 90%, at least 95% or at least 98% compared to the efficiency and/or yield and/or amount in a methionine-producing microorganism in which the activity of MetB and/or MetC is not altered.

The accumulation of homocysteine and cysteine could be regarded as beneficial for methionine overproduction, in particular if the accumulated homocysteine is further metabolized to methionine catalyzed by the activities of metH and/or metE.

Further, the formation of homolanthionine in the methionine pathway may be reduced and/or prevented by introducing a heterologous gene coding for a cystathionine-γ-synthase (MetB) mutant which is capable of efficiently converting O-acetyl-homoserine and cysteine into cystathione and which is not capable of converting O-acetyl-homoserine and homocysteine into homolanthionine.

A cystathionine-γ-synthase (MetB) mutant which is capable of efficiently converting O-acetyl-homoserine and cysteine into cystathione is characterized in that the efficiency and/or yield and/or amount of cystathione production from cysteine and O-acetyl-homoserine is increased by at least 40%, at least 45%, at least 50%, at least 55%, at least 60%, at least 65%, at least 70%, at least 75%, at least 80% or at least 85%, at least 90%, at least 95%, or at least 98% compared to the efficiency and/or yield and/or amount in a methionine-producing microorganism in which the activity of MetB is not altered.

A cystathionine-γ-synthase (MetB) mutant which is not capable of converting O-acetyl-homoserine and homocysteine into homolanthionine is characterized in that homolanthionine is produced with an efficiency and/or yield and/or amount of less than 70%, less than 50%, less than 30%, less than 25%, less than 20%, less than 15%, less than 10% or less than 5% compared to the efficiency and/or yield and/or amount in a methionine-producing microorganism in which the activity of MetB is not altered.

According to a further embodiment of the present invention, a microorganism is provided wherein the content and/or the biological activity of a protein selected from the group consisting of O-acetyl-homoserine sulfhydrolase (MetZ), cob(I)alamin dependent methionine synthase I (MetH) and cob(I)alamin independent methionine synthase II (MetE) is enhanced and/or over-expressed compared to the wild type microorganism.

Increasing or decreasing the content or amount and/or biological activity of an enzyme has to be understood with respect to the direction in which the reaction should be further pushed or channeled. Increasing the content and/or biological activity of an enzyme or decreasing the content and/or biological activity of an enzyme are understood to influence the amount and/or activity of the enzyme in such a way that more or less product according to the pathway shown in FIG. 1 is obtained.

In one embodiment of the invention it may be sufficient to modify the amount and/or activity of only one enzyme of the methionine pathway. Alternatively, the amount and/or activity of various enzymes of this metabolic pathway may be modified. Alternatively, the amount and/or activity of various or all enzymes the methionine pathway may be influenced at the same time. How such organisms can be obtained by genetic modification belongs to the general knowledge in the art.

In the following table specific examples are given for enzymes of the methionine pathway whose content and/or biological activity may be modified in order to increase the efficiency of methionine synthesis.

TABLE 1

| Name | Enzyme | Gene bank accession number | Organism |
|---|---|---|---|
| MetA | homoserine O-acetyltransferase | Cgl0652, cg0754, CE0678, DIP0623, jk1695, nfa9220, MAP3458, ML0682, Mb3373, Rv3341, MT3444, Tfu__2822, Lxx18950, CT0605, blr1399, STH1685, CC0525, ZMO0225, RPA4437, MA2714, GOX0203, mlr3538, DP1243, LIC11853, LA2061, BPP4083, BP0047, BB4554, GSU2462, BMA3246, BPSL0197, SAR11__0217, ebA2806, VNG2420G, Daro__0130, CV0786, AFR682C, HI1263, RB8222, NGO0933, LMOf2365__0623, RSc0027, lmo0594, NTHI1901, lin0603, YNL277W, NMB0940, MS0924, orf19.2618, rmAC3064, PD1484, NMA1136, PM0866, TTC0407, TTHA0759, XF2465, NE2186, PSPPH__0465, PSPTO5049, SPBC56F2.11, Psyr__0474, XC__1889, XCC2228, PP5097, PFL__5842, ACIAD0529, XOO2093, PA0390, XAC2332, CNE02740, WS1893, Psyc__0375, DR0872, IL2157, BA4983, BAS4629, GBAA4983, BC4730, BCZK4482, BT9727__4463, BCE4873, SAR0012, SACOL0012, MW0012, SAS0012, SA0011, SAV0012, SH0011, SE0011, SERP2541, MTH1820, gll2500, BA__5402 | *C. glutamicum* and others |
| MetB | cystathionine-γ-synthase | Cgl2446, cg2687, CE2343, jk0055, nfa48270, MAP1026, Mb1108, MT1110, Rv1079, ML2394, SCO4958, SAV3305, Tfu__0440, Lxx03230, BL1155, Bd3795, IL0219, VNG1172G, XAC3602, CV4049, EF0290, XOO0778, XC__3635, XCC0598, L0181, PA0400, lpl0921, DDB0191318, CBU2025, lpg0890, lpp0951, plu0523, mll4503, APE1226, BG12291, OB1109, CAC0930, BLi02853, BL02018, CT0701, YAL012W, CG5345-PA, ZK1127.10, GK2540, AEL341W, HP0106, CMT389C, FN1419, 1491, BCZK4116, BCE4454, BC4366, | *C. glutamicum* and others |

TABLE 1-continued

| Name | Enzyme | Gene bank accession number | Organism |
|---|---|---|---|
| | | BH0799, str0847, stu0847, jhp0098, BT9727_4105, BA4600, GBAA4600, BAS4268, 107869, BA__5041, orf19.6402, SH2548, MA2532, SE2323, SERP0095, lp__0255, HH0062, RPA2357, CPE0176, STH832, SO4056, SPOA0318, rrnAC2414, CTC02530, SA0419, TDE2200, SACOL0503, MW0415, SAS0418, MM3085, lmo1679, LMOf2365__1703, SAR0460, PFL__3514, lin1787, PP1308, CPS__0455, PG0343, TTE1574, PBPRA0261, ABC1945, PD1812, GSU0944, XF0864, t3518, STY3769, DR0921, SC3991, STM4100, VP2765, CC3168, YP0117, YPTB0105, VV11364, RB6443, ECA4252, HI0086, Z5494, ECs4868, SPA3943, VF2267, VC2683, NTHI0100, PMT0226, JW3910, b3939, NMB0802, SF4017, S3730, NGO0386, MS1627, VV3008, PM0995, NMA1012, SYNW0675, M6__Spy0192, SpyM3__0133, spyM18__0170, SPs0136, SAV0358, SPy0172, 132.t00018, At3g57050, PMN2A__1743, PMM0409, Pro0405, BruAb1__0331, Psyr__1669, BMEI1617, BR0305, SSO2368, PSPTO3810, SMc02595, PSPPH__1663, Bfl598, Saci__0971, ACIAD2314, LBA1090, Ta0080, ST0506, PAE2420, ebA4598, NE0700, SMU.1675, MCA2488, TVN0174, TM0882, CNK01740, spr1377, SP1525, AGR__C__761, Atu0432, blr4967, ZMO0676, Psyc__0792, PTO1102, BPSS1691, BMAA1713, PH1093, PF1266, Daro__2851, DP1700, BF1406, BT2387, PAB0605 | |
| MetC | cystathionine-β-lyase | cg2536, NCgl2227, CE2211, DIP1736, Mb0077, MT0081, Rv0075, jk0592, BL1268, BG10744, OB2338, ebA3862, EF2895, PFL__3470, BLi03326, BL02532, stu0353, str0353, BT9727__4616, MAP2055, BCZK4638, CAC2970, ABC2888, gbs1636, SAG1587, BAS4776, BA__0012, GBAA5138, BA5138, BCE5045, BC4906, MCA1021, TTHA1620, TTC1256, SCO0731, GK2931, BF2133, L177593, BH3313, BT1398, BF2081, ML1794, SP1524, spr1376, YP2630, YPO3006, YPTB2726, y1475, WS0402, Daro__4129, lin2469, BF0911, BF0990, Mb2316, Rv2294, CTC00825, LMOf2365__2341, SMU.1674, lmo2370, DVU0171, SPO3220, MT2351, BT4138, TDE2410, TDE1669, DR1452, FN0625, NE2400, LJ0915, VF1253, PBPRA2148, SPA1313, STM1557, lp__2888, VV21062, 36.t00025, EF0029, plu3731, t1470, STY1507, VF1718, c1175, lp__2751, SH0221, YPTB2200, ECs2330, Z2627, SCO0435, S1779, SF1647, c2014, SSO__1536, LBA0743, JW1614, b1622, lp__3517, c3407 | C. glutamicum |
| MetE | cob(I)alamin independent methionine synthase II | Cgl1507, cg1290, CE1209, jk0234, Mb1164c, MT1165, Rv1133c, MAP2661, ML0961, SCO0985, PM0420, SAV2046, CMJ234C, NE1436, PD1308, CC0482, XF2272, RSp0676, HI1702, CV3604, NGO0928, MCA2260, At5g17920, ZMO1000, RPA2397, BB2079, BPP2636, BP2543, NMA1140, NMB0944, mll6123, BPSL2545, BMA0467, SPAC9.09, YPO3788, YP3261, y0442, YPTB0248, SF3907, S3848, PSPTO4179, SC3864, CBU2048, STM3965, JW3805, b3829, DVU3371, Z5351, ECs4759, t3332, STY3594, SPA3806, WS0269, blr2068, ECA0181, PFL__2404, plu4420, nfa52280, CNK02310, PA1927, PBPRA1379, VV12219, VF1721, VC1704, VV2135, VP1974, bbp031, BL0798, SO0818, BU030, BUsg031, SP0585, HH0852, spr0514, orf19.2551, ABR212C, str0785, stu0785, lmo1681, YER091C, BH0438, LMOf2365__1705, Bfl625, lp__1375, BLi01422, BL03738, lin1789, SMU.873, DDB0230069, BT9727__3744, ABC1449, tlr1090, BA4218, GBAA4218, BAS3912, BCE4053, BC4003, CJE1335, L0100, BA__4680, Cj1201, SA0344, SAV0356, SACOL0428, SERP0034, MW0332, SAR0353, SE2382, SAS0332, TM1286, BCZK3760, SH2638, BG12616, SAG2049, gbs2005, aq__1710, TW610, TWT162, APE2048, SSO0407, ST0385, Saci__0828, rrnAC0254, PF1269, TK1446, PAB0608, PH1089, PAE3655, Ta0977, MTH775, XC__0330, XCC0318, Psyc__0846, GOX2206, TVN1123, ACIAD3523, AGR__L__2018, Atu3823, PTO0186, XAC0336, Psyr__2855, MJ1473, PP2698, XOO4333, CPS__1151, MK0667, PSPPH__3910, MMP0401 | C. glutamicum and others |
| MetH | cob(I)alamin dependent methionine synthase I | Cgl1139, cg1701, CE1637, DIP1259, nfa31930, Rv2124c, Mb2148c, ML1307, SCO1657, Tfu__1825, SAV6667, MT2183, GOX2074, tll1027, syc0184__c, alr0308, slr0212, gll0477, SYNW1238, TTC0253, TTHA0618, PMT0729, Pro0959, PMN2A__0333, PMM0877, WS1234, BH1630, GK0716, BCE4332, ABC1869, BC4250, BCZK4005, BT9727__3995, BA__4925, GBAA4478, BA4478, BAS4156, BLi01192, BL01308, MAP1859c, BruAb1__0184, BMEI1759, BR0188, SMc03112, MCA1545, AGR__C__3907, Atu2155, DR0966, RB9857, ebA3184, VC0390, RPA3702, VV11423, VV2960, VP2717, NE1623, VF0337, LIC20085, LB108, YPTB3653, YPO3722, y0020, YP3084, CV0203, SPA4026, MS1009, SC4067, | C. glutamicum and others |

TABLE 1-continued

| Name | Enzyme | Gene bank accession number | Organism |
|---|---|---|---|
| | | SO1030, DP2202, STM4188, STY4405, t4115, PP2375, PFL_3662, Z5610, ECs4937, c4976, JW3979, b4019, SF4085, S3645, BB4456, BPP3983,BP3594, bll1418, CPS_1101, Psyr_2464, PSPTO2732, R03D7.1, PSPPH_2620, PBPRA3294, Daro_0046, PA1843, ECA3987, CT1857, CAC0578, ACIAD1045, Psyc_0403, 4548, DDB0230138, BF3039, BF3199, BT0180, 238505, GSU2921, STH2500, XC_2725, XCC1511, XOO2073, TTE1803, RSc0294, XAC1559, BPSL0385, DVU1585, CTC01806, CC2137, TM0268, ZMO1745, FN0163, BG13115, lin1786, SAG2048, gbs2004, LMOf2365_1702, lmo1678, SE2381, SERP0035, MW0333, SAS0333, SMU.874, SA0345, SAV0357, SACOL0429, SAR0354, SH2637 | |
| MetZ | O-acetylhomoserine sulfhydrolase | NCgl0625, cg0755, CE0679, DIP0630, jk1694, MAP3457, Mb3372, MT3443, Rv3340, nfa35960, Lxx18930, Tfu_2823, CAC2783, GK0284, BH2603, lmo0595, lin0604, LMOf2365_0624, ABC0432, TTE2151, BT2387, STH2782, str0987, stu0987, BF1406, SH0593, BF1342, lp_2536, L75975, OB3048, BL0933, LIC11852, LA2062, BMAA1890, BPSS0190, SMU.1173, BB1055,PP2528, PA5025, PBPRB1415, GSU1183, RPA2763, WS1015, TM0882, VP0629, BruAb1_0807, BMEI1166, BR0793, CPS_2546, XC_1090, XCC3068, plu3517, PMT0875, SYNW0851, Pro0800, CT0604, NE1697, RB8221, bll1235, syc1143_c, ACIAD3382, ebA6307, RSc1562, Daro_2851, DP2506, DR0873, MA2715, PMM0642, PMN2A_0083, IL2014, SPO1431, ECA0820, AGR_C_2311, Atu1251, mlr8465, SMc01809, CV1934, SPBC428.11, PM0738, SO1095, SAR11_1030, PFL_0498, CTC01153, BA_0514, BCE5535, BAS5258, GBAA5656, BA5656, BCZK5104, TTHA0760, TTC0408, BC5406, BT9727_5087, HH0636, YLR303W, ADL031W, CJE1895, spr1095, rrnAC2716, orf19.5645, Cj1727c, VNG2421G, PSPPH_1663, XO01390, Psyr_1669, PSPTO3810, MCA2488, TDE2200, FN1419, PG0343, Psyc_0792, MS1347, CC3168, Bd3795, MM3085, 389.t00003, NMB1609,SAV3305, NMA1808, GOX1671, APE1226, XAC3602, NGO1149, ZMO0676, SCO4958, lpl0921, lpg0890, lpp0951, EF0290, BPP2532, CBU2025, BP3528, BLi02853, BL02018, BG12291, CG5345-PA, HP0106, ML0275, jhp0098, At3g57050, 107869, HI0086, NTHI0100, SpyM3_0133, SPs0136, spyM18_0170, M6_Spy0192, SE2323, SERP0095, SPy0172, PAB0605, DDB0191318, ST0506, F22B8.6, PTO1102, CPE0176, PD1812, XF0864, SAR0460, SACOL0503, SA0419,Ta0080, PF1266, MW0415, SAS0418, SSO2368, PAE2420, TK1449, 1491, TVN0174, PH1093, VF2267, Saci_0971, VV11364, CMT389C, VV3008 | C. glutamicum and others |

By genetically amending organisms in accordance with the present invention, the efficiency and/or yield of methionine synthesis may be increased such that these methionine-overproducing organisms are characterized in that methionine is produced with an efficiency and/or yield of preferably at least 50%, at least 60%, at least 65%, at least 70%, at least 75%, at least 80% or at least 85%. Compared to a wild-type microorganism, the efficiency and/or yield and/or amount of methionine production in the methionine-overproducing organism according to the present invention is increased by preferably at least 100%, at least 200%, at least 300%, at least 400%, at least 500%, at least 600%, at least 700%, at least 800%, at least 900% or at least 10000% or more.

The microorganism according to the present invention may be selected from the group consisting of coryneform bacteria, mycobacteria, streptomycetes, *Salmonella, Escherichia coli, Shigella, Bacillus, Serratia* and *Pseudomonas*.

The organisms of the present invention may preferably comprise a microorganism of the genus *Corynebacterium*, particularly *Corynebacterium acetoacidophilum, C. acetoglutamicum, C. acetophilum, C. ammoniagenes, C. glutamicum, C. lilium, C. nitrilophilus* or *C. spec*. The organisms in accordance with the present invention also comprise members of the genus *Brevibacterium*, such as *Brevibacterium harmoniagenes, Brevibacterium botanicum, B. divaraticum, B. flavam, B. healil, B. ketoglutamicum, B. ketosoreductum, B. lactofermentum, B. linens, B. paraphinolyticum* and *B. spec*. In particular, *Corynebacterium* microorganisms may be selected from the group consisting of *Corynebacterium glutamicum* (ATCC 13032), *Corynebacterium acetoglutamicum* (ATCC 15806), *Corynebacterium acetoacidophilum* (ATCC 13870), *Corynebacterium thermoaminogenes* (FERM BP-1539), *Corynebacterium melassecola* (ATCC 17965), *Corynebacterium glutamicum* (KFCC10065), *Corynebacterium glutamicum* (DSM 17322), *Corynebacterium efficiens* (YS-314) and *Corynebacterium glutamicum* (ATCC21608).

The abbreviation KFCC means Korean Federation of Culture Collection, while the abbreviation ATCC means the American Type Strain Culture Collection. The abbreviation DSM means the German Resource Centre for Biological Material.

Microorganisms of the genus *Escherichia* may be selected from the group comprising *Escherichia coli*. Microorganisms of the genus *Salmonella* may be selected from the group comprising *Salmonella typhimurium*. In some embodiments of the present invention, the organism is selected from the group consisting of *Corynebacterium glutamicum, Escherichia coli, Saccharomyces cerevisiae* and *Bacillus subtilis*.

With respect to increasing or decreasing the content or amount and/or biological activity of an enzyme, all methods that are known in the art for increasing the amount and/or activity of a protein in a host such as the above mentioned organisms may be used.

The amount of the enzyme may be increased by expression of an exogenous version of the respective protein. Further, expression of the endogenous protein can be increased by influencing the activity of the promoter and/or enhancers element and/or other regulatory activities such as phosphorylation, sumoylation, ubiquitylation etc, that regulate the activities of the respective proteins either on a transcriptional, translational or post-translational level.

Besides, simply increasing the amount of e.g. the aforementioned enzymes, the activity of the proteins may be increased by using enzymes which carry specific mutations that allow for an increased activity of the enzyme. Such mutations may, e.g. inactivate the regions of an enzyme that are responsible for feedback inhibition. By mutating these by e.g. introducing non-conservative mutations, the enzyme does not provide for feedback regulation anymore and thus activity of the enzyme is not down-regulated if more products are produced. The mutations may be either introduced into the endogenous copy of the enzyme, or may be provided by over-expressing a corresponding mutant form of the exogenous enzyme. Such mutations may comprise point mutations, deletions or insertions. Point mutations may be conservative or non-conservative. Furthermore, deletions may comprise only two or three amino acids up to complete domains of the respective protein.

Thus, the increase of the activity and the amount of a protein may be achieved via different routes, e.g. by switching off inhibitory regulatory mechanisms at the transcription, translation, or protein level or by increase of gene expression of a nucleic acid coding for these proteins in comparison with the wild type, e.g. by inducing the endogenous metC gene or by introducing nucleic acids coding for MetC.

In one embodiment, the increase of the enzymatic activity and amount, respectively, in comparison with the wild type is achieved by an increase of the gene expression of a nucleic acid encoding such enzymes such as MetC, MetZ, MetE and MetH. Sequences may be obtained from the respective database, e.g. at NCBI (hypertext transfer protocol://world wide web.ncbi.nlm.gov, wherein "hypertext transfer protocol"=http and "world wide web"=www), EMBL (hypertext transfer protocol://world wide web.embl.org, wherein "hypertext transfer protocol"=http and "world wide web"=www), Expasy (hypertext transfer protocol://world wide web.expasy.org, wherein "hypertext transfer protocol"=http and "world wide web"=www), KEGG (hypertext transfer protocol://world wide web.genome.ad.jp/kegg/kegg.hypertext markup language, wherein "hypertext transfer protocol"=http, "world wide web"=www, and "hypertext markup language"=html) etc. Examples are given in Table 1.

In a further embodiment, the increase of the amount and/or activity of the enzymes of Table 1 is achieved by introducing nucleic acids encoding the enzymes of Table 1 into the organism, preferably C. glutamicum or E. coli.

In principle, proteins of different organisms having the enzymatic activity of the proteins listed in Table 1 can be used, if increasing the amount and/or activity is envisaged. With genomic nucleic acid sequences of such enzymes from eukaryotic sources containing introns, already processed nucleic acid sequences like the corresponding cDNAs are to be used in the case that the host organism is not capable or cannot be made capable of splicing the corresponding mRNAs. All nucleic acids mentioned in the description can be, e.g., an RNA, DNA or cDNA sequence.

In one process according to the present invention for preparing organisms with increased efficiency of methionine synthesis, a nucleic acid sequence coding for one of the above-mentioned functional or non-functional, feedback-regulated or feedback-independent enzymes is transferred to a microorganism such as C. glutamicum or E. coli., respectively. This transfer leads to an increase of the expression of the enzyme, respectively, and correspondingly to more metabolic flux through the desired reaction pathway.

According to the present invention, increasing or introducing the amount and/or the activity of a protein typically comprises the following steps:

a) production of a vector comprising the following nucleic acid sequences, preferably DNA sequences, in 5'-3'-orientation:
   a promoter sequence functional in the organisms of the invention;
   operatively linked thereto a DNA sequence coding for a protein of Table 1 or functional equivalent parts thereof;
   a termination sequence functional in the organisms of the invention;
b) transfer of the vector from step a) to the organisms of the invention such as C. glutamicum or E. coli and, optionally, integration into the respective genomes.

When functionally equivalent parts of enzymes are mentioned within the scope of the present invention, fragments of nucleic acid sequences coding for enzymes of Table 1 are meant, whose expression still lead to proteins having the enzymatic activity of the respective fall length protein.

According to the present invention, non-functional enzymes have the same nucleic acid sequences and amino acid sequences, respectively, as functional enzymes and functionally equivalent parts thereof respectively, but have, at some positions, point mutations, insertions or deletions of nucleotides or amino acids, which have the effect that the non-functional enzyme are not, or only to a very limited extent, capable of catalyzing the respective reaction. These non-functional enzymes differ from enzymes that still are capable of catalyzing the respective reaction, but are not feed-back regulated anymore. Non-functional enzymes also comprise such enzymes of Table 1 bearing point mutations, insertions, or deletions at the nucleic acid sequence level or amino acid sequence level and are not, or nevertheless, capable of interacting with physiological binding partners of the enzymes. Such physiological binding partners comprise, e.g. the respective substrates. Non-functional mutants are incapable of catalyzing a reaction which the wild type enzyme, from which the mutant is derived, can catalyze.

According to the present invention, the term "non-functional enzyme" does not comprise such genes or proteins having no essential sequence homology to the respective functional enzymes at the amino acid level and nucleic acid level, respectively. Proteins unable to catalyze the respective reactions and having no essential sequence homology with the respective enzyme are therefore, by definition, not meant by the term "non-functional enzyme" of the present invention. Non-functional enzymes are, within the scope of the present invention, also referred to as inactivated or inactive enzymes.

Therefore, non-functional enzymes of Table 1 according to the present invention bearing the above-mentioned point mutations, insertions, and/or deletions are characterized by an essential sequence homology to the wild type enzymes of Table 1 according to the present invention or functionally equivalent parts thereof.

According to the present invention, a substantial sequence homology is generally understood to indicate that the nucleic acid sequence or the amino acid sequence, respectively, of a DNA molecule or a protein, respectively, is at least 40%, preferably at least 50%, further preferred at least 60%, also preferably at least 70%, particularly preferred at least 90%, in particular preferred at least 95% and most preferably at least 98% identical with the nucleic acid sequences or the amino acid sequences, respectively, of the proteins of Table 1 or functionally equivalent parts thereof.

Identity of two proteins is understood to be the identity of the amino acids over the respective entire length of the protein, in particular the identity calculated by comparison with the assistance of the Lasergene software by DNA Star, Inc., Madison, Wis. (USA) applying the CLUSTAL method (Higgins et al., (1989), Comput. Appl. Biosci., 5 (2), 151).

Homologies can also be calculated with the assistance of the Lasergene software by DNA Star, Inc., Madison, Wis. (USA) applying the CLUSTAL method (Higgins et al., (1989), Comput, Appl. Biosci., 5 (2), 151).

Identity of DNA sequences is to be understood correspondingly.

The above-mentioned method can be used for increasing the expression of DNA sequences coding for functional or non-functional, feedback-regulated or feedback-independent enzymes of Table 1 or functionally equivalent pails thereof. The use of such vectors comprising regulatory sequences, like promoter and termination sequences are, is known to the person skilled in the art. Furthermore, the person skilled in the art knows how a vector from step a) can be transferred to organisms such as C. glutamicum or E. coli and which properties a vector must have to be able to be integrated into their genomes.

If the enzyme content in an organism such as C. glutamicum is increased by transferring a nucleic acid coding for an enzyme from another organism, like e.g. E. coli, it is advisable to transfer the amino acid sequence encoded by the nucleic acid sequence e.g. from E. coli by back-translation of the polypeptide sequence according to the genetic code into a nucleic acid sequence comprising mainly those codons, which are used more often due to the organism-specific codon usage. The codon usage can be determined by means of computer evaluations of other known genes of the relevant organisms.

According to the present invention, an increase of the gene expression and of the activity, respectively, of a nucleic acid encoding an enzyme of Table 1 is also understood to be the manipulation of the expression of the endogenous respective endogenous enzymes of an organism, in particular of C. glutamicum or E. coli. This can be achieved, e.g., by altering the promoter DNA sequence for genes encoding these enzymes. Such an alteration, which causes an altered, preferably increased, expression rate of these enzymes can be achieved by deletion or insertion of DNA sequences.

An alteration of the promoter sequence of endogenous genes usually causes an alteration of the expressed amount of the gene and therefore also an alteration of the activity detectable in the cell or in the organism.

Furthermore, an altered and increased expression, respectively, of an endogenous gene can be achieved by a regulatory protein, which does not occur in the transformed organism, and which interacts with the promoter of these genes. Such a regulator can be a chimeric protein consisting of a DNA binding domain and a transcription activator domain, as e.g. described in WO 96/06166.

A further possibility for increasing the activity and the content of endogenous genes is to up-regulate transcription factors involved in the transcription of the endogenous genes, e.g. by means of overexpression. The measures for overexpression of transcription factors are known to the person skilled in the art and are also disclosed for the enzymes of Table 1 within the scope of the present invention.

Furthermore, an alteration of the activity of endogenous genes can be achieved by targeted mutagenesis of the endogenous gene copies.

An alteration of the endogenous genes coding for the enzymes of Table 1 can also be achieved by influencing the post-translational modifications of the enzymes. This can happen e.g. by regulating the activity of enzymes like kinases or phosphatases involved in the post-translational modification of the enzymes by means of corresponding measures like overexpression or gene silencing.

In another embodiment, an enzyme may be improved in efficiency, or its allosteric control region destroyed such that feedback inhibition of production of the compound is prevented. Similarly, a degradative enzyme may be deleted or modified by substitution, deletion, or addition such that its degradative activity is lessened for the desired enzyme of Table 1 without impairing the viability of the cell. In each case, the overall yield or rate of production of one of these desired fine chemicals may be increased.

It is also possible that such alterations in the protein and nucleotide molecules of Table 1 may improve the production of fine chemicals other than methionine such as other sulfur containing compounds like cysteine or glutathione, other amino acids, vitamins, cofactors, nutraceuticals, nucleotides, nucleosides, and trehalose. Metabolism of any one compound is necessarily intertwined with other biosynthetic and degradative pathways within the cell, and necessary cofactors, intermediates, or substrates in one pathway are likely supplied or limited by another such pathway. Therefore, by modulating the activity of one or more of the proteins of Table 1, the production or efficiency of activity of another fine chemical biosynthetic or degradative pathway besides those leading to methionine may be impacted.

Enzyme expression and function may also be regulated based on the cellular levels of a compound from a different metabolic process, and the cellular levels of molecules necessary for basic growth, such as amino acids and nucleotides, may critically affect the viability of the microorganism in large-scale culture. Thus, modulation of an amino acid biosynthesis enzymes of Table 1 such that they are no longer responsive to feedback inhibition or such that they are improved in efficiency or turnover should result in higher metabolic flux through pathways of methionine production.

These aforementioned strategies for increasing or introducing the amount and/or activity of the enzymes of Table 1 are not meant to be limiting; variations on these strategies will be readily apparent to one of ordinary skill in the art.

For decreasing or suppressing or reducing the amount or content and/or activity of any of enzymes of Table 1, various strategies are also available.

The expression of the endogenous enzymes of Table 1 can e.g. be regulated via the expression of aptamers specifically binding to the promoter sequences of the genes. Depending on the aptamers binding to stimulating or repressing promoter regions, the amount and thus, in this case, the activity of the enzymes of Table 1 is increased or reduced.

Aptamers can also be designed in a way as to specifically bind to the enzymes themselves and to reduce the activity of the enzymes by e.g. binding to the catalytic center of the respective enzymes. The expression of aptamers is usually achieved by vector-based overexpression (see above) and is, as well as the design and the selection of aptamers, well known to the person skilled in the art (Famulok et al., (1999) Curr Top Microbiol Immunol., 243, 123-36).

Furthermore, a decrease of the amount and the activity of the endogenous enzymes of Table 1 can be achieved by means of various experimental measures, which are well known to the person skilled in the art. These measures are usually summarized under the term "gene silencing" or "attenuating a gene" or "disrupting a gene" or "eliminating a gene". For example, the expression of an endogenous gene can be silenced by transferring an above-mentioned vector, which has a DNA sequence coding for the enzyme or parts thereof in antisense order, to the organisms such as C. glutamicum and E. coli. This is based on the fact that the transcription of such a vector in the cell leads to an RNA, which can hybridize with the mRNA transcribed by the endogenous gene and therefore prevents its translation.

Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, Reviews—Trends in Genetics, Vol. 1 (1), 1986.

In principle, the antisense strategy can be coupled with a ribozyme method. Ribozymes are catalytically active RNA sequences, which, if coupled to the antisense sequences, cleave the target sequences catalytically (Tanner et al., (1999) FEMS Microbiol Rev. 23 (3), 257-75). This can enhance the efficiency of an antisense strategy.

In plants, gene silencing may be achieved by RNA interference or a process that is known as co-suppression.

Further methods are the introduction of nonsense mutations into the endogenous gene by means of introducing RNA/DNA oligonucleotides into the organism (Zhu et al., (2000) Nat. Biotechnol. 18 (5), 555-558) or generating knockout mutants with the aid of homologous recombination (Hohn et al., (1999) Proc. Natl. Acad. Sci. USA. 96, 8321-8323).

To create a homologous recombinant microorganism, a vector is prepared which contains at least a portion of gene coding for an enzyme of Table 1 into which a deletion, addition or substitution has been introduced to thereby alter, e.g., functionally disrupt, the endogenous gene.

Preferably, this endogenous gene is a C. glutamicum or E. coli gene, but it can be a homologue from a related bacterium or even from a yeast or plant source. In one embodiment, the vector is designed such that, upon homologous recombination, the endogenous gene is functionally disrupted, i.e., no longer encodes a functional protein which is also referred to as a "knock out" vector. Alternatively, the vector can be designed such that, upon homologous recombination, the endogenous gene is mutated or otherwise altered but still encodes functional protein (e.g., the upstream regulatory region can be altered to thereby alter the expression of the endogenous enzyme of Table 1). In the homologous recombination vector, the altered portion of the endogenous gene is flanked at its 5' and 3' ends by additional nucleic acid of the endogenous gene to allow for homologous recombination to occur between the exogenous gene carried by the vector and an endogenous gene in the (micro)organism. The additional flanking endogenous nucleic acid is of sufficient length for successful homologous recombination with the endogenous gene. Typically, several hundred bases to kilobases of flanking DNA (both at the 5' and 3' ends) are included in the vector (see e.g., Thomas, K. R., and Capeechi, M. R. (1987) Cell 51: 503 and Schäfer et al. Gene. 1994 145-69-73. for descriptions of homologous recombination vectors).

The vector is introduced into a microorganism (e.g., by electroporation) and cells in which the introduced endogenous gene has homologously recombined with the endogenous enzymes of Table 1 are selected, using art-known techniques.

In another embodiment, an endogenous gene for the enzymes of Table 1 in a host cell is disrupted (e.g., by homologous recombination or other genetic means known in the art) such that expression of its protein product does not occur. In another embodiment, an endogenous or introduced gene of enzymes of Table 1 in a host cell has been altered by one or more point mutations, deletions, or inversions, but still encodes a functional enzyme. In still another embodiment, one or more of the regulatory regions (e.g., a promoter, repressor, or inducer) of an endogenous gene for the enzymes of table 1 in a (micro)organism has been altered (e.g., by deletion, truncation, inversion, or point mutation) such that the expression of the endogenous gene is modulated. One of ordinary skill in the art will appreciate that host cells containing more than one of the genes coding for the enzyme of Table 1 and protein modifications may be readily produced using the methods of the invention, and are meant to be included in the present invention.

Furthermore, a gene repression (but also gene overexpression) is also possible by means of specific DNA-binding factors, e.g. factors of the zinc finger transcription factor type. Furthermore, factors inhibiting the target protein itself can be introduced into a cell. The protein-binding factors may e.g. be the above mentioned aptamers (Famulok et al., (1999) Curr Top Microbiol Immunol. 243, 123-36).

Further protein-binding factors, whose expression in organisms cause a reduction of the amount and/or the activity of the enzymes of table 1, may be selected from enzyme-specific antibodies. The production of monoclonal, polyclonal, or recombinant enzyme-specific antibodies follows standard protocols (Guide to Protein Purification, Meth. Enzymol. 182, pp. 663-679 (1990), M. P. Deutscher, ed.). The expression of antibodies is also known from the literature (Fiedler et al., (1997) Immunotechnology 3, 205-216; Maynard and Georgiou (2000) Annu. Rev. Biomed. Eng. 2, 339-76).

The mentioned techniques are well known to the person skilled in the art. Therefore, it is also well-known which sizes the nucleic acid constructs used for e.g. antisense methods must have and which complementarity, homology or identity, the respective nucleic acid sequences must have. The terms complementarity, homology, and identity are known to the person skilled in the art.

Within the scope of the present invention, sequence homology and homology, respectively, are generally understood to mean that the nucleic acid sequence or the amino acid sequence, respectively, of a DNA molecule or a protein, respectively, is at least 40%, preferably at least 50%, further preferred at least 60%, also preferably at least 70%, particularly preferred at least 90%, in particular preferred at least 95% and most preferably at least 98% identical with the nucleic acid sequences or amino acid sequences, respectively, of a known DNA or RNA molecule or protein, respectively. Herein, the degree of homology and identity, respectively, refers to the entire length of the coding sequence.

The term "complementarity" describes the capability of a nucleic acid molecule of hybridizing with another nucleic acid molecule due to hydrogen bonds between two complementary bases. The person skilled in the art knows that two nucleic acid molecules do not have to have a complementarity of 100% in order to be able to hybridize with each other. A nucleic acid sequence, which is to hybridize with another nucleic acid sequence, is preferred being at least 40%, at least 50%, at least 60%, preferably at least 70%, particularly preferred at least 80%, also particularly preferred at least 90%, in particular preferred at least 95% and most preferably at least 98 or 100%, respectively, complementary with said other nucleic acid sequence.

Nucleic acid molecules are identical, if they have identical nucleotides in identical 5'-3'-order.

The hybridization of an antisense sequence with an endogenous mRNA sequence typically occurs in vivo under cellular conditions or in vitro. According to the present invention, hybridization is carried out in vivo or in vitro under conditions that are stringent enough to ensure a specific hybridization.

Stringent in vitro hybridization conditions are known to the person skilled in the art and can be taken from the literature (see e.g. Sambrook et al., Molecular Cloning, Cold Spring Harbor Press). The term "specific hybridization" refers to the case wherein a molecule preferentially binds to a certain nucleic acid sequence under stringent conditions, if this nucleic acid sequence is part of a complex mixture of e.g. DNA or RNA molecules.

The term "stringent conditions" therefore refers to conditions, under which a nucleic acid sequence preferentially binds to a target sequence, but not, or at least to a significantly reduced extent, to other sequences.

Stringent conditions are dependent on the circumstances. Longer sequences specifically hybridize at higher temperatures. In general, stringent conditions are chosen in such a way that the hybridization temperature lies about 5° C. below the melting point (Tm) of the specific sequence with a defined ionic strength and a defined pH value. Tm is the temperature (with a defined pH value, a defined ionic strength and a defined nucleic acid concentration), at which 50% of the molecules, which are complementary to a target sequence, hybridize with said target sequence. Typically, stringent conditions comprise salt concentrations between 0.01 and 1.0 M sodium ions (or ions of another salt) and a pH value between 7.0 and 8.3. The temperature is at least 30° C. for short molecules (e.g. for such molecules comprising between 10 and 50 nucleotides). In addition, stringent conditions can comprise the addition of destabilizing agents like e.g. formamide. Typical hybridization and washing buffers are of the following composition.

Pre-Hybridization Solution:
  0.5% SDS
  5×SSC
  50 ml NaPO$_4$, pH 6.8
  0.1% Na-pyrophosphate
  5×Denhardt's reagent
  100 µg salmon sperm Hybridization Solution:
  Pre-hybridization solution
  1×10$^6$ cpm/mL probe (5-10 min 95° C.)

20×SSC:
  3 M NaCl
  0.3 M sodium citrate
  ad pH 7 with HCl

50×Denhardt's Reagent:
  5 g Ficoll
  5 g polyvinylpyrrolidone
  5 g Bovine Serum Albumin
  ad 500 mL A. dest.

A typical procedure for the hybridization is as follows:

| Optional: | wash Blot 30 min in 1x SSC/0.1% SDS at 65° C. | |
|---|---|---|
| Pre-hybridization: | at least 2 h at 50-55° C. | |
| Hybridization: | over night at 55-60° C. | |
| Washing: | 05 min  2x SSC/0.1% SDS Hybridization temperature | |
| | 30 min  2x SSC/0.1% SDS | |
| | 30 min  1x SSC/0.1% SDS | |
| | 45 min  0.2x SSC/0.1% SDS | 65° C. |
| | 5 min  0.1x SSC | room temperature |

The terms "sense" and "antisense" as well as "antisense orientation" are known to the person skilled in the art. Furthermore, the person skilled in the art knows how long nucleic acid molecules, which are to be used for antisense methods, must be and which homology or complementarity they must have concerning their target sequences.

Accordingly, the person skilled in the art also knows how long nucleic acid molecules, which are used for gene silencing methods, must be. For antisense purposes complementarity over sequence lengths of 100 nucleotides, 80 nucleotides, 60 nucleotides, 40 nucleotides and 20 nucleotides may suffice. Longer nucleotide lengths will certainly also suffice. A combined application of the above-mentioned methods is also conceivable.

If, according to the present invention, DNA sequences are used, which are operatively linked in 5'-3'-orientation to a promoter active in the organism, vectors can, in general, be constructed, which, after the transfer to the organisms cells, allow the overexpression of the coding sequence or cause the suppression or competition and blockage of endogenous nucleic acid sequences and the proteins expressed therefrom, respectively.

The activity of a particular enzyme may also be reduced by over-expressing a non-functional mutant thereof in the organism. Thus, a non-functional mutant which is not able to catalyze the reaction in question, but that is able to bind e.g. the substrate or co-factor, can, by way of over-expression outcompete the endogenous enzyme and therefore inhibit the reaction. Further methods in order to reduce the amount and/or activity of an enzyme in a host cell are well known to the person skilled in the art.

Another aspect of the invention pertains to vectors, preferably expression vectors, containing a nucleic acid encoding the enzymes of Table 1 (or portions thereof) or combinations thereof. As used herein, the term "vector" refers to a nucleic acid molecule capable of transporting another nucleic acid to which it has been linked.

One type of vector is a "plasmid", which refers to a circular double stranded DNA loop into which additional DNA segments can be ligated. Another type of vector is a viral vector, wherein additional DNA segments can be ligated into the viral genome.

Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked.

Such vectors are referred to herein as "expression vectors".

In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention may comprise a nucleic acid coding for the enzymes of Table 1 in a form suitable for expression of the respective nucleic acid in a host cell, which means that the recombinant expression vectors include one or more regulatory sequences, selected on the basis of the host cells to be used for expression, which is operatively linked to the nucleic acid sequence to be expressed.

Within a recombinant expression vector, "operably linked" is intended to mean that the nucleotide sequence of interest is linked to the regulatory sequence (s) in a manner which allows for expression of the nucleotide sequence (e.g., in an in vitro transcription/translation system or in a host cell when the vector is introduced into the host cell). The term "regulatory sequence" is intended to include promoters, repressor binding sites, activator binding sites, enhancers and other expression control elements (e.g., terminators, polyadenylation signals, or other elements of mRNA secondary structure). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells. Preferred regulatory sequences are, for example, promoters such as cos-, tac-, trp-, tet-, trp-tet-, lpp-, lac-, lpp-lac-, lacIq-, T7-, T5-, T3-, gal-, trc-, ara-, SP6-, arny, SP02, e-Pp-ore PL, sod, ef-tu, groE, which are used preferably in bacteria. Additional regulatory sequences are, for example, promoters from yeasts and fungi, such as ADC1, MFa, AC, P-60, CYC1, GAPDH, TEF, rp28, ADH, promoters from plants such as CaMV/35S, SSU, OCS, lib4, usp, STLS1, B33, nos or ubiquitin- or phaseolin-promoters. It is also possible to use artificial promoters. It will be appreciated by one of ordinary skill in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids coding for the enzymes of Table 1.

The recombinant expression vectors of the invention can be designed for expression of the enzymes in Table 1 in prokaryotic or eukaryotic cells. For example, the genes for the enzymes of Table 1 can be expressed in bacterial cells such as *C. glutamicum, B. subtilis* and *E. coli*, insect cells (using baculovirus expression vectors), yeast and other fungal cells (see Romanos, M. A. et al. (1992), Yeast 8: 423-488; van den Hondel, C. A. M. J. J. et al. (1991) in: More Gene Manipulations in Fungi, J. W. Bennet & L. L. Lasure, eds., p. 396-428: Academic Press: San Diego; and van den Hondel, C. A. M. J. J. & Punt, P. J. (1991) in: Applied Molecular Genetics of Fungi, Peberdy, J. F. et al., eds., p. 1-28, Cambridge University Press: Cambridge), algae and multicellular plant cells (see Schmidt, R. and Willmitzer, L. (1988) Plant Cell Rep.: 583-586). Suitable host cells are discussed further in Goeddel, Gene Expression Technology Methods in Enzymology 185, Academic Press, San Diego, Calif. (1990). Alternatively, the recombinant expression vector can be transcribed and translated in vitro, for example using T7 promoter regulatory sequences and T7 polymerase. Expression of proteins in prokaryotes is most often carried out with vectors containing constitutive or inducible promoters directing the expression of either fusion or non-fusion proteins.

Fusion vectors add a number of amino acids to a protein encoded therein, usually to the amino terminus of the recombinant protein but also to the C-terminus or fused within suitable regions in the proteins. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase.

Typical fusion expression vectors include pQE (Qiagen), pGEX (Pharmacia Biotech Inc; Smith, D. B. and Johnson, K. S. (1988) Gene 67: 31-40), pMAL (New England Biolabs, Beverly, Mass.) and pRIT5 (Pharmacia, Piscataway, N.J.) which fuse glutathione S-transferase (GST), maltose E binding protein, or protein A, respectively.

Examples for *C. glutamicum* vectors can be found in the Handbook of *Corynebacterium* 2005 Eggeling, L. Bott, M., eds., CRC press USA.

Examples of suitable inducible non-fusion *E. coli* expression vectors include pTrc (Amann et al., (1988) Gene 69; 301-315), pLG338, pACYC184, pBR322, pUC18, pUC19, pKC30, pRep4, pHS1, pHS2, pPLc236, pMBL24, pLG200, pUR290, pIN-III113-Bl, egtll, pBdCl, and pET lld (Studier et al., Gene Expression Technology: Methods in Enzymology 185, Academic Press, San Diego, Calif. (1990) 60-89; and Pouwels et al., eds. (1985) Cloning Vectors. Elsevier: New York IBSN 0 444 904018). Target gene expression from the pTrc vector relies on host RNA polymerase transcription from a hybrid trp-lac fusion promoter. Target gene expression from the pET lld vector relies on transcription from a T7 gnlO-lac fusion promoter mediated by a coexpressed viral RNA polymerase (T7gnl). This viral polymerase is supplied by host strains BL21 (DE3) or HMS174 (DE3) from a residentX prophage harboring a T7gnl gene under the transcriptional control of the lacUV 5 promoter. For transformation of other varieties of bacteria, appropriate vectors may be selected. For example, the plasmidspIJ101, pIJ364, pIJ702 and pIJ361 are known to be useful in transforming *Streptomyces*, while plasmids pUB110, pC194, or pBD214 are suited for transformation of *Bacillus* species. Several plasmids of use in the transfer of genetic information into *Corynebacterium* include pHM1519, pBL1, pSA77, or pAJ667 (Pouwels et al., eds. (1985) Cloning Vectors. Elsevier: New York IBSN 0 444 904018).

One strategy to maximize recombinant protein expression is to express the protein in host bacteria with an impaired capacity to proteolytically cleave the recombinant protein (Gottesman, S., Gene Expression Technology: Methods in Enzymology 185, Academic Press, San Diego, Calif. (1990) 119-128). Another strategy is to alter the nucleic acid sequence of the nucleic acid to be inserted into an expression vector so that the individual codons for each amino acid are those preferentially utilized in the bacterium chosen for expression, such as *C. glutamicum* (Wada et al. (1992)

*Nucleic Acids Res.* 20: 2111-2118). Such alteration of nucleic acid sequences of the invention can be carried out by standard DNA synthesis techniques.

In another embodiment, the protein expression vector is a yeast expression vector. Examples of vectors for expression in yeast, *S. cerevisiae* include pYepSec1 (Baldari, et al., (1987) Embo J. 6: 229-234), 21, pAG-1, Yep6, Yep13, pEMBLYe23, pMFa (Kurjan and Herskowitz, (1982) Cell 30: 933-943), pJRY88 (Schultz et al., (1987) Gene 54 113-123), and pYES2 (Invitrogen Corporation, San Diego, Calif.). Vectors and methods for the construction of vectors appropriate for use in other fungi, such as the filamentous fungi, include those detailed in: van den Hondel, C. At M. J. J. & Punt, P. J. (1991) in: Applied Molecular Genetics of Fungi, J. F, Peberdy, et al, eds., p. 1-28, Cambridge University Press: Cambridge, and Pouwels et al., eds. (1985) Cloning Vectors. Elsevier: New York (IBSN 0 444 904018).

For the purposes of the present invention, an operative link is understood to be the sequential arrangement of promoter, coding sequence, terminator and, optionally, further regulatory elements in such a way that each of the regulatory elements can fulfill its function, according to its determination, when expressing the coding sequence.

In another embodiment, the proteins of Table 1 may be expressed in unicellular plant cells (such as algae) or in plant cells from higher plants (e.g., the spermatophytes such as crop plants). Examples of plant expression vectors include those detailed in: Becker, D., Kemper, E., Schell, J. and Masterson, R. (1992) Plant Mol. Biol. 20: 1195-1197; and Bevan, M. W. (1984) Nucl. Acid. Res. 12: 8711-8721, and include pLGV23, pGHlac+, pBIN19, pAK2004, and pDH51 (Pouwels et al., eds. (1985) Cloning Vectors. Elsevier. New York IBSN 0 444 904018).

For other suitable expression systems for both prokaryotic and eukaryotic cells see chapters 16 and 17 of Sambrook, J. et al. Molecular Cloning: A Laboratory Manual. 3rd ed., Cold Spring Harbor Laboratory, Cold Spring Harbor Laboratory Press, Cold Spring Harbor, N.Y., 2003.

For the purposes of the present invention, an operative link is understood to be the sequential arrangement of promoter, coding sequence, terminator, and, optionally, further regulatory elements in such a way that each of the regulatory elements can fulfill its function, according to its determination, when expressing the coding sequence.

In another embodiment, the recombinant mammalian expression vector is capable of directing expression of the nucleic acid preferentially in a particular cell type, e.g. in plant cells (e.g., tissue-specific regulatory elements are used to express the nucleic acid). Tissue-specific regulatory elements are known in the art.

Another aspect of the invention pertains to organisms or host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an enzyme of Table 1 can be expressed in bacterial cells such as *C. glutamicum* or *E. coli*, insect cells, yeast or plants. Other suitable host cells are known to those of ordinary skill in the art.

Vector DNA can be introduced into prokaryotic or eukaryotic cells via conventional transformation or transfection techniques. As used herein, the terms "transformation" and "transfection", "conjugation" and "transduction" are intended to refer to a variety of art-recognized techniques for introducing foreign nucleic acid (e.g., linear DNA or RNA, e.g., a linearized vector or a gene construct alone without a vector) or nucleic acid in the form of a vector (e.g., a plasmid, phage, phasmid, phagemid, transposon or other DNA) into a host cell, including calcium phosphate or calcium chloride co-precipitation, DEAE-dextran-mediated transfection, lipofection, natural competence, chemical-mediated transfer, or electroporation. Suitable methods for transforming or transfecting host cells can be found in Sambrook, et al. (Molecular Cloning: A Laboratory Manual. 3rd ed., Cold Spring Harbor Laboratory, Cold Spring Harbor Laboratory Press, Cold Spring Harbor, N.Y., 2003). Examples for *C. glutamicum* vectors can be found in the Handbook of *Corynebacterium* (Eggeling, L. Bott, M., eds., CRC press USA 2005) and other laboratory manuals.

"Campbell in", as used herein, refers to a transformant of an original host cell in which an entire circular double stranded DNA molecule (for example a plasmid) is integrated into a chromosome by a single homologous recombination event (a cross in event), and that effectively results in the insertion of a linearized version of said circular DNA molecule into a first DNA sequence of the chromosome that is homologous to a first DNA sequence of the said circular DNA molecule. The name comes from Professor Alan Campbell, who first proposed this kind of recombination. "Campbelled in" refers to the linearized DNA sequence that has been integrated into the chromosome of a "Campbell in" transformant. A "Campbell in" contains a duplication of the first homologous DNA sequence, each copy of which includes and surrounds a copy of the homologous recombination crossover point.

"Campbell out", as used herein, refers to a cell descending from a "Campbell in" transformant, in which a second homologous recombination event (a cross out event) has occurred between a second DNA sequence that is contained on the linearized inserted DNA of the "Campbelled in" DNA, and a second DNA sequence of chromosomal origin, which is homologous to the second DNA sequence of said linearized insert, the second recombination event resulting in the deletion (jettisoning) of a portion of the integrated DNA sequence, but, importantly, also resulting in a portion (this can be as little as a single base) of the integrated "Campbelled in" DNA remaining in the chromosome, such that compared to the original host cell, the "Campbell out" cell contains one or more intentional changes in the chromosome (for example, a single base substitution, multiple base substitutions, insertion of a heterologous gene or DNA sequence, insertion of an additional copy or copies of a homologous gene or a modified homologous gene, or insertion of a DNA sequence comprising more than one of these aforementioned examples listed above).

A "Campbell out" cell or strain is usually, but not necessarily, obtained by a counter-selection against a gene that is contained in a portion (the portion that is desired to be jettisoned) of the "Campbelled in" DNA sequence, for example the *Bacillus subtilis* sacB gene, which is lethal when expressed in a cell that is grown in the presence of about 5% to 10% sucrose. Either with or without a counter-selection, a desired "Campbell out" cell can be obtained or identified by screening for the desired cell, using any screenable phenotype, such as, but not limited to, colony morphology, colony color, presence or absence of antibiotic resistance, presence or absence of a given DNA sequence by polymerase chain reaction, presence or absence of an auxotrophy, presence or absence of an enzyme, colony nucleic acid hybridization, antibody screening, etc.

The term "Campbell in" and "Campbell out" can also be used as verbs in various tenses to refer to the method or process described above.

It is understood that the homologous recombination events that leads to a "Campbell in" or "Campbell out" can occur over a range of DNA bases within the homologous DNA sequence, and since the homologous sequences will be identical to each other for at least part of this range, it is not usually possible to specify exactly where the crossover event occurred. In other words, it is not possible to specify precisely which sequence was originally from the inserted DNA, and which was originally from the chromosomal DNA. Moreover, the first homologous DNA sequence and the second homologous DNA sequence are usually separated by a region of partial non-homology, and it is this region of non-homology that remains deposited in a chromosome of the "Campbell out" cell.

For practicality, in C. glutamicum, typical first and second homologous DNA sequence are usually at least about 200 base pairs in length, and can be up to several thousand base pairs in length. However, the procedure can also be adapted to work with shorter or longer sequences. For example, a length for the first and second homologous sequences can range from about 500 to 2000 bases, and obtaining a "Campbell out" from a "Campbell in" is facilitated by arranging the first and second homologous sequences to be approximately the same length, preferably with a difference of less than 200 base pairs and most preferably with the shorter of the two being at least 70% of the length of the longer in base pairs.

In order to identify and select these integrants, a gene that encodes a selectable marker (e.g., resistance to antibiotics) is generally introduced into the host cells along with the gene of interest. Preferred selectable markers include those which confer resistance to drugs, such as kanamycin, chloramphenicol, tetracyclin, G418, hygromycin and methotrexate. Nucleic acid encoding a selectable marker can be introduced into a host cell on the same vector as that encoding the enzymes of Table 1 or can be introduced on a separate vector. Cells stably transfected with the introduced nucleic acid can be identified by drug selection (e.g., cells that have incorporated the selectable marker gene will survive, while the other cells die).

In another embodiment, recombinant microorganisms can be produced which contain systems which allow for enhanced expression of the selected and/or introduced gene. Examples for altered and enhanced expression of genes in high GC organisms like like C. glutamicum are described in WO 2005/059144, WO 2005/059143 and WO 2005/059093.

In another embodiment, recombinant microorganisms can be produced which contain selected systems which allow for regulated expression of the introduced gene. For example, inclusion of a gene of Table 1 on a vector placing it under control of the lac operon permits expression of the gene only in the presence of IPTG. Such regulatory systems are well known in the art.

In one embodiment, the method comprises culturing the organisms of invention (into which a recombinant expression vector encoding e.g. an enzyme of table 1 has been introduced, or into which genome has been introduced a gene encoding a wild-type or altered enzyme) in a suitable medium for methionine production. In another embodiment, the method further comprises isolating methionine from the medium or the host cell.

In order to modify the metabolic flux of an organism to produce an organism that is more efficient in methionine synthesis, changing the amount and/or activity of an enzyme is not limited to the enzymes listed in Table 1. Any enzyme that is homologous to the enzymes of Table 1 and carries out the same function in another organism may be perfectly suited to modulate the amount and/or activity in order to influence the metabolic flux by way of over-expression. The definitions for homology and identity have been given above.

The person skilled in the art is familiar with the cultivation of common microorganisms such as C. glutamicum and E. coli. Thus, a general teaching will be given below as to the cultivation of C. glutamicum. Corresponding information may be retrieved from standard textbooks for cultivation of E. coli.

E. coli strains are routinely grown in MB and LB broth, respectively (Follettie, M. T., Peoples, O., Agoropoulou, C., and Sinskey, A. J. (1993) J. Bacteriol. 175, 4096-4103). Minimal media for E. coli is M9 and modified MCGC (Yoshihama, M., Higashiro, K., Rao, E. A., Akedo, M., Shanabruch, W G., Follettie, M. T., Walker, G. C., and Sinskey, A. J. (1985) J. Bacteriol. 162, 591-507), respectively. Glucose may be added at a final concentration of 1%. Antibiotics may be added in the following amounts (micrograms per milliliter): ampicillin, 50; kanamycin, 25; nalidixic acid, 25. Amino acids, vitamins, and other supplements may be added in the following amounts: methionine, 9.3 mM; arginine, 9.3 mM; histidine, 9.3 mM; thiamine, 0.05 mM. E. coli cells are routinely grown at 37° C., respectively.

Genetically modified Corynebacteria are typically cultured in synthetic or natural growth media. A number of different growth media for Corynebacteria are both well-known and readily available (Lieb et al. (1989) Appl. Microbiol. Biotechnol., 32: 205-210; von der Osten et al. (1998) Biotechnology Letters, 11: 11-16; Pat. DE 4,120,867; Liebl (1992) "The Genus Corynebacterium in: The Procaryotes, Volume II, Balows, A. et al., eds. Springer-Verlag). Examples for C. glutamicum vectors can be found in the Handbook of Corynebacterium (Eggeling, L. Bott, M., eds., CRC press USA 2005).

These media consist of one or more carbon sources, nitrogen sources, inorganic salts, vitamins and trace elements. Preferred carbon sources are sugars, such as mono-, di-, or polysaccharides. For example, glucose, fructose, mannose, galactose, ribose, sorbose, ribose, lactose, maltose, sucrose, raffinose, starch or cellulose may serve as very good carbon sources.

It is also possible to supply sugar to the media via complex compounds such as molasses or other by-products from sugar refinement. It can also be advantageous to supply mixtures of different carbon sources. Other possible carbon sources are alcohols and organic acids, such as methanol, ethanol, acetic acid or lactic acid. Nitrogen sources are usually organic or inorganic nitrogen compounds, or materials which contain these compounds. Exemplary nitrogen sources include ammonia gas or ammonia salts, such as $NH_4Cl$ or $(NH_4)_2SO_4$, $NH_4OH$, nitrates, urea, amino acids or complex nitrogen sources like corn steep liquor, soy bean flour, soy bean protein, yeast extract, meat extract and others.

The overproduction of methionine is possible using different sulfur sources. Sulfates, thiosulfates, sulfites and also more reduced sulfur sources like $H_2S$ and sulfides and derivatives can be used. Also organic sulfur sources like methyl mercaptan, thioglycolates, thiocyanates, thiourea, sulfur containing amino acids like cysteine and other sulfur containing compounds can be used to achieve efficient methionine production. Formate and/or methanethiol may also be possible as a supplement as are other C1 sources such as formaldehyde, methanol and dimethyl-disulfide.

Inorganic salt compounds which may be included in the media include the chloride-, phosphorous- or sulfate-salts of calcium, magnesium, sodium, cobalt, molybdenum, potassium, manganese, zinc, copper and iron. Chelating compounds can be added to the medium to keep the metal ions in solution. Particularly useful chelating compounds include dihydroxyphenols, like catechol or protocatechuate, or organic acids, such as citric acid. It is typical for the media to also contain other growth factors, such as vitamins or growth promoters, examples of which include biotin, riboflavin, thiamin, folic acid, nicotinic acid, pantothenate and pyridoxin. Growth factors and salts frequently originate from complex media components such as yeast extract, molasses, corn steep liquor and others. The exact composition of the media compounds depends strongly on the immediate experiment and is individually decided for each specific case. Information about media optimization is available in the textbook "Applied Microbiol. Physiology, A Practical Approach (eds. P. M. Rhodes, P. F. Stanbury, IRL Press (1997) pp. 53-73, ISBN 0 19 963577 3). It is also possible to select growth media from commercial suppliers, like standard 1 (Merck) or BHI (grain heart infusion, DIFCO) or others.

All medium components should be sterilized, either by heat (20 minutes at 1.5 bar and 121° C.) or by sterile filtration. The components can either be sterilized together or, if necessary, separately.

All media components may be present at the beginning of growth, or they can optionally be added continuously or batchwise. Culture conditions are defined separately for each experiment.

The temperature should be in a range between 15° C. and 45° C. The temperature can be kept constant or can be altered during the experiment. The pH of the medium may be in the range of 5 to 8.5, preferably around 7.0, and can be maintained by the addition of buffers to the media. An exemplary buffer for this purpose is a potassium phosphate buffer. Synthetic buffers such as MOPS, HEPES, ACES and others can alternatively or simultaneously be used. It is also possible to maintain a constant culture pH through the addition of NaOH or $NH_4OH$ during growth. If complex medium components such as yeast extract are utilized, the necessity for additional buffers may be reduced, due to the fact that many complex compounds have high buffer capacities. If a fermentor is utilized for culturing the micro-organisms, the pH can also be controlled using gaseous ammonia.

The incubation time is usually in a range from several hours to several days. This time is selected in order to permit the maximal amount of product to accumulate in the broth. The disclosed growth experiments can be carried out in a variety of vessels, such as microtiter plates, glass tubes, glass flasks or glass or metal fermentors of different sizes. For screening a large number of clones, the microorganisms should be cultured in microtiter plates, glass tubes or shake flasks, either with or without baffles. Preferably 100 mL shake flasks are used, filled with 10% by volume) of the required growth medium. The flasks should be shaken on a rotary shaker (amplitude 25 mm) using a speed-range of 100-300 rpm. Evaporation losses can be diminished by the maintenance of a humid atmosphere; alternatively, a mathematical correction for evaporation losses should be performed.

If genetically modified clones are tested, an unmodified control clone or a control clone containing the basic plasmid without any insert should also be tested. The medium is inoculated to an OD600 of 0.5-1.5 using cells grown on agar plates, such as CM plates (10 g/L glucose, 2.5 g/L NaCl, 2 g/l urea, 10 g/L polypeptone, 5 g/L yeast extract, 5 g/L meat extract, 22 g/L NaCl, 2 g/L urea, 10 g/L polypeptone, 5 g/L yeast extract, 5 g/L meat extract, 22 g/L agar, pH 6.8 with 2M NaOH) that had been incubated at 30° C.

Inoculation of the media is accomplished by either introduction of a saline suspension of C. glutamicum cells from CM plates or addition of a liquid preculture of this bacterium.

Although the present invention has been described with reference to Corynebacterium glutamicum and the production of L-methionine, it should be pointed out that the present invention can also be applied to other microorganism and to the production of other amino acids.

In addition, it should be pointed out that "comprising" does not exclude any other elements or steps and that "one" does not exclude a plural number. Furthermore, it should be pointed out that the characteristics or steps which have been described with reference to one of the above embodiments can also be used in combination with other characteristics or steps of other embodiments described above.

The invention is further illustrated by the following examples, which should not be construed as limiting. The contents of all references, patent applications, patents, published patent applications, tables, appendices and the sequences cited throughout this application are hereby incorporated by reference.

EXAMPLES

Bacterial strain. *Corynebacterium glutamicum* ATCC 13032 (wild-type) was obtained from the American Type Culture Collection (Manassas, Va., USA). The knockout mutants were constructed as follows:

*C. glutamicum* M1840 was a ΔMcbR strain derived from the wild type ATCC13032 (Rey et al., 2003, vide supra). ATCC 13032 was transformed with the plasmid pH430 (SEQ ID No. 1) and "Campbelled in" in to yield "Campbell in" strains. "Campbell in" strains were then "Campbelled out" to yield "Campbell out" strain M1840, which contains a deletion of the McbR gene.

*C. glutamicum* M1840 was transformed with the plasmid pH238 (SEQ ID No. 2) and "Campbelled in" in to yield "Campbell in" strains. "Campbell in" strains were then "Campbelled out" to yield "Campbell out" strain M11840 Δhom, Δhsk, which contains a deletion of the homoserine dehydrogenase and the homoserine kinase genes.

*C. glutamicum* M1840 was transformed with the plasmid p (SEQ ID No. 3) and "Campbelled in" in to yield "Campbell in" strains. "Campbell in" strains were then "Campbelled out" to yield "Campbell out" strain M1840 ΔmetB which contains a deletion of the MetB gene. In this strain no measurable cystathionine γ-synthase was observed.

Chemicals. Casaminoacids, beef extract, polypeptone and yeast extract were supplied from Difco (Detroit, USA). All other chemicals were of analytical grade and purchased from Grüssing (Filsum, Germany), Acros Organics (Geel, Belgium), Merck (Darmstadt, Germany), Aldrich (Steinheim, Germany), and Fluka (Buchs, Switzerland). The tracer substrates, 99% $[^{13}C_6]$ glucose and 98% $[^{13}C_4]$ threonine were supplied by Cambridge Isotopes Inc. (Andova, Mass., USA). 99% $[^{15}N]$ ammonium sulfate was purchased from Campro Scientific (Veenendaal, The Netherlands). $[^{34}S]$ sulfate was kindly provided by BASF AG (Ludwigshafen, Germany).

Media and growth conditions. Cells for inoculation were grown on rich medium containing 10.00 g/L glucose, 2.50 g/L NaCl, 2.00 g/L urea, 5.00 g/L yeast extract, 5.0 g/L beef extract, 5.0 g/L polypeptone, 20.0 g/L Casaminoacids and 20.0 g/L agar (for plates). The cells were maintained on plates at 30° C. Precultures were grown over night in 250 mL baffled shake flasks with 25 mL rich liquid medium. The cells were harvested by centrifugation (2 min, 10000 g, 4° C.), washed twice with 0.9% NaCl and used for inoculation in the second preculture on minimal medium. The second preculture was harvested as described above and used as starter of the main cultivations, carried out on minimal medium. The minimal medium was composed as follows: 40.00 g/L glucose, 1.00 g/L $K_2HPO_4$, 1.00 g/L $KH_2PO_4$, 42.00 g/L MOPS, 54.00 g/L ACES, 20.00 g/L $(NH_4)_2SO_4$, 0.30 g/L 3,4-dihydroxybenzoic acid, 0.01 g/L $CaCl_2$, 0.25 g/L $MgSO_4*7H_2O$, 0.01 g/L $FeSO_4*7H_2O$, 0.01 g/L $MnSO_4*H_2O$, 0.002 g/L $ZnSO_4*7H_2O$, 0.2 mg/L $CuSO_4*5H_2O$, 0.02 mg/L $NiCl_2*6H_2O$, 0.02 mg/L $Na_2MoO_4*2H_2O$, 0.1 mg/L cyanocobalamin, 0.3 mg/L thiamine, 0.004 mg/L pyridoxal phosphate, 0.1 mg/L biotin. For the cultivation of the auxtrophic mutant M1840 H238 and the characterization of the methionine biosynthetic pathway the medium was supplemented with 10 mM of threonine, homoserine, methionine, cystathionine and homocysteine respectively. Tracer experiments were performed in 5 mL cultures in 50 mL baffled shake flasks on a rotary shaker at 250 rpm (shaking radius 2.5 cm) and 30° C. The cells were harvested at late exponential phase. Other experiments were carried out in 500 mL baffled shake flasks in 50 mL medium on a rotary shaker (250 rpm, 30° C., shaking radius 2.5 cm).

Metabolome. Intracellular metabolites were extracted as described earlier (Kromer et al., 2004). Washed ($H_2O$) biomass was hydrolyzed for 48 h (105° C., 6 N HCl). The hydrolysates were neutralized (6N NaOH). For GC/MS analysis the samples (400 µL extracts or 50 µL hydrolysates) were freeze dried, resuspended in 50 µL solvent (0.1% pyridine in dimethylformamide) and finally derivatized 1 h with 50 µL N-Methyl(tert-butyldimethylsilyl)trifluoroacetamide (MBD-STFA) at 80° C. Labeling analysis with GC/MS was performed as described earlier (Wittmann, C. et al., Anal Biochem 2002, 3072, 379-82). Except for proline, all proteinogenic amino acids and intermediates of the methionine metabolism, including homocysteine, homoserine, O-acetylhomoserine and cystathionine, were quantified on HPLC as described elsewhere (Krömer et al., Anal Biochem. 2005; 340:171-3). Quantification of homolanthionine was done using HPLC with cystathionine calibration factor.

Overexpression and purification of enzymes. MetB and MetC of *C. glutamicum* were cloned in the vector pQE30 (Qiagen). Expression with this vector comprises the addition of a His-Tag to the N-terminus of the expressed protein. *Escherichia coli* was transformed with the plasmid and selected by ampicillin resistance (100 µg/mL). Transformed *E. coli* was cultivated (100 µg/mL ampicillin, 37° C., 230 rpm) on terrific broth (Losen et al., Biotechnol Prog 2004, 204, 1062-8) and induced at an optical density of 1 (600 nm) by addition of 1 mM isopropyl thiogalactoside (final concentration). The cells were harvested by centrifugation (4225 g, 15 min, 2° C.) after 16 h of induced growth, washed and resuspended in phosphate buffer (100 mM, 100 µM pyridoxal phosphate, 1 mg/mL DNAse 1, pH 7.4 at 4° C.) and extracted by sonication (5×15 sec, 20 micron). The crude extracts were separated from cell debris by centrifugation (30 min, 2° C., and 20000 g). Recombinant MetB and MetC were finally purified by affinity chromatography on an ÄKTA Purifier 900 (Amersham Biosciences, Little Chalfont, England) equipped with a HiTrap chelating Nickel-Sepharose column (5 mL, Amersham) equilibrated with 0.02 M sodium phosphate buffer (pH 7.4) containing 0.5 M NaCl. After the protein was applied to the column, it was washed with 10 vol. of 0.02 M sodium phosphate buffer. Elution was carried out with a linear gradient with 0.02 M sodium phosphate buffer (pH 7.4) containing 0.5 M NaCl and 0.5 M imidazol. The fractions containing the protein were checked for purity with SDS-PAGE and then pooled together. Imidazole was separated from the proteins by ultrafiltration.

In vitro assays of MetB and MetC. Activity of MetB and MetC was followed photometrically (Helios α, Thermo Electronic, Dreieich, Germany). Enzyme activities were measured by increase or decrease of free SH-groups using Ellman's reagent (Extinction at 412 nm) (Ellman and Lysko, 1979). The assay mixtures contained 1.25 mM cysteine or homocysteine and 3 mM O-acetyl homoserine for MetB-assays and 1.25 mM cystathionine or about 1.25 mM homolanthionine for MetC-assays. Homolanthionine was not commercially available. The MetC-assay was therefore carried out using the products of the MetB-assay. MetB was removed by ultrafiltration. Thus, the homolanthionine concentration could not be adjusted in the assays. Additionally the assay solutions consisted of phosphate buffer (100 mM, pH 7.5) and 10 µM pyridoxyl-5-phosphate, cofactor of MetB and MetC. 65 µL samples were taken from the assay mixture and injected into 935 µL of a stopping solution at any time. The stopping solution consisted of phosphate buffer (100 nm, pH 7.5) with 38% ethanol and 1 mM dithionitrobenzoic acid (DTNB). The ethanol stopped enzyme activity and the DTNB formed a yellow complex with homocysteine or cysteine. The assay gave linear results up to 1.5 mM of free SH-groups The $K_m$-values were determined from double reciprocal Lineweaver-Burk plots.

Table 2 shows isoleucine, threonine and alanine labeling in homoserine/methionine and threonine auxotrophic *C. glutamicum* ΔMcbR, Δhom, Δhsk. Cultivation occurred on naturally labeled homoserine and $[U^{13}C]$-Glucose (99%) and $[U^{13}C]$-threonine (98%). Shown is the relative abundance of the different mass isotopomers in protein hydrolyzates.

TABLE 2

| Mass isotopomer | Isoleucine (m/z = 200; $C_2$-$C_6$) [%] | Threonine (m/z = 404; $C_1$-$C_4$) [%] | Alanine (m/z = 260; $C_1$-$C_3$) [%] |
|---|---|---|---|
| m | 0.5 | 1.1 | 0.7 |
| m + 1 | 0.5 | 0.4 | 0.6 |
| m + 2 | 13.3 | 1.1 | 5.2 |
| m + 3 | 1.4 | 8.5 | 93.5 |
| m + 4 | 8.0 | 88.8 | |
| m + 5 | 76.3 | | |

Table 3 shows $K_m$-values for MetC and MetB of *C. glutamicum* compared to other organisms.

TABLE 3

| Substrate | MetC $K_m$ [µM] | | Reference |
|---|---|---|---|
| L-cysta-thionine | 107 | (*C. glutamicum*) | (this study) |
| | 40 | (*E. coli*) | (Dwivedi, C. M. et al., Biochemistry 1982, 2113, 3064-9) |
| | 220 | (*S. thyphimurium*) | (Dwivedi et al., 1982, vide supra) |
| | 70 | (*B. avium*) | (Gentry-Weeks, C. R. et al., J. Biol. Chem. 1993, 26810, 7298-314) |
| L-homolan-thionine | 4540 | (*E. coli*) | (Dwivedi et al., 1982, vide supra) |

TABLE 3-continued

| Substrate | MetB $K_m$ [µM] | Reference |
|---|---|---|
| L-cysteine | 258 (C. glutamicum) | (this study) |
|  | 180 (Spinach) | (Ravanel et al., Arch Biochem Biophys 1995, 3361, 572-84) |
|  | 50 (E. coli) | (Holbrook et al., Biochemistry 1990, 292, 435-42) |
| L-homo-cysteine | 541 (C. glutamicum) | (this study) |

Figure 1B:
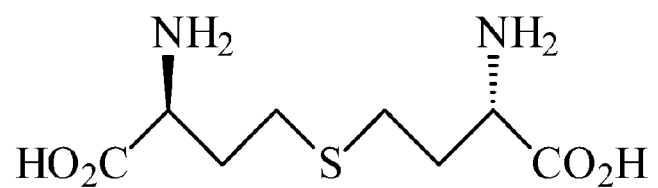
FIG. 1b shows the structure of L-homolanthionine (S-[(3S)-3-amino-3-carboxypropyl]-L-homocysteine).

Results:

Physiological response to the McbR knockout. The knockout of the transcriptional regulator McbR in *Corynebacterium glutamicum* has severe consequences for cellular metabolism. The strain *C. glutamicum* M1840, only differing from the wild-type by the knockout of McbR, showed a reduced growth rate of 0.18 [$h^{-1}$]. In comparison, the wild-type had a growth rate of 0.41 [$h^{-1}$]. Moreover, the biomass yield was significantly reduced in M1840. While the wild type yielded 0.55 $g_{Biomass}\ g_{Glucose}^{-1}$ M1840 produced only 0.36 $g_{Biomass}\ g_{Glucose}^{-1}$. These results indicate that the cells metabolism is strongly sensitive to the McbR knockout. During exponential growth, *C. glutamicum* M1840 exhibited elevated intracellular homocysteine and cysteine titers. Compared to the wild type, the intracellular homocysteine concentration increased from 0.1 to 2.9 µmoles $g_{CDW}^{-1}$ and cysteine increased from 0.3 to 2.8 µmoles $g_{CDW}^{-1}$. This equals 29 and 9.3 fold increases, respectively. It becomes obvious that the knockout of McbR leads to the accumulation of important methionine precursors. However, the HPLC and GC/MS spectra also showed an additional intense signal that could be identified as homolanthionine (FIG. 1b).

Identification of homolanthionine. The homolanthionine structure differs from cystathionine by the content of an additional methylene group (FIG. 1b). Both α-carbon atoms have S-configuration in natural homolanthionine. The homolanthionine was quantified with the HPLC calibration factor obtained for cystathionine. The accumulation of 250 µmol $g_{CDW}^{-1}$ in exponentially growing *C. glutamicum* M1840 (=ATCC13032 ΔMcbR) compared to 1.3 µmol $g_{CDW}^{-1}$ in the isogenic wildtype strain ATCC13032 makes this amino acid the second important intracellular amino acid besides glutamate (325 µmol $g_{CDW}^{-1}$). Homolanthionine was identified by labeling experiments and GC/MS fragment pattern. Separate cultivations of *C. glutamicum* M1840 with [$U^{13}C$]-Glucose, [$^{15}N$]-ammonium sulfate, [$^{34}S$]-sulfate and subsequent cell extraction and labeling analysis with GC/MS confirmed that the carbon, nitrogen and sulfur content of the observed metabolite matched homolanthionine ($C_8N_2S_1$). The observed mass fragments m (m/z=692), m-15 (m/z=677), m-57 (m/z=635) of homolanthionine in GC/MS were 14 masses heavier than their counterparts in cystathionine (FIG. 3), indicating that an additional methylene group was present. Additionally, the characteristic fragments m/z=170, m/z=244 and m/z=272 of the homocysteine residue could be observed also in cystathionine, homocysteine and methionine. When metB was deleted in the genome, the resulting strain M1840 ΔMetB (corresponding to ATCC13032 ΔMcbR ΔMetB) showed only about 0.33 µmol $g_{CDW}^{-1}$ homolanthionine accumulation, close to the detection limit in the analysis. This observations unequivocally show that metB deletion leads to prevention of the formation and/or accumulation of the substance homolanthionine and thereby proves that enzymes with cystathionine γ-synthase activity such as metB will support homolanthionine accumulation which can be detrimental to methionine production.

Origin of homolanthionine in cell metabolism. Cultivation of a *C. glutamicum* ΔMcbR, Δhom, Δhsk mutant with [$U^{13}C$]-Glucose and [$U^{13}C$]-threonine and naturally labeled homoserine clearly showed that the homolanthionine was derived from homoserine. Just like homoserine the labeling of homolanthionine revealed a natural labeling pattern, indicating that neither glucose nor threonine provide necessary precursors for the homolanthionine synthesis. In additional experiments the strain was cultivated under the same conditions, except that methionine, cystathionine or homocysteine were fed instead of homoserine. These experiments showed that the strain was able to grow with these substrates, but we observed a reduced growth on cystathionine corroborating the findings of Ruckert et al., 2003, vide supra. Feeding these three substrates did not lead to significant accumulation of homolanthionine. This shows that the accumulation of this metabolite in the methionine pathway has to be located prior to homocysteine formation. MetB, MetZ or a MetC, working in the reverse direction could be regarded as possible candidates for homolanthionine forming enzymes.

Figure 2:
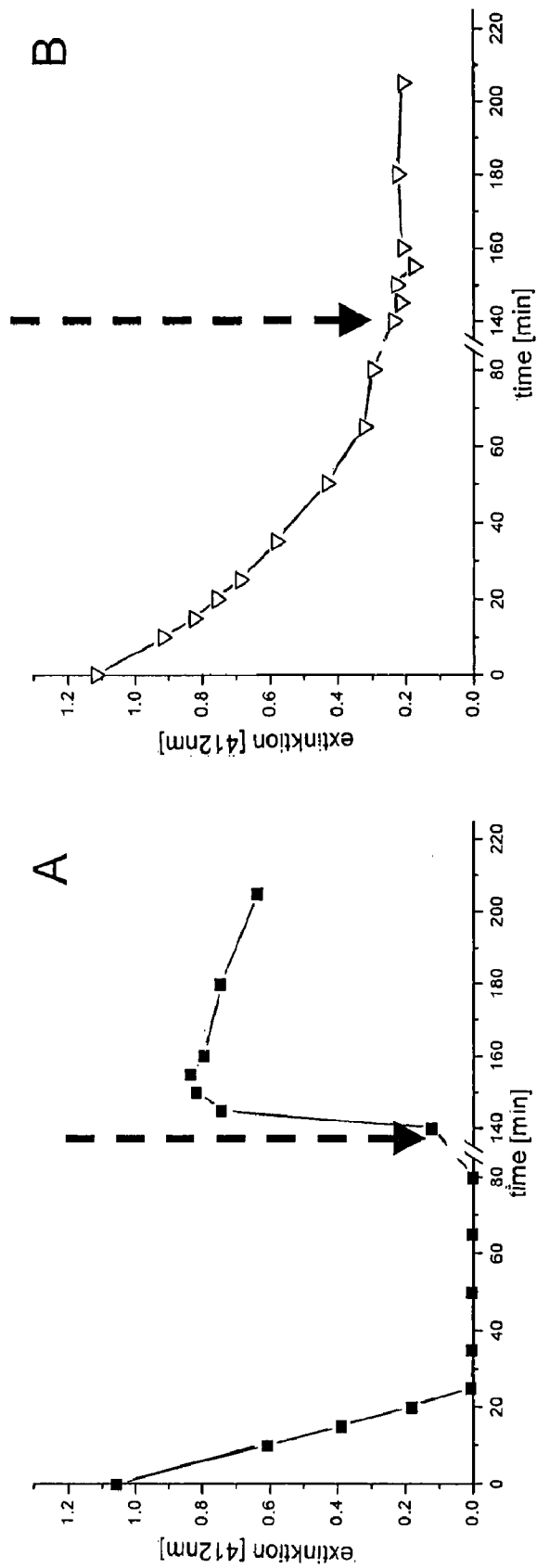
FIG. 2 shows spectra of the photometric measurement of free SH groups at 412 nm at different time points of MetC assays (FIG. 2a) and MetB assays (FIG. 2b). The break in the x-axis between 80 and 140 minutes equals the time for MetB separation by ultrafiltration. The addition of MetC is indicated by grey dashed arrows. Corresponding substrate and product concentrations, measured with HPLC are given in Table 3a and 3b, respectively.

Isolation and characterization of MetB and MetC. To further address questions concerning homolanthionine accumulation in the methionine pathway, MetB and MetC were overexpressed in *E. coli* and isolated. The isolated proteins were characterized in enzymatic assays. The $K_m$ values for their natural substrates cysteine and cystathionine, respectively are in the same range as those found for corresponding enzymes of other organisms (Table 3). The $K_m$ value of MetB for cysteine was 258 µM, whereas $K_m$ for homocysteine with 541 µM was more than double. Given equal intracellular concentrations of homocysteine and cysteine in *C. glutamicum* ΔMcbR, the observed $K_m$ values may indicate that both substrates are used in vivo by MetB. The $K_m$ of MetC for cystathionine was 107 µM, a value in between those for *E. coli* and *Salmonella* cystathioninases (Table 3). Due to the lack of pure homolanthionine, the $K_m$ value for this substrate could not be determined. But the corresponding value of the *E. coli* cystathioniase of 4.5 mM (Table 2) showed that the cleavage of homolanthionine was very poor. MetB was further characterized by incubation with o-acetyl-homoserine and cysteine or homocysteine, respectively. The consumption of cysteine (FIG. 2A) and homocysteine (FIG. 2B) was followed photometrically. Moreover samples from the enzyme assays were taken at 0 min, 80 min and 205 min and analyzed by HPLC. MetB converted cysteine and O-acetyl-homoserine effectively into cystathionine. It formed homolanthionine when incubated with O-acetyl-homoserine and homocysteine. MetB was removed from the assays after 80 min by ultrafiltration and MetC was added. The addition of MetC led to a complete cleavage of cystathionine resulting in accumulation of homocysteine, also reflected in extinction increase in the photometric assay (FIG. 2A). Homolanthionine was only poorly cleaved by MetC leading to a slight increase in homocysteine and slightly decreased homolanthionine concentration. The cleavage was to weak to be followed in the photometer. This indicated that the $K_m$ value of MetC for homolanthionine could be as high as in *E. coli*. In fact the $K_m$ values for MetC of *E. coli* for cystathionine (40 µM) and homolanthionine (4.5 mM) (Dwivedi, C. M, et al., Biochemistry 1982, 2113, 3064-9), indicate a slower cleavage of homolanthionine by MetC. Similar results were found by Uren (Uren, J. R., Methods Enzymol 1987, 143, 483-6). Interestingly, the cleavage of cystathionine and the accumulation of homocysteine also resulted in the accumulation of small amounts of homolanthionine. This indicates that MetC is also able to form homolanthionine. However, controls with O-acetyl-homoserine and homocysteine that did not contain MetB in the first place, did not yield homolanthionine, when MetC was added. This shows that MetC can not use these substrates to create homolanthionine. It is possible that homocysteine, accumulating during the cleavage of cystathionine, is used by MetC for a cystathionine-β-synthase (CysM) reaction. Instead of serine, MetC could use homoserine that is present in the assay as an impurity from O-acetyl-homoserine and thus form homolanthionine. Control assays with O-acetyl-homoserine or homocysteine alone and controls with homoserine instead of O-acetyl-homoserine did not yield any product using MetB or MetC. In addition, the hydrolytic cleavage of homolanthionine by MetC leads not only to the formation of homocysteine, but in analogy to the cystathionine cleavage also ammonia and 2-oxobutanoate should be produced. The latter is a precursor of isoleucine. This would lead to a metabolic route from methionine biosynthesis into isoleucine formation, circumventing threonine as the known sole source of isoleucine.

Impact on isoleucine metabolism. Isoleucine is formed from a $C_4$-precursor (threonine) and a $C_3$-precursor (pyruvate). In the final molecule 2 carbon atoms of isoleucine derive from pyruvate. If the $C_4$-precursor is unlabeled and pyruvate is labeled a mass shift of 2 is observed. The isoleucine fragment investigated in GC/MS contained carbon 2 to 6 of the isoleucine skeleton. When threonine and glucose were fully labeled the mass shift in m/z=200 should be m+5. If, however, the homoserine derived $C_4$ was used to form isoleucine, a shift of m+2 should be observed, deriving from the labeled pyruvate. In fact, an isoleucine formation from an alternative precursor than threonine was observed in the McbR-Knockout strains. About 13% of the proteinogenic isoleucine in C. glutamicum ΔMcbR, Δhom, Δhsk was formed from a precursor derived from naturally labeled homoserine and not from the labeled threonine provided in the culture medium (Table 3). This was observed as a 13% abundance of m+2 mass isotopomer of isoleucine (m/z=200). The proteinogenic threonine was identically labeled as the extracellular threonine and alanine reflected the pyruvate labeling, identical to the extracellular glucose labeling. It becomes obvious that C. glutamicum is able to generate isoleucine independent from threonine. The additional isoleucine precursor is most probably 2-oxobutanoate derived from the methionine metabolism. Normally this organic acid is formed in isoleucine metabolism by deamination of threonine via a threonine ammonia-lyase. In the methionine metabolism there are alternative reactions possible to form 2-oxobutanoate. A methionine methanethiol-lyase (EC 4.4.11), a homocysteine hydrogen-sulfide-lyase (EC 4.4.1.2) or a cystathionine cysteine-lyase (EC 4.4.1.1) could be responsible for the formation of 2-oxobutanoate. By feeding the mutant with either methionine, homocysteine or cystathionine and at the same time fully carbon labeled glucose and threonine these possibilities were ruled out (Table 2). Moreover, in these studies the change in isoleucine labeling was linked to the accumulation of homolanthionine, showing that the MetC-cleavage of homolanthionine is most likely responsible for the threonine independent isoleucine synthesis.

SeqID No. 1:
>pH430
```
tcgagctctccaatctccactgaggtacttaatccttccggggaattcgg
gcgcttaaatcgagaaattaggccatcacctttaataacaatacaatga
ataattggaataggtcgacacctttggagcggagccggttaaaattggca
gcattcaccgaaagaaaggagaaccacatgcttgccctaggttggatta
catggatcattattggtggtctagctggttggattgcctccaagattaaa
ggcactgatgctcagcaaggaattttgctgaacatagtcgtcggtattat
cggtggtttgttaggcggctggctgcttggaatcttcggagtggatgttg
ccggtggcggcttgatcttcagcttcatcacatgtctgattggtgctgtc
attttgctgacgatcgtgcagttcttcactcggaagaagtaatctgcttt
aaatccgtagggcctgttgatatttcgatatcaacaggcctttggtcat
tttggggtggaaaaagcgctagacttgcctgtggattaaaactatacgaa
ccggtttgtctatattggtgttagacagttcgtcgtatcttgaaacagac
caacccgaaaggacgtggccgaacgtggctgctagctaatccttgatggt
ggacttgctggatctcgattggtccacaacatcagtcctcttgagacggc
tcgcgatttggctcggcagttgttgtcggctccacctgcggactactcaa
tttagtttcttcattttccgaaggggtatcttcgttggggaggcgtcga
taagcccctcttttagctttaacctcagcgcgacgctgctttaagcgc
tgcatggcgggcgcggttcatttcacgttgcgtttcgcgcctcttgttcgc
gatttctttgcgggcctgtttgcttcgttgatttcggcagtacgggttt
tggtgagttccacgtttgttgcgtgaagcgttgaggcgttccatggggtg
agaatcatcagggcgcggttttgcgtcgtgtccacaggaagatgcgctt
ttctttttgcttgcgcggtagatgtcgcgctgctctaggtggtgcactt
tgaaatcgtcggtaagtgggtatttgcgttccaaaatgaccatcatgatg
attgtttggaggagcgtccacaggttgttgctgacgcgtcatatgactag
ttcggacctagggatatcgtcgacatcgatgctcttctgcgttaattaac
aattgggatcctctagacccgggattaaatcgctagcgggctgctaaag
gaagcggaacacgtagaaagccagtccgcagaaacggtgctgaccccgga
tgaatgtcagctactgggctatctggacaagggaaaacgcaagcgcaaag
agaaagcaggtagcttgcagtgggcttacatggcgatagctagactgggc
ggttttatggacagcaagcgaaccggaattgccagctggggcgccctctg
gtaaggttgggaagccctgcaaagtaaactggatggctttcttgccgcca
aggatctgatggcgcagggatcaagatctgatcaagagacaggatgagg
atcgtttcgcatgattgaacaagatggattgcacgcaggttctccggccg
cttgggtggagaggctattcggctatgactgggcacaacagacaatcggc
tgctctgatgccgccgtgttccggctgtcagcgcaggggcgcccggttct
tttgtcaagaccgacctgtccggtgccctgaatgaactgcaggacgagg
cagcgcggctatcgtggctggccacgacgggcgttccttgcgcagctgtg
ctcgacgttgtcactgaagcgggaagggactggctgctattgggcgaagt
gccggggcaggatctcctgtcatctcaccttgctcctgccgagaaagtat
ccatcatggctgatgcaatgcggcggctgcatacgcttgatccggctacc
tgccattcgaccaccaagcgaaacatcgcatcgagcgagcacgtactcg
gatggaagccggtcttgtcgatcaggatgatctggacgaagagcatcagg
ggctcgcgccagccgaactgttcgccaggctcaaggcgcgcatgcccgac
ggcgaggatctcgtcgtgacccatggcgatgcctgcttgccgaatatcat
ggtggaaaatggccgcttttctggattcatcgactgtggccggctgggtg
tggcggaccgctatcaggacatagcgttggctaccgtgatattgctgaa
gagcttggcggcgaatgggctgaccgcttcctcgtgcttttacggtatcgc
cgctcccgattcgcagcgcatcgccttctatcgccttcttgacgagttct
tctgagcgggactctggggttcgaaatgaccgaccaagcgacgcccaacc
tgccatcacgagatttcgattccaccgccgccttctatgaaaggttgggc
ttcggaatcgttttccgggacgccggctggatgatcctccagcgcgggga
tctcatgctggagttcttcgcccacgctagcggcgcgccggccggcccgg
tgtgaaataccgcacagatgcgtaaggagaaaataccgcatcaggcgctc
ttccgcttcctcgctcactgactcgctgcgctcggtcgttcggctgcggc
gagcggtatcagctcactcaaaggcggtaatacggttatccacagaatca
ggggataaccgcaggaaagaacatgtgagcaaaaggccagcaaaaggccag
gaaccgtaaaaaggccgcgttgctggcgttttccataggctccgcccc
ctgacgagcatcacaaaaatcgacgctcaagtcagaggtggcgaaacccg
acaggactataaagataccaggcgtttccccctggaagctccctcgtgcg
ctctcctgttccgaccctgccgcttaccggatacctgtccgcctttctcc
cttcgggaagcgtggcgctttctcatagctcacgctgtaggtatctcagt
tcggtgtaggtcgttcgctccaagctgggctgtgtgcacgaaccccccgt
tcagcccgaccgctgcgccttatccggtaactatcgtcttgagtccaacc
cggtaagacacgacttatcgccactggcagcagccactggtaacaggatt
agcagagcgaggtatgtaggcggtgctacagagttcttgaagtggtggcc
taactacggctacactagaaggacagtatttggtatctgcgctctgctga
agccagttaccttcggaaaaagagttggtagctcttgatccggcaaacaa
accaccgctggtagcggtggtttttttgtttgcaagcagcagattacgcg
cagaaaaaaaggatctcaagaagatcctttgatcttttctacgggtctg
acgctcagtggaacgaaaactcacgttaagggattttggtcatgagatta
tcaaaaaggatcttcacctagatccttttaaaggccggccgcggccgcca
tcggcattttcttttgcgttttattgttaactgttaattgtccttgtt
caaggatgctgtctttgacaacagatgttttcttgcctttgatgttcagc
aggaagctcggcgcaaacgttgattgtttgtctgcgtagaatcctctgtt
tgtcatatagcttgtaatcacgacattgtttcctttcgcttgaggtacag
cgaagtgtgagtaagtaaaggttacatcgttaggatcaagatccattttt
aacacaaggccagttttttgttcagcggcttgtatgggccagttaaagaatt
agaaacataaccaagcatgtaaatatcgttagacgtaatgccgtcaatcg
tcattttgatccgcgggagtcagtgaacaggtaccatttgccgttcatt
ttaaagacgttcgcgcgtttcaatttcatctgttactgtgttagatgcaat
cagcggtttcatcactttttttcagtgtgtaatcatcgtttagctcaatca
taccgagagcgccgtttgctaactcagccgtgcgttttttatcgctttgc
agaagttttttgactttcttgacggaagaatgatgtgcttttgccatagta
tgctttgttaaataaagattcttcgccttggtagccatcttcagttccag
tgtttgcttcaaatactaagtatttgtggcctttatcttctacgtagtga
```

-continued

```
ggatctctcagcgtatggttgtcgcctgagctgtagttgccttcatcgat
gaactgctgtacattttgatacgtttttccgtcaccgtcaaagattgatt
tataatcctctacaccgttgatgttcaaagagctgtctgatgctgatacg
ttaacttgtgcagttgtcagtgtttgtttgccgtaatgtttaccggagaa
atcagtgtagaataaacggattttccgtcagatgtaaatgtggctgaac
ctgaccattcttgtgtttggtcttttaggatagaatcatttgcatcgaat
ttgtcgctgtctttaaagacgcggcagcgttttccagctgtcaataga
agtttcgccgacttttgatagaacatgtaaatcgatgtgtcatccgcat
ttttaggatctccggctaatgcaaagacgatgtggtagccgtgatagttt
gcgacagtgccgtcagcgttttgtaatggccagctgtcccaaacgtccag
gccttttgcagaagagatatttttaattgtggacgaatcaaattcagaaa
cttgatatttttcatttttttgctgttcagggatttgcagcatatcatgg
cgtgtaatatgggaaatgccgtatgtttccttatatggcttttggttcgt
ttctttcgcaaacgcttgagttgcgcctcctgccagcagtgcggtagtaa
aggttaatactgttgcttgttttgcaaacttttttgatgttcatcgttcat
gtctcctttttatgtactgtgttagcggtctgcttcttccagccctcct
gtttgaagatggcaagttagttacgcacaataaaaaaagacctaaaatat
gtaaggggtgacgccaaagtatacacttgccctttacacattttaggtc
ttgcctgctttatcagtaacaaaccgcgcgatttacttttcgacctcat
tctattagactctcgtttggattgcaactggtctatttttcctcttttgtt
tgatagaaaatcataaaaggatttgcagactacgggcctaaagaactaaa
aaatctatctgttctttttcattctctgtatttttttatagttttctgtt gc
atgggcataaagttgcctttttaatcacaattcagaaaatatcataat
ctcattttcactaaataatagtgaacggcaggtatatgtgatgggttaaaa
aggatcggcggccgctcgatttaaatc
```

Seq ID No. 2:
>pH238
```
tcgagaggcctgacgtcgggcccggtaccacgcgtcatatgactagttcg
gacctaggatatcgtcgacatcgatgctcttctgcgttaattaacaatt
gggatccatgacctcagcatctgccccaagcttaaccccgcaaggtc
ccggctcagcagtcggaattgccctttaggattcggaacagtcggcact
gaggtgatgcgtctgatgaccgagtacggtgatgaacttgccgcaccgcat
tggtggcccactggaggttcgtggcattgctgtttctgatatctcaaagc
cacgtgaaggcgtgcacttgccttgctcactgaggacgctttgcactc
atcgagcgcgaggatgttgacatcgtcgttgaggttatcggcggcattga
gtacccacgtgaggtagttctcgcagctctgaaggccggcaagtctgttg
ttaccgccaataaggctcttgttgcagctcactctgctgagcttgctgat
gcagcggtgttaagttagtggatgggatgctcgtgagtctggcatta
aggtgcttgagctgaggttgcgggaccagtcaaggttgaagttaaccaa
ccttaggcccaacaaggaaggccccttcgaatcaagaaggggccttat
tagtgcagcaattattcgctgaacacgtgaaccttacaggtgccggcgc
gttgagtggtttgagttgcagctcggcggttgttttcaccgaggtt
cttggatgaatccggctggatggcgcagacgaaggctgatgggcgtttg
tcgttgaccacaaatgggcagctgtgtagagcgagggagtttgcttcttc
ggtttcggtgggtcaaagcccattcgcggaggcggttaatgagcgggg
agagggctcgtcgagtcttcggcgtggttaatgtaccatgacg
tgtgcccactgggttccgatggaaagtgctttggcgcggaggtcgggtt
gtgcattgcgtcatcgtcgacatcgccgagcatgttggccatgagttcga
tcaggggtgatgtattctttggcgacagcgcggttgtcggggacgcgtgtt
tggaagatgaatcctctagaccccggagttaaatcgctcagcgggctgcta
aaggaagcggaacacgtagaaagccagtccgcagaaacgggctgacccc
ggatgaatgtcagctactgggctatctggacaagggaaaacgcaagcgca
aagagaaagcaggtagcttgcagtgggcttacatggcgatagctagactg
ggcggtttttatggacagcaagcgaaccggaattgccagctgggggcgcct
ctggttaaggttgggaagccctgcaaagtaaactggatggcttcttgccg
ccaaggatctgatggcgcagggatcaagatctgatcaagagacaggatg
aggatcgtttcgcatgattgaacaagatggattgcacgcaggttctccgg
ccgcttgggtggagaggctattcggctatgactgggcacaacagacaatc
ggctgctctgatgccgccgtgttccggctgtcagcgcagggggcgcccggt
tctttttgtcaagaccgacctgtccggtgccctgaatgaactgcaggacg
aggcagcgcggctatcgtggctggccacgacgggcgttccttgcgcagct
gtgctcgacgttgtcactgaagcgggaagggactggctgctattgggcga
agtgccggggcaggatctcctgtcatctcaccttgctcctgccgagaaag
tatccatcatggctgatgcaatgcggcggctgcatacgcttgatccggct
acctgcccattcgaccaccaagcgaaacatcgcatcgagcgagcacgtac
tcggatggaagccggtcttgtcgatcaggatgatctggacgaagagcatc
aggggctcgcgccagccgaactgttcgccaggctcaaggcgcgcatgcc
cgacggcgaggatctcgtcgtgacccatggcgatgcctgcttgccgaatat
catggtggaaaatggccgcttttctggattcatcgactgtggccggctgg
gtgtggcggaccgctatcaggacatagcgttggctacccgtgatattgct
gaagagcttggcggcgaatgggctgaccgcttcctcgtgctttacggtat
cgccgctcccgattcgcagcgcatcgccttctatcgccttcttgacgagt
tcttctgagcgggactctggggttcgaaatgaccgaccaagcgacgccca
acctgccatcacgagatttcgattccaccgccgccttctatgaaaggttg
ggcttcggaatcgttttccgggacgccggctggatgatcctccagcgcgg
ggatctcatgctggagttcttcgcccaccccgggccgccgccgccgcc
cggtgtgaaataccgcacagatgcgtaaggagaaaataccgcatcaggcg
ctcttccgcttcctcgctcactgactcgctgcgctcggtcgttcggctgc
ggcgagcggtatcagctcactcaaaggcggtaatacggttatccacagaa
tcaggggataacgcaggaaagaacatgtgagcaaaaggccagcaaaaggc
```

-continued

```
caggaaccgtaaaaaggccgcgttgctggcgtttttccataggctccgcc
ccctgacgagcatcacaaaaatcgacgctcaagtcagaggtggcgaaac
ccgacaggactataaagataccaggcgtttccccctggaagctccctcgt
gcgctctcctgttccgaccctgccgcttaccggatacctgtccgcctttc
tcccttcgggaagcgtggcgctttctcatagctcacgctgtaggtatctc
agttcggtgtaggtcgttcgctccaagctgggctgtgtgcacgaaccccc
cgttcagcccgaccgctgcgccttatccggtaactatcgtcttgagtcca
acccggtaagacacgacttatcgccactggcagcagccactggtaacagg
attagcagagcgaggtatgtaggcggtgctacagagttcttgaagtggtg
gcctaactacggctacactagaaggacagtatttggtatctgcgctctgc
tgaagccagttaccttcggaaaaagagttggtagctcttgatccggcaaa
caaaccaccgctggtagcggtggttttttgtttgcaagcagcagattac
gcgcagaaaaaaaggatctcaagaagatcctttgatcttttctacggggt
ctgacgctcagtggaacgaaaactcacgttaagggattttggtcatgaga
ttatcaaaaaggatcttcacctagatcctttaaaggccgccggccg
ccatcggcattttcttttgcgttttattgttaactgttaattgtcctt
gttcaaggatgctgtctttgacaacagatgttttcttgcctttgatgttc
agcaggaagctcggcgcaacagttgattgtttgtctgcgtagaatcctct
gtttgtcatatagctcgtgtaatcacgacattgttccttcgcttgaggta
cagcgaagtgtgagtaagtaaaggttacatcgttaggatcaagatccatt
tttaacacaaggccagttttgttcagcggcttgtatgggccagttaaaga
attagaaacataaccaagcatgtaaatatcgttagacgtaatgccgtcaa
tcgtcattttgatccgcgggagtcagtgaacaggtaccattgccgttc
attttaaagacgttcgcgcgttcaatttcatctgttactgtgttagatgc
aatcagcggtttcatcacttttttcagtgtgtaatcatcgtttagctcaa
tcatacgtacgcgttgctaactcagccgtgcgttttttatcgctt
tgcagaagttttgactttcttgacggaagaatgatgtgcttttgccata
gtatgctttgttaaatataagattcttcgccttggtagccatcttcagttc
cagtgtttgcttcaaatactaagtattgtggctttatcttctacgtag
tgaggatctctcagcgtatggttgtcgcctgagctgtagttgccttcatc
gatgaactgctgtacattttgatacgtttttccgtcaccgtcaaagattg
atttataatcctctacaccgttgatgttcaaagagctgtctgatgctgat
acgttaacttgtgcagttgtcagtgtttgtttgccgtaatgtttaccgga
gaaatcagtgtagaataaacggattttccgtcagatgtaaatgtggctg
aacctgaccattcttgtgtttggtcttttaggataatcatttgcatcg
aatttgtcgctgtctttaaagacgcggcagcgttttccagctgtcaat
agaagtttcgccgacttttgatagaacatgtaaatcgatgtgtcatccg
cattttaggatctccggctaatgcaaagacgatgtggtagccgtgatag
tttgcgacagtgccgtcagcgttttgtaatggccagctgtcccaaacgtc
caggccttttgcagaagagatatttttaattgtggacgaatcaaattcag
aaacttgatatttttcatttttttgctgttcagggatttgcagcatatca
tggcgtgtaatatgggaaatgccgtatgtttccttatatggcttttggtt
cgttctttcgcaaacgcttgagttgcgcctcctgccagcagtgcggta
taaggttaatactgttgcttgttttgcaaacttttttgatgttcatcgtt
catgtctcctttttatgtactgtgttagcggtctgcttcttccagccct
cctgtttgaagatggcaagttagttacgcacaataaaaaagacctaaa
tatgtaaggggtgacgccaaagtatacacttttgcccttcacactttag
gtcttgcctgctttatcagtaacaaaccgcgcgatttacttttcgacct
cattctattagactctcgtttggattgcaactggtctatttttcctcttt
tgtttgatagaaaatcataaaaggatttgcagactacgggcctaaagaact
aaaaaatctatctgttctttttcattctctgtatttttttatagttttctgt
tgcatgggcataaagttgcctttttaatcacaattcagaaaatatcataa
tatctcatttcactaaataatagtgaacggcaggtatatgtgatgggtta
aaaaggatcggcggccgctcgatttaaatc
```

Seq ID Nr. 3:
>pSL315
```
agaggatccgactgtttcagaagtgatgactcctgaaaatttgggcgcgc
tgtatgacatgtcggtgtcgttggaaaatgtgcgcagccggtggttcgcg
ttcgatgctctgcattaaaagggctagttttacacaaaagtggcaagct
tggtctatcattgccagaagaccggtccttttcagggcatagaattctga
ttacaggagttgatctaccttgtcttttgacccaaacacccagggtttct
ccactgcatcgattcacgctgggtatgagccagacgactactacggttcg
attaacaccccaatctatgcctccaccacttcgcgcagaacgctccaaa
cgaactgcgcaaagtctacgagtacaccgtgtgggcaaccccaccatcg
tggcattagagcagaccgtcgcagcactcgaaggcgcaaagtatggccgc
gcattctcctccggcatggctgcaaccgacatcctgttccgcatcatcct
caagccgggcgcatcactctgtttaagttagtggatgggccaggtctga
agaaccacccaggccgtcaagtgcagcgaagcagatgaagcgcttcgc
ggcatgatccgtccgttcgcaggcggcgaagaagcagctaagaagtt
ctgtacctccaccaaactgatctgtctggccgagtccctcggtggcgtgg
aatccctcggagccgccaacaatgaccgaccagtcagctgccggc
tctcagtccgaggttcccgcgacctcgtcgcatctccattgtattga
agacattgaagacctgctcgcagatgtcgagcaggccctcaataaccttt
agaaactatttggcggcaagcagctttcaatataagcaatgcgagcctc
caccatgtagccgaagagttcgtcagaagttgaagcggactcttcgactg
ctttcagggtcagtggcgcttccacatctgggttctcatcaagcatgag
ttaggaaccggagcaaacatccggctttcgccctctggacgattgtc
aaaggtgtagtcggatcccgggtaccgagctcgaattcactggccgtcg
ttttacaacgtcgtgactgggaaaaccctggcgttacccaacttaatcgc
cttgcagcacatccccctttcgccagctggcgtaatagcgaagaggcccg
``` caccgatcgcccttcccaacagttgcgcagcctgaatggcgaatggcgat
aagctagcttcacgctgccgcaagcactcagggcgcaagggctgctaaag
gaagcggaacacgtagaaagccagtccgcagaaacggtgctgaccccgga
tgaatgtcagctactgggctatctggacaagggaaaacgcaagcgcaaag
agaaagcaggtagcttgcagtgggcttacatggcgatagctagactgggc
ggttttatggacagcaagcgaaccggaattgccagctggggcgccctctg
gtaaggttgggaagcctgcaaagtaaactggatggcttcttgccgcca
aggatctgatggcgcagggatcaagatctgatcaagagacaggatgagg
atcgtttcgcatgattgaacaagtggattgcacgcaggttctccggccg
cttgggtggagaggctattcggctatgactgggcacaacagacaatcggc
tgctctgatgccgccgtgttccggctgtcagcgcaggggcgcccggttct
ttttgtcaagaccgacctgtccggtgccctgaatgaactccaagacgagg
cagcgcggctatcgtggctggccacgacgggcgttccttgcgcagctgtg
ctcgacgttgtcactgaagcgggaagggactggctgctattgggcgaagt
gccggggcaggatctcctgtcatctcaccttgctcctgccgagaaagtat
ccatcatggctgatgcaatgcggcggctgcatacgcttgatccggctacc
tgcccattcgaccaccaagcgaaacatcgcatcgagcgagcacgtactcg
gatggaagccggtcttgtcgatcaggatgatctggacgaagagcatcagg
ggctcgcgccagccgaactgttcgccaggctcaaggcgcggatgcccgac
ggcgaggatctcgtcgtgacccatggcgatgcctgcttgccgaatatcat
ggtggaaaatggccgcttttctggattcatcgactgtggccggctgggtg
tggcggaccgctatcaggacatagcgttgctacccgtgatattgctgaa
gagcttggcggcgaatgggctgaccgcttcctcgtgctttacggtatcgc
cgctcccgattcgcagcgcatcgccttctatcgccttcttgacgagttct
tctgagcgggactctggggttcgctagaggatcgatccttttttaaccccat
cacatatacctgccgttcactattatttagtgaaatgagatattatgata
ttttctgaattgtgattaaaaaggcaacttttatgcccatgcaacagaaac
tataaaaaatacagagatgaaaagaaacagatagatttttttagttcttta
ggcccgtagtctgcaaatccttttatgattttctatcaaacaaaagagga
aaatagaccagttgcaatccaaacgagagtctaatagaatgaggtcgaaa
agtaaatcgcgcgggtttgttactgataaagcaggcaagacctaaaatgt
gtaaagggcaaagtgtatactttggcgtcaccccttacatattttaggtc
ttttttttattgtgcgtaactaaacttgccatcttcaaacaggagggctgg
aagaagcagaccgctaacacagtacataaaaaaggagactgaacgatga
acatcaaaaagtttgcaaaacaagcaacagtattaaccttttactaccgca
ctgctggcaggaggcgcaactcaagcgtttgcgaaagaaacgaaccaaaa
gccatataaggaaacatacggcatttcccatattacacgccatgatatgc
tgcaaatccctgaacagcaaaaaaatgaaaaatatcaagtttctgaattt
gattcgtccacaattcaactctcttctgcaaaagccctggacgttgctg
ggacagctggccattacaaaacgctgacggcactgtcgcaaactatcacg
gctaccacatcgtctttgcattagccggagatcctaaaaatgcggatgac
acatcgatttacatgttctatcaaaaagtcggcgaaacttctattgacag
ctggaaaaacgctggcccgcttcttaaagacagcgacaaattcgatgcaa
atgattctatcctaaaagaccaaacacaagaatggtcaggttcagccaca
tttacatctgacggaaaaatccgtttattctacactgatttctccggtaa
acattacggcaaacaaacactgacaactgcacaagttaacgtatcagcat
cagacagctctttgaacatcaagcgtgtagaggattataaataatcattctt
gacggtgacggaaaaacgtatcaaaatgtacagcagttcatcgatgaagg
caactacagctcaggcgacaaccatacgctgagagatcctcactacgtag
aagataaaggccacaaatacttagtatttgaagcaaacactggaactgaa
gatggctaccaaggcgagaatcttttatttaacaaagcatactatgcaa
aagcacatcattcttccgtcaagaaagtcaaaaacttctgcaaagcgata
aaaaacgcacggctgagttagcaaacggcgctctcggtatgattgagcta
aacgatgattacacactgaaaaaagtgatgaaaccgctgattgcatctaa
cacagtaacagatgaaattgaacgcgcgaacgtctttaaaatgaacggca
aatggtacctgttcactgactcccgcggatcaaaaatgacgattgacggc
attacgtctaacgatatttacatgcttggttatgtttctaattctttaac
tggcccatacaagccgctgaacaaaactggccttgtgttaaaaatggatc
ttgatcctaacgatgtaacctttacttactcacacttcgctgtacctcaa
gcgaaaggaaacaatgtcgtgattacaagctatatgacaaacagaggatt
ctacgcagacaaacaatcaacgtttgcgccgagcttcctgctgaacatca
aaggcaagaaaacatctgttgtcaaagacagcatccttgaacaaggacaa
ttaacagttaacaaataaaaacgcaaaagaaaatgccgatgggtaccgag
cgaaatgaccgaccaagcgacgcccaacctgccatcacgagatttcgatt
ccaccgccgccttctatgaaaggttgggcttcggaatcgttttccgggac
gccctcgcggacgtgctcatagtccacgacgcccgtgattttgtagccct
ggccgacggccagcaggtaggccgacaggctcatgccgccgccgccgcc
ttttcctcaatcgctcttcgttcgtctggaaggcagtacaccttgatagg
tgggctgcccttcctggttggcttggtttcatcagccatccgcttgccct
catctgttacgccggcggtagccgccagcctcgcagagcaggattcccg
ttgagcaccgccaggtgcgaataaggacagtgaagaaggaacacccgct
cgcgggtgggcctacttcacctatcctgcccggctgacgccgttggatac
accaaggaaagtctacacgaacccttggcaaaatcctgtatatcgtgcg
aaaaaggatggatatacggaaaaatcgctataatgacccgaagcaggg
ttatgcagcggaaaagcgctgcttccctgctgttttgtggaatatctacc
gactggaaacaggcaaatgcaggaaattactgaactgagggggacaggcga
gagacgatgccaaagagctcctgaaaatctcgataactcaaaaaatacgc
ccggtagtgatctttatttcatatgtgaagttggaacctcttacgtgc
cgatcaacgtctcattttcgccaaaagttggcccagggcttcccggtatc
aacagggacaccaggatttatttattctgcgaagtgatcttccgtcacag
gtatttattcggcgcaaagtgcgtcgggtgatgctgccaacttactgatt
tagtgtatgatggtgtttttgaggtgctccagtggcttctgtttctatcagggctggatgatctcc
gctcctgaaaatctcgataactcaaaaaatacgccggtagtgatcttat
ttcattatggtgaaagttggaacctcttacgtgccgatcaacgtctcatt
ttcgccaaaagttggcccagggcttcccggtatcaacagggacaccagga
tttatttattctgcgaagtgatcttccgtcacaggtatttattcggcgca
aagtgcgtcgggtgatgctgccaacttactgatttagtgtatgatggtgt
ttttgaggtgctccagtggcttctgtttctatcagggctggatgatctcc
agcgcggggatctcatgctggagtcttcgcccaccccaaaaggatctag
gtgaagatcctttttgataatctcatgaccaaaatcccttaacgtgagtt
ttcgttccactgagcgtcagaccccgtagaaaagatcaaaggatcttctt
gagatcctttttttctgcgcgtaatctgctgcttgcaaacaaaaaaacca
ccgctaccagcggtggtttgtttgccggatcaagagctaccaactctttt
tccgaaggtaactggcttcagcagagcgcagataccaaatactgttcttc
tagtgtagccgtagttaggccaccacttcaagaactctgtagcaccgcct
acatacctcgctctgctaatcctgttaccagtggctgctgccagtggcga
taagtcgtgtcttaccgggttggactcaagacgatagttaccggataagg
cgcagcggtcgggctgaacggggggttcgtgcacacagcccagcttggag
cgaacgacctacaccgaactgagatacctacagcgtgagctatgagaaag
cgccacgcttcccgaagggagaaaggcggacaggtatccggtaagcggca
gggtcggaacaggagagcgcacgagggagcttccaggggaaacgcctgg
tatctttatagtcctgtcgggtttcgccacctctgacttgagcgtcgatt
tttgtgatgctcgtcaggggggcggagcctatggaaaaacgccagcaacg
cggcctttttacggttcctggccttttgctggccttttgctcacatgttc
tttcctgcgttatcccctgattctgtggataaccgtattaccgcctttga
gtgagctgataccgctcgccgcagccgaacgaccgagcgcagcgagtcag
tgagcgaggaagcggaagagcgcccaatacgcaaaccgcctctccccgcg
cgttggccgattcattaatgcagctggcacgacaggtttcccgactggaa
agcgggcagtgagcgcaacgcaattaatgtgagttagctcactcattagg
caccccaggctttacactttatgcttccggctcgtatgttgtgtggaatt
gtgagcggataacaatttcacacaggaaacagctatgaccatgattacgc
caagcttgcatgcctgcaggtcgactct

The invention claimed is:

1. A process for the preparation of L-methionine, which comprises the following steps:
cultivating and/or fermenting a microorganism, wherein said microorganism is a *Corynebacterium glutamicum* cell that has its endogenous mcrB and metB genes disrupted by a deletion or an insertion, wherein said microorganism produces or overproduces L-methionine and in which the formation and/or accumulation of homolanthionine in the methionine pathway is reduced and/or prevented, wherein the production of an endogenous transcriptional regulator protein (McbR) is reduced compared to that of the corresponding wild-type microorganism, and the microorganism
 (a) has introduced therein a heterologous gene coding for a cystathionine-β-lyase (MetC) mutant which is capable of efficiently converting homolanthionine into homocysteine,
 (b) has introduced therein a heterologous gene coding for a cystathionine-γ-synthase (MetB) mutant which is capable of efficiently converting O-acetyl-homoserine and cysteine into cystathione and which is not capable of converting O-acetyl-homoserine and homocysteine into homolanthionine, or
 (c) produces more of a protein selected from the group consisting of a protein having the activity of cob(I)alamin dependent methionine synthase I (MetH), and cob(I)alamin independent methionine synthase II (MetE) than the corresponding wild-type microorganism; and
isolating L-methionine.

2. The process of claim 1, wherein the production of an endogenous cystathionine-γ-synthase (MetB) is reduced compared to the corresponding wild-type microorganism.

3. The process of claim 2, wherein an endogenous gene which codes for cystathionine-γ-synthase (MetB) is disrupted or eliminated.

4. The process of claim 3, wherein the disrupted endogenous gene results in the expression of a non-functional cystathionine-γ-synthase (MetB) protein in the cultivated microorganism.

5. The process of claim 1, wherein an endogenous gene which codes for transcriptional regulator protein (McbR) is disrupted and/or eliminated.

6. The process of claim 5, wherein the disrupted endogenous gene results in the expression of a non-functional transcriptional regulator protein (McbR) protein.

7. The process of claim 1, wherein expression of a protein selected from the group consisting of a protein having the activity of cob(I)alamin dependent methionine synthase I (MetH), and cob(I)alamin independent methionine synthase II (MetE) is increased as compared to the corresponding wild-type microorganism.

8. The process of claim 1, wherein L-methionine is concentrated in the medium or in the microorganism.

9. A process for the preparation of a L-methionine containing animal feedstuffs additive from fermentation broths, comprising the following steps:
cultivating and/or fermenting a microorganism, wherein said microorganism is a *Corynebacterium glutamicum* cell that has its endogenous mcrB and metB genes disrupted by a deletion or an insertion, wherein said microorganism produces or overproduces L-methionine and in which the formation and/or accumulation of homolanthionine in the methionine pathway is reduced and/or prevented;

wherein the microorganism
- (a) has introduced therein a heterologous gene coding for a cystathionine-β-lyase (MetC) mutant which is capable of efficiently converting homolanthionine into homocysteine,
- (b) has introduced therein a heterologous gene coding for a cystathionine-γ-synthase (MetB) mutant which is capable of efficiently converting O-acetyl-homoserine and cysteine into cystathione and which is not capable of converting O-acetyl-homoserine and homocysteine into homolanthionine, or
- (c) produces more of a protein selected from the group consisting of a protein having the activity of cob(I)alamin dependent methionine synthase I (MetH), and cob(I)alamin independent methionine synthase II (MetE) than the corresponding wild-type microorganism;

removing water from the L-methionine-containing fermentation broth; removing an amount of 0 to 100 wt. % of the biomass formed during fermentation; and drying the fermentation broth to obtain the animal feedstuffs additive in powder or granule form.

* * * * *

SEQUENCE LISTING

<160> NUMBER OF SEQ ID NOS: 3

<210> SEQ ID NO 1
<211> LENGTH: 5477
<212> TYPE: DNA
<213> ORGANISM: Artificial
<220> FEATURE:
<223> OTHER INFORMATION: plasmid DNA

<400> SEQUENCE: 1
tcgagctctc caatctccac tgaggtactt aatccttccg gggaattcgg gcgcttaaat      60
cgagaaatta ggccatcacc ttttaataac aatacaatga ataattggaa taggtcgaca     120
cctttggagc ggagccggtt aaaattggca gcattcaccg aaagaaaagg agaaccacat     180

| | |
|---|---|
| gcttgcccta ggttggatta catggatcat tattggtggt ctagctggtt ggattgcctc | 240 |
| caagattaaa ggcactgatg ctcagcaagg aattttgctg aacatagtcg tcggtattat | 300 |
| cggtggtttg ttaggcggct ggctgcttgg aatcttcgga gtggatgttg ccggtggcgg | 360 |
| cttgatcttc agcttcatca catgtctgat tggtgctgtc attttgctga cgatcgtgca | 420 |
| gttcttcact cggaagaagt aatctgcttt aaatccgtag ggcctgttga tatttcgata | 480 |
| tcaacaggcc ttttggtcat tttggggtgg aaaaagcgct agacttgcct gtggattaaa | 540 |
| actatacgaa ccggtttgtc tatattggtg ttagacagtt cgtcgtatct tgaaacagac | 600 |
| caacccgaaa ggacgtggcc gaacgtggct gctagctaat ccttgatggt ggacttgctg | 660 |
| gatctcgatt ggtccacaac atcagtcctc ttgagacggc tcgcgatttg ctcggcagt | 720 |
| tgttgtcggc tccacctgcg gactactcaa tttagtttct tcattttccg aaggggtatc | 780 |
| ttcgttgggg gaggcgtcga taagccccett cttttagct ttaacctcag cgcgacgctg | 840 |
| ctttaagcgc tgcatggcgg cgcggttcat ttcacgttgc gtttcgcgcc tcttgttcgc | 900 |
| gatttctttg cgggcctgtt ttgcttcgtt gatttcggca gtacgggttt tggtgagttc | 960 |
| cacgtttgtt gcgtgaagcg ttgaggcgtt ccatggggtg agaatcatca gggcgcggtt | 1020 |
| tttgcgtcgt gtccacagga agatgcgctt ttctttttgt tttgcgcggt agatgtcgcg | 1080 |
| ctgctctagg tggtgcactt tgaaatcgtc ggtaagtggg tatttgcgtt ccaaaatgac | 1140 |
| catcatgatg attgtttgga ggagcgtcca caggttgttg ctgacgcgtc atatgactag | 1200 |
| ttcggaccta gggatatcgt cgacatcgat gctcttctgc gttaattaac aattgggatc | 1260 |
| ctctagaccc gggatttaaa tcgctagcgg gctgctaaag gaagcggaac acgtagaaag | 1320 |
| ccagtccgca gaaacggtgc tgaccccgga tgaatgtcag ctactgggct atctggacaa | 1380 |
| gggaaaacgc aagcgcaaag agaaagcagg tagcttgcag tgggcttaca tggcgatagc | 1440 |
| tagactgggc ggttttatgg acagcaagcg aaccggaatt gccagctggg gcgccctctg | 1500 |
| gtaaggttgg gaagccctgc aaagtaaact ggatggcttt cttgccgcca aggatctgat | 1560 |
| ggcgcagggg atcaagatct gatcaagaga caggatgagg atcgtttcgc atgattgaac | 1620 |
| aagatggatt gcacgcaggt tctccggccg cttgggtgga gaggctattc ggctatgact | 1680 |
| gggcacaaca gacaatcggc tgctctgatg ccgccgtgtt ccggctgtca gcgcaggggc | 1740 |
| gcccggttct ttttgtcaag accgacctgt ccggtgccct gaatgaactg caggacgagg | 1800 |
| cagcgcggct atcgtggctg gccacgacgg gcgttccttg cgcagctgtg ctcgacgttg | 1860 |
| tcactgaagc gggaagggac tggctgctat tgggcgaagt gccggggcag gatctcctgt | 1920 |
| catctcacct tgctcctgcc gagaaagtat ccatcatggc tgatgcaatg cggcggctgc | 1980 |
| atacgcttga tccggctacc tgcccattcg accaccaagc gaaacatcgc atcgagcgag | 2040 |
| cacgtactcg gatggaagcc ggtcttgtcg atcaggatga tctggacgaa gagcatcagg | 2100 |
| ggctcgcgcc agccgaactg ttcgccaggc tcaaggcgcg catgcccgac ggcgaggatc | 2160 |
| tcgtcgtgac ccatggcgat gcctgcttgc cgaatatcat ggtggaaaat ggccgctttt | 2220 |
| ctggattcat cgactgtggc cggctgggtg tggcggaccg ctatcaggac atagcgttgg | 2280 |
| ctacccgtga tattgctgaa gagcttggcg gcgaatgggc tgaccgcttc ctcgtgcttt | 2340 |
| acggtatcgc cgctcccgat tcgcagcgca tcgccttcta tcgccttctt gacgagttct | 2400 |
| tctgagcggg actctggggt tcgaaatgac cgaccaagcg acgcccaacc tgccatcacg | 2460 |
| agatttcgat tccaccgccg ccttctatga aaggttgggc ttcggaatcg ttttccggga | 2520 |
| cgccggctgg atgatcctcc agcgcgggga tctcatgctg gagttcttcg cccacgctag | 2580 |

```
cggcgcgccg gccggcccgg tgtgaaatac cgcacagatg cgtaaggaga aaataccgca   2640
tcaggcgctc ttccgcttcc tcgctcactg actcgctgcg ctcggtcgtt cggctgcggc   2700
gagcggtatc agctcactca aaggcggtaa tacggttatc cacagaatca ggggataacg   2760
caggaaagaa catgtgagca aaaggccagc aaaaggccag gaaccgtaaa aaggccgcgt   2820
tgctggcgtt tttccatagg ctccgccccc ctgacgagca tcacaaaaat cgacgctcaa   2880
gtcagaggtg gcgaaacccg acaggactat aaagatacca ggcgtttccc cctggaagct   2940
ccctcgtgcg ctctcctgtt ccgaccctgc cgcttaccgg atacctgtcc gcctttctcc   3000
cttcgggaag cgtggcgctt tctcatagct cacgctgtag gtatctcagt tcggtgtagg   3060
tcgttcgctc caagctgggc tgtgtgcacg aaccccccgt tcagcccgac cgctgcgcct   3120
tatccggtaa ctatcgtctt gagtccaacc cggtaagaca cgacttatcg ccactggcag   3180
cagccactgg taacaggatt agcagagcga ggtatgtagg cggtgctaca gagttcttga   3240
agtggtggcc taactacggc tacactagaa ggacagtatt tggtatctgc gctctgctga   3300
agccagttac cttcggaaaa agagttggta gctcttgatc cggcaaacaa accaccgctg   3360
gtagcggtgg tttttttgtt tgcaagcagc agattacgcg cagaaaaaaa ggatctcaag   3420
aagatccttt gatcttttct acggggtctg acgctcagtg gaacgaaaac tcacgttaag   3480
ggattttggt catgagatta tcaaaaagga tcttcaccta gatcctttta aaggccggcc   3540
gcggccgcca tcggcatttt cttttgcgtt tttatttgtt aactgttaat tgtccttgtt   3600
caaggatgct gtctttgaca acagatgttt tcttgccttt gatgttcagc aggaagctcg   3660
gcgcaaacgt tgattgtttg tctgcgtaga atcctctgtt tgtcatatag cttgtaatca   3720
cgacattgtt tccttttcgct tgaggtacag cgaagtgtga gtaagtaaag gttacatcgt   3780
taggatcaag atccattttt aacacaaggc cagttttgtt cagcggcttg tatgggccag   3840
ttaaagaatt agaaacataa ccaagcatgt aaatatcgtt agacgtaatg ccgtcaatcg   3900
tcatttttga tccgcgggag tcagtgaaca ggtaccattt gccgttcatt ttaaagacgt   3960
tcgcgcgttc aatttcatct gttactgtgt tagatgcaat cagcggtttc atcactttttt   4020 tcagtgtgta atcatcgttt agctcaatca taccgagagc gccgtttgct aactcagccg   4080
tgcgtttttt atcgctttgc agaagttttt gactttcttg acggaagaat gatgtgcttt   4140
tgccatagta tgctttgtta aataaagatt cttcgccttg gtagccatct tcagttccag   4200
tgtttgcttc aaatactaag tatttgtggc ctttatcttc tacgtagtga ggatctctca   4260
gcgtatggtt gtcgcctgag ctgtagttgc cttcatcgat gaactgctgt acatttttgat   4320 acgttttcc gtcaccgtca aagattgatt tataatcctc tacaccgttg atgttcaaag   4380
agctgtctga tgctgatacg ttaacttgtg cagttgtcag tgtttgtttg ccgtaatgtt   4440
taccggagaa atcagtgtag aataaacgga ttttccgtc agatgtaaat gtggctgaac   4500
ctgaccattc ttgtgtttgg tcttttagga tagaatcatt tgcatcgaat ttgtcgctgt   4560 cttttaaagac gcggccagcg ttttccagc tgtcaataga agtttcgccg acttttttgat   4620 agaacatgta aatcgatgtg tcatccgcat ttttaggatc tccggctaat gcaaagacga   4680
tgtggtagcc gtgatagttt gcgacagtgc cgtcagcgtt ttgtaatggc cagctgtccc   4740
aaacgtccag gccttttgca gaagagatat ttttaattgt ggacgaatca aattcagaaa   4800 cttgatatttt tcattttttt tgctgttcag ggatttgcag catatcatgg cgtgtaatat   4860
gggaaatgcc gtatgtttcc ttatatggct tttggttcgt ttctttcgca aacgcttgag   4920
ttgcgcctcc tgccagcagt gcggtagtaa aggttaatac tgttgcttgt tttgcaaact   4980
```

-continued

| | | |
|---|---|---|
| ttttgatgtt catcgttcat gtctcctttt ttatgtactg tgttagcggt ctgcttcttc | 5040 |
| cagccctcct gtttgaagat ggcaagttag ttacgcacaa taaaaaaaga cctaaaatat | 5100 |
| gtaaggggtg acgccaaagt atacactttg cccttacac atttaggtc ttgcctgctt | 5160 |
| tatcagtaac aaacccgcgc gatttacttt tcgacctcat tctattagac tctcgtttgg | 5220 |
| attgcaactg gtctattttc ctcttttgtt tgatagaaaa tcataaaagg atttgcagac | 5280 |
| tacgggccta agaactaaa aaatctatct gtttcttttc attctctgta tttttatag | 5340 |
| tttctgttgc atgggcataa agttgccttt ttaatcacaa ttcagaaaat atcataatat | 5400 |
| ctcatttcac taaataatag tgaacggcag gtatatgtga tgggttaaaa aggatcggcg | 5460 |
| gccgctcgat ttaaatc | 5477 |

<210> SEQ ID NO 2
<211> LENGTH: 5330
<212> TYPE: DNA
<213> ORGANISM: Artificial
<220> FEATURE:
<223> OTHER INFORMATION: plasmid DNA

<400> SEQUENCE: 2

| | | |
|---|---|---|
| tcgagaggcc tgacgtcggg cccggtacca cgcgtcatat gactagttcg gacctaggga | 60 |
| tatcgtcgac atcgatgctc ttctgcgtta attaacaatt gggatccatg acctcagcat | 120 |
| ctgccccaag ctttaacccc ggcaagggtc ccggctcagc agtcggaatt gccctttag | 180 |
| gattcggaac agtcggcact gaggtgatgc gtctgatgac cgagtacggt gatgaacttg | 240 |
| cgcaccgcat tggtggccca ctggaggttc gtggcattgc tgtttctgat atctcaaagc | 300 |
| cacgtgaagg cgttgcacct gagctgctca ctgaggacgc ttttgcactc atcgagcgcg | 360 |
| aggatgttga catcgtcgtt gaggttatcg gcggcattga gtacccacgt gaggtagttc | 420 |
| tcgcagctct gaaggccggc aagtctgttg ttaccgccaa taaggctctt gttgcagctc | 480 |
| actctgctga gcttgctgat gcagcggtgt ttaagtttag tggatgggga tgctcgtgag | 540 |
| tctggcatta aggtgcttga gcttgaggtt gcgggaccag tcaaggttga agttaaccaa | 600 |
| ccttaggccc aacaaggaag gccccttcg aatcaagaag ggggccttat tagtgcagca | 660 |
| attattcgct gaacacgtga accttacagg tgcccggcgc gttgagtggt ttgagttcca | 720 |
| gctggatgcg gttgttttca ccgaggcttt cttggatgaa tccggcgtgg atggcgcaga | 780 |
| cgaaggctga tgggcgtttg tcgttgacca caaatgggca gctgtgtaga gcgagggagt | 840 |
| ttgcttcttc ggtttcggtg gggtcaaagc ccatttcgcg gaggcggtta atgagcgggg | 900 |
| agagggcttc gtcgagttct tcggcttcgg cgtggttaat gcccatgacg tgtgcccact | 960 |
| gggttccgat ggaaagtgct ttggcgcgga ggtcggggtt gtgcattgcg tcatcgtcga | 1020 |
| catcgccgag catgttggcc atgagttcga tcagggtgat gtattctttg gcgacagcgc | 1080 |
| ggttgtcggg gacgcgtgtt tggaagatgg atcctctaga cccgggattt aaatcgctag | 1140 |
| cgggctgcta aaggaagcgg aacacgtaga aagccagtcc gcagaaacgg tgctgacccc | 1200 |
| ggatgaatgt cagctactgg gctatctgga caagggaaaa cgcaagcgca agagaaagc | 1260 |
| aggtagcttg cagtgggctt acatggcgat agctagactg ggcggtttta tggacagcaa | 1320 |
| gcgaaccgga attgccagct ggggcgccct ctggtaaggt tgggaagccc tgcaaagtaa | 1380 |
| actggatggc tttcttgccg ccaaggatct gatgcgcag gggatcaaga tctgatcaag | 1440 |
| agacaggatg aggatcgttt cgcatgattg aacaagatgg attgcacgca ggttctccgg | 1500 |
| ccgcttgggt ggagaggcta ttcggctatg actgggcaca acagacaatc ggctgctctg | 1560 |

```
atgccgccgt gttccggctg tcagcgcagg ggcgcccggt tcttttttgtc aagaccgacc    1620 tgtccggtgc cctgaatgaa ctgcaggacg aggcagcgcg gctatcgtgg ctggccacga    1680
cgggcgttcc ttgcgcagct gtgctcgacg ttgtcactga agcgggaagg gactggctgc    1740
tattgggcga agtgccgggg caggatctcc tgtcatctca ccttgctcct gccgagaaag    1800
tatccatcat ggctgatgca atgcggcggc tgcatacgct tgatccggct acctgcccat    1860
tcgaccacca agcgaaacat cgcatcgagc gagcacgtac tcggatggaa gccggtcttg    1920
tcgatcagga tgatctggac gaagagcatc aggggctcgc gccagccgaa ctgttcgcca    1980
ggctcaaggc gcgcatgccc gacggcgagg atctcgtcgt gacccatggc gatgcctgct    2040
tgccgaatat catggtggaa aatggccgct tttctggatt catcgactgt ggccggctgg    2100
gtgtggcgga ccgctatcag gacatagcgt tggctacccg tgatattgct gaagagcttg    2160
gcggcgaatg ggctgaccgc ttcctcgtgc tttacggtat cgccgctccc gattcgcagc    2220
gcatcgcctt ctatcgcctt cttgacgagt tcttctgagc gggactctgg ggttcgaaat    2280
gaccgaccaa gcgacgccca acctgccatc acgagatttc gattccaccg ccgccttcta    2340
tgaaaggttg ggcttcggaa tcgttttccg gacgccggc tggatgatcc tccagcgcgg    2400
ggatctcatg ctggagttct cgcccacgc tagcggcgcg ccggccggcc cggtgtgaaa    2460
taccgcacag atgcgtaagg agaaaatacc gcatcaggcg ctcttccgct tcctcgctca    2520
ctgactcgct gcgctcggtc gttcggctgc ggcgagcggt atcagctcac tcaaaggcgg    2580
taatacggtt atccacagaa tcaggggata acgcaggaaa gaacatgtga gcaaaaggcc    2640
agcaaaaggc caggaaccgt aaaaaggccg cgttgctggc gttttttccat aggctccgcc    2700 cccctgacga gcatcacaaa aatcgacgct caagtcagag gtggcgaaac ccgacaggac    2760
tataaagata ccaggcgttt cccctggaa gctccctcgt gcgctctcct gttccgaccc    2820
tgccgcttac cggatacctg tccgcctttc tcccttcggg aagcgtggcg ctttctcata    2880
gctcacgctg taggtatctc agttcggtgt aggtcgttcg ctccaagctg ggctgtgtgc    2940
acgaaccccc cgttcagccc gaccgctgcg ccttatccgg taactatcgt cttgagtcca    3000
acccggtaag acacgactta tcgccactgg cagcagccac tggtaacagg attagcagag    3060
cgaggtatgt aggcggtgct acagagttct tgaagtggtg gcctaactac ggctacacta    3120
gaaggacagt atttggtatc tgcgctctgc tgaagccagt taccttcgga aaaagagttg    3180
gtagctcttg atccggcaaa caaaccaccg ctggtagcgg tggttttttt gtttgcaagc    3240
agcagattac gcgcagaaaa aaaggatctc aagaagatcc tttgatcttt tctacggggt    3300
ctgacgctca gtggaacgaa aactcacgtt aagggatttt ggtcatgaga ttatcaaaaa    3360
ggatcttcac ctagatcctt ttaaaggccg gcgcggccg ccatcggcat tttcttttgc    3420 gttttttattt gttaactgtt aattgtcctt gttcaaggat gctgtctttg acaacagatg    3480
ttttcttgcc tttgatgttc agcaggaagc tcggcgcaaa cgttgattgt ttgtctgcgt    3540
agaatcctct gtttgtcata tagcttgtaa tcacgacatt gttttccttttc gcttgaggta    3600 cagcgaagtg tgagtaagta aaggttacat cgttaggatc aagatccatt tttaacacaa    3660
ggccagtttt gttcagcggc ttgtatgggc cagttaaaga attagaaaca taaccaagca    3720
tgtaaatatc gttagacgta atgccgtcaa tcgtcatttt tgatccgcgg gagtcagtga    3780
acaggtacca tttgccgttc attttaaaga cgttcgcgcg ttcaatttca tctgttactg    3840
tgttagatgc aatcagcggt ttcatcactt ttttcagtgt gtaatcatcg tttagctcaa    3900
tcataccgag agcgccgttt gctaactcag ccgtgcgttt tttatcgctt tgcagaagtt    3960
```

-continued

```
tttgactttc ttgacggaag aatgatgtgc ttttgccata gtatgctttg ttaaataaag    4020
attcttcgcc ttggtagcca tcttcagttc cagtgtttgc ttcaaatact aagtatttgt    4080
ggcctttatc ttctacgtag tgaggatctc tcagcgtatg gttgtcgcct gagctgtagt    4140
tgccttcatc gatgaactgc tgtacatttt gatacgtttt tccgtcaccg tcaaagattg    4200
atttataatc ctctacaccg ttgatgttca aagagctgtc tgatgctgat acgttaactt    4260
gtgcagttgt cagtgtttgt ttgccgtaat gtttaccgga gaaatcagtg tagaataaac    4320 ggattttttcc gtcagatgta aatgtggctg aacctgacca ttcttgtgtt tggtctttta    4380
ggatagaatc atttgcatcg aatttgtcgc tgtctttaaa gacgcggcca gcgttttttcc    4440 agctgtcaat agaagtttcg ccgactttt gatagaacat gtaaatcgat gtgtcatccg    4500 cattttagg atctccggct aatgcaaaga cgatgtggta gccgtgatag tttgcgacag    4560
tgccgtcagc gttttgtaat ggccagctgt cccaaacgtc caggccttt gcagaagaga    4620 tatttttaat tgtggacgaa tcaaattcag aaacttgata ttttttcattt ttttgctgtt    4680 cagggatttg cagcatatca tggcgtgtaa tatgggaaat gccgtatgtt tccttatatg    4740
gcttttggtt cgtttctttc gcaaacgctt gagttgcgcc tcctgccagc agtgcggtag    4800
taaaggttaa tactgttgct tgttttgcaa acttttttgat gttcatcgtt catgtctcct    4860
tttttatgta ctgtgttagc ggtctgcttc ttccagccct cctgtttgaa gatggcaagt    4920
tagttacgca caataaaaaa agacctaaaa tatgtaaggg gtgacgccaa agtatacact    4980 ttgccctta cacattttag gtcttgcctg ctttatcagt aacaaacccg cgcgatttac    5040
ttttcgacct cattctatta gactctcgtt tggattgcaa ctggtctatt ttcctcttt    5100 gtttgataga aaatcataaa aggatttgca gactacgggc taaagaact aaaaaatcta    5160 tctgtttctt ttcattctct gtattttta gtttctgt tgcatgggca taaagttgcc    5220 ttttaatca caattcagaa aatatcataa tatctcattt cactaaataa tagtgaacgg    5280
caggtatatg tgatgggtta aaaaggatcg gcggccgctc gatttaaatc            5330
```

<210> SEQ ID NO 3
<211> LENGTH: 6779
<212> TYPE: DNA
<213> ORGANISM: Artificial
<220> FEATURE:
<223> OTHER INFORMATION: plasmid DNA

<400> SEQUENCE: 3

```
agaggatccg actgtttcag aagtgatgac tcctgaaaat ttgggcgcgc tgtatgacat      60
gtcggtgtcg ttggaaactg tgcgcagccg gtggttcgcg ttcgatgctc tgcattaaaa     120
ggggctagtt ttacacaaaa gtggacagct tggtctatca ttgccagaag accggtcctt     180
ttagggccat agaattctga ttacaggagt tgatctacct tgtcttttga cccaaacacc     240
cagggtttct ccactgcatc gattcacgct gggtatgagc cagacgacta ctacggttcg     300
attaacaccc caatctatgc ctccaccacc ttcgcgcaga acgctccaaa cgaactgcgc     360
aaaggctacg agtacacccg tgtgggcaac cccaccatcg tggcattaga gcagaccgtc     420
gcagcactcg aaggcgcaaa gtatggccgc gcattctcct ccggcatggc tgcaaccgac     480
atcctgttcc gcatcatcct caagccgggc gatcacatct gtttaagttt agtggatggg     540
ccaggtctga agaaccaccc aggccacgaa gtcgcagcga agcagatgaa gcgcttcggc     600
ggcatgatct ccgtccgttt cgcaggcggg gaagaagcag ctaagaagtt ctgtacctcc     660
accaaactga tctgtctggc cgagtccctc ggtggcgtgg aatccctcct ggagcaccca     720
```

-continued

```
gcaaccatga cccaccagtc agctgccggc tctcagctcg aggttccccg cgacctcgtg    780
cgcatctcca ttggtattga agacattgaa gacctgctcg cagatgtcga gcaggccctc    840
aataaccttt agaaactatt tggcggcaag cagcttttca atataagcaa tgcgagcctc    900
caccatgtag ccgaagagtt cgtcagaagt tgagacggac tcttcgactg ctttacgggt    960
cagtggcgct tccacatctg ggttctcatc aagccatggc ttaggaaccg agcaaacac    1020
atccggcttt cgccctctg gacgattgtc aaggtgtag tcggatcccc gggtaccgag    1080
ctcgaattca ctggccgtcg ttttacaacg tcgtgactgg gaaaaccctg gcgttaccca   1140
acttaatcgc cttgcagcac atccccctt cgccagctgg cgtaatagcg aagaggcccg    1200
caccgatcgc ccttcccaac agttgcgcag cctgaatggc gaatggcgat aagctagctt   1260
cacgctgccg caagcactca gggcgcaagg gctgctaaag gaagcggaac acgtagaaag   1320
ccagtccgca gaaacggtgc tgaccccgga tgaatgtcag ctactgggct atctggacaa   1380
gggaaaacgc aagcgcaaag agaaagcagg tagcttgcag tgggcttaca tggcgatagc   1440
tagactgggc ggttttatgg acagcaagcg aaccggaatt gccagctggg gcgccctctg   1500
gtaaggttgg gaagccctgc aaagtaaact ggatggcttt cttgccgcca aggatctgat   1560
ggcgcagggg atcaagatct gatcaagaga caggatgagg atcgtttcgc atgattgaac   1620
aagatggatt gcacgcaggt tctccggccg cttgggtgga gaggctattc ggctatgact   1680
gggcacaaca gacaatcggc tgctctgatg ccgccgtgtt ccggctgtca gcgcaggggc   1740
gcccggttct ttttgtcaag accgacctgt ccggtgccct gaatgaactc caagacgagg   1800
cagcgcggct atcgtggctg gccacgacgg gcgttccttg cgcagctgtg ctcgacgttg   1860
tcactgaagc gggaagggac tggctgctat gggcgaagt gccggggcag gatctcctgt   1920
catctcacct gctcctgcc gagaaagtat ccatcatggc tgatgcaatg cggcggctgc   1980
atacgcttga tccggctacc tgcccattcg accaccaagc gaaacatcgc atcgagcgag   2040
cacgtactcg gatggaagcc ggtcttgtcg atcaggatga tctggacgaa gagcatcagg   2100
ggctcgcgcc agccgaactg ttcgccaggc tcaaggcgcg gatgcccgac ggcgaggatc   2160
tcgtcgtgac ccatggcgat gcctgcttgc cgaatatcat ggtggaaaat ggccgctttt   2220
ctggattcat cgactgtggc cggctgggtg tggcggaccg ctatcaggac atagcgttgg   2280
ctacccgtga tattgctgaa gagcttggcg gcgaatgggc tgaccgcttc ctcgtgcttt   2340
acggtatcgc cgctcccgat tcgcagcgca tcgccttcta tcgccttctt gacgagttct   2400
tctgagcgg actctggggt tcgctagagg atcgatcctt tttaacccat cacatatacc   2460
tgccgttcac tattatttag tgaaatgaga tattatgata ttttctgaat tgtgattaaa   2520
aaggcaactt tatgcccatg caacagaaac tataaaaaat acagaatg aaaagaaaca   2580
gatagatttt ttagttcttt aggcccgtag tctgcaaatc cttttatgat tttctatcaa   2640
acaaaagagg aaaatagacc agttgcaatc caaacgagag tctaatagaa tgaggtcgaa   2700
aagtaaatcg cgcgggtttg ttactgataa agcaggcaag acctaaaatg tgtaagggc    2760
aaagtgtata cttggcgtc accccttaca tatttaggt cttttttat tgtgcgtaac    2820
taacttgcca tcttcaaaca ggagggctgg aagaagcaga ccgctaacac agtacataaa   2880
aaaggagaca tgaacgatga acatcaaaaa gtttgcaaaa caagcaacag tattaacctt   2940
tactaccgca ctgctggcag gaggcgcaac tcaagcgttt gcgaaagaaa cgaaccaaaa   3000
gccatataag gaaacatacg gcatttccca tattacacgc catgtatagc tgcaaatccc   3060
tgaacagcaa aaaaatgaaa aatatcaagt ttctgaattt gattcgtcca caattaaaaa   3120
```

```
tatctcttct gcaaaaggcc tggacgtttg ggacagctgg ccattacaaa acgctgacgg    3180
cactgtcgca aactatcacg gctaccacat cgtctttgca ttagccggag atcctaaaaa    3240
tgcggatgac acatcgattt acatgttcta tcaaaaagtc ggcgaaactt ctattgacag    3300
ctggaaaaac gctggccgcg tctttaaaga cagcgacaaa ttcgatgcaa atgattctat    3360
cctaaaagac caaacacaag aatggtcagg ttcagccaca tttacatctg acggaaaaat    3420
ccgtttattc tacactgatt tctccggtaa acattacggc aaacaaacac tgacaactgc    3480
acaagttaac gtatcagcat cagacagctc tttgaacatc aacggtgtag aggattataa    3540
atcaatcttt gacggtgacg gaaaaacgta tcaaaatgta cagcagttca tcgatgaagg    3600
caactacagc tcaggcgaca accatacgct gagagatcct cactacgtag aagataaagg    3660
ccacaaatac ttagtatttg aagcaaacac tggaactgaa gatggctacc aaggcgaaga    3720
atctttattt aacaaagcat actatggcaa aagcacatca ttcttccgtc aagaaagtca    3780
aaaacttctg caaagcgata aaaaacgcac ggctgagtta gcaaacgcg ctctcggtat    3840 gattgagcta aacgatgatt acacactgaa aaaagtgatg aaaccgctga ttgcatctaa    3900
cacagtaaca gatgaaattg aacgcgcgaa cgtctttaaa atgaacggca aatggtacct    3960
gttcactgac tcccgcggat caaaaatgac gattgacggc attacgtcta acgatattta    4020
catgcttggt tatgttttcta attctttaac tggcccatac aagccgctga acaaaactgg    4080
ccttgtgtta aaaatggatc ttgatcctaa cgatgtaacc tttacttact cacacttcgc    4140
tgtacctcaa gcgaaggaa acaatgtcgt gattacaagc tatatgacaa acagaggatt    4200
ctacgcagac aaacaatcaa cgtttgcgcc gagcttcctg ctgaacatca aaggcaagaa    4260
aacatctgtt gtcaaagaca gcatccttga acaaggacaa ttaacagtta acaaataaaa    4320
acgcaaaaga aaatgccgat gggtaccgag cgaaatgacc gaccaagcga cgcccaacct    4380
gccatcacga gatttcgatt ccaccgccgc cttctatgaa aggttgggct tcggaatcgt    4440
tttccgggac gccctcgcgg acgtgctcat agtccacgac gcccgtgatt ttgtagccct    4500
ggccgacggc cagcaggtag gccgacaggc tcatgccggc cgccgccgcc ttttcctcaa    4560
tcgctcttcg ttcgtctgga aggcagtaca ccttgatagg tgggctgccc ttcctggttg    4620
gcttggtttc atcagccatc cgcttgccct catctgttac gccggcggta gccggccagc    4680
ctcgcagagc aggattcccg ttgagcaccg ccaggtgcga taagggaca gtgaagaagg    4740 aacacccgct cgcgggtggg cctacttcac ctatcctgcc cggctgacgc cgttggatac    4800
accaaggaaa gtctacacga acccttggc aaaatcctgt atatcgtgcg aaaaaggatg    4860
gatataccga aaaatcgct ataatgaccc cgaagcaggg ttatgcagcg aaaagcgct    4920 gcttccctgc tgtttttgtgg aatatctacc gactggaaac aggcaaatgc aggaaattac    4980
tgaactgagg ggacaggcga gagacgatgc caaagagctc ctgaaaatct cgataactca    5040
aaaaatacgc ccggtagtga tcttatttca ttatggtgaa agttggaacc tcttacgtgc    5100
cgatcaacgt ctcatttcg ccaaaagttg gcccagggct tcccggtatc aacagggaca    5160
ccaggattta tttattctgc gaagtgatct tccgtcacag gtatttattc ggcgcaaagt    5220
gcgtcgggtg atgctgccaa cttactgatt tagtgtatga tggtgttttt gaggtgctcc    5280
agtggcttct gtttctatca gctcctgaaa atctcgataa ctcaaaaaat acgcccggta    5340
gtgatcttat ttcattatgg tgaaagttgg aacctcttac gtgccgatca acgtctcatt    5400
ttcgccaaaa gttgggccag ggcttccgg tatcaacagg gacaccagga tttatttatt    5460
ctgcgaagtg atcttccgtc acaggtattt attcggcgca aagtgcgtcg ggtgatgctg    5520
```

```
ccaacttact gatttagtgt atgatggtgt ttttgaggtg ctccagtggc ttctgtttct    5580
atcagggctg gatgatcctc cagcgcgggg atctcatgct ggagttcttc gcccacccca    5640
aaaggatcta ggtgaagatc cttttgata atctcatgac caaaatccct taacgtgagt     5700
tttcgttcca ctgagcgtca gacccgtag aaaagatcaa aggatcttct tgagatcctt    5760
tttttctgcg cgtaatctgc tgcttgcaaa caaaaaaacc accgctacca gcggtggttt    5820
gtttgccgga tcaagagcta ccaactcttt ttccgaaggt aactggcttc agcagagcgc    5880
agataccaaa tactgttctt ctagtgtagc cgtagttagg ccaccacttc aagaactctg    5940
tagcaccgcc tacatacctc gctctgctaa tcctgttacc agtggctgct gccagtggcg    6000
ataagtcgtg tcttaccggg ttggactcaa gacgatagtt accggataag gcgcagcggt    6060
cgggctgaac gggggttcg tgcacacagc ccagcttgga gcgaacgacc tacaccgaac     6120
tgagatacct acagcgtgag ctatgagaaa gcgccacgct tcccgaaggg agaaaggcgg    6180
acaggtatcc ggtaagcggc agggtcggaa caggagagcg cacgagggag cttccagggg    6240
gaaacgcctg gtatctttat agtcctgtcg ggtttcgcca cctctgactt gagcgtcgat    6300
ttttgtgatg ctcgtcaggg gggcggagcc tatggaaaaa cgccagcaac gcggcctttt    6360
tacggttcct ggccttttgc tggccttttg ctcacatgtt ctttcctgcg ttatccctg    6420 attctgtgga taaccgtatt accgcctttg agtgagctga taccgctcgc cgcagccgaa    6480
cgaccgagcg cagcgagtca gtgagcgagg aagcggaaga gcgcccaata cgcaaaccgc    6540
ctctccccgc gcgttggccg attcattaat gcagctggca cgacaggttt cccgactgga    6600
aagcgggcag tgagcgcaac gcaattaatg tgagttagct cactcattag gcaccccagg    6660
ctttacactt tatgcttccg gctcgtatgt tgtgtggaat tgtgagcgga taacaatttc    6720
acacaggaaa cagctatgac catgattacg ccaagcttgc atgcctgcag gtcgactct     6779
```